US006228610B1

(12) United States Patent
Flor et al.

(10) Patent No.: US 6,228,610 B1
(45) Date of Patent: May 8, 2001

(54) HUMAN METABOTROPIC GLUTAMATE RECEPTOR SUBTYPES (HMR4, HMR6, HMR7) AND RELATED DNA COMPOUNDS

(75) Inventors: Peter Josef Flor, Freiburg; Rainer Kuhn, Lörrach, both of (DE); Kristin Lindauer; Irene Püttner, both of Basel (CH); Thomas Knöpfel, Rheinfelden (CH)

(73) Assignee: Novartis Corporation, New York, NY (US)

( * ) Notice: Subject to any disclaimer, the term of this patent is extended or adjusted under 35 U.S.C. 154(b) by 0 days.

(21) Appl. No.: 08/617,785

(22) PCT Filed: Sep. 7, 1994

(86) PCT No.: PCT/EP94/02991

§ 371 Date: Mar. 19, 1996

§ 102(e) Date: Mar. 19, 1996

(87) PCT Pub. No.: WO95/08627

PCT Pub. Date: Mar. 30, 1995

(30) Foreign Application Priority Data

Sep. 20, 1993 (EP) .................................................. 93810663
Aug. 19, 1994 (EP) .................................................... 9416553

(51) Int. Cl.$^7$ .......................... G01N 33/53; C07K 14/00; C07H 21/04; C12N 15/63

(52) U.S. Cl. ...................... 435/69.1; 435/7.1; 435/320.1; 435/325; 530/350; 536/23.5

(58) Field of Search .............................. 435/7.1, 7.2, 325, 435/252.3, 253.11, 320.1, 69.1; 530/305, 402, 300; 536/23.1, 23.5, 24.31

(56) References Cited

U.S. PATENT DOCUMENTS

| 3,829,583 | * | 8/1974 | Yuen ..................................... 426/175 |
| 5,202,257 |   | 4/1993 | Heinemann et al. ............. 435/252.3 |
| 5,385,831 |   | 1/1995 | Mutvihill et al. ................... 435/69.1 |
| 5,521,297 | * | 5/1996 | Daggett et al. ..................... 536/23.5 |
| 5,738,999 | * | 4/1998 | Sergerson et al. ................. 435/7.21 |

FOREIGN PATENT DOCUMENTS

| 0 568 384 A1 | 4/1993 | (EP) . |
| 0 569 240 A1 | 5/1993 | (EP) . |
| 0 574 275 A2 | 6/1993 | (EP) . |
| WO 93/24629 | 12/1993 | (WO) . |
| WO 94/27602 | 12/1994 | (WO) . |
| WO 95/18154 | 7/1995 | (WO) . |
| WO 95/22609 | 8/1995 | (WO) . |
| WO 96/06167 | 2/1996 | (WO) . |

OTHER PUBLICATIONS

Flor et al., "Molecular Cloning, Functional Expression and Pharmacological Characterization of the Human Metabotropic Glutamate Receptor Type 4", *Neuropharmacology*, 34(2): 149–155 (1995).

Flor et al., "Molecular Cloning, Functional Expression and Pharmacological Characterization of the Human Metabotropic Glutamate Receptor Type 2", *European J. of Neuroscience*, 7: 622–629 (1995).

Hollman et al., "Cloning by functional expression of a member of the glutamate receptor family", *Nature*, 32:643–648 (1989).

Honoré, T., "Excitatory Amino Acid Receptor Subtypes and Specific Antagonists", *Medicinal Research Reviews*, 9(1): 1–23 (1989).

Knöpfel et al., "Metabotropic Glutamate Receptors: Novel Targets for Drug Development", *J. Medicinal Chemistry*, 38(9):1417–1436 (1995).

Knöpfel et al., "Pharmacological Characterization of MCCG and MAP4 at the mGluR1b, MGluR2 and MGluR4A Human Metabotropic Glutamate Receptor Subtypes", *Neuropharmacology*, 34(8): 1099–1102 (1995).

Knöpfel et al., "Profiling of trans–azetidine–2,4–dicarboxylic acid at the human metabotropic glutamate receptors $mGlu_{1b, -2, -4a}$ and $_{-5a}$", *European J. of Pharmacology*, 288: 389–392 (1995).

Masu et al., "Sequence and expression of a metabotropic glutamate receptor", *Nature*, 349: 760–765 (1991).

Nakajima et al., "Molecular Characterization of a Novel Retinal Metabotropic Glutamate Receptor mGluR6 with a High Agonist Selectivity for L–2–Aminoo–4–phosphonobutyrate", *J. Biol. Chem.*, 268: 11868–11873 (1993).

Nakajima et al., "Direct Linkage of Three Tachykinin Receptors to Stimulation of Both Phosphatidylinositol Hydrolysis and Cyclid AMP Cascades in Transfected Chinese Hamster Ovary Cells", *J. of Biol. Chem.*, 267(4):2437–2442 (1992).

Nakanishi, S., "Molecular Diversity of Glutamate Receptors and Implications for Brain Function", *Science*, 258: 597–603 (1992).

Okamoto et al., "Molecular Characterization of a New Metabotropic Glutamate Receptor mGluR7 Coupled to Inhibitory Cyclic AMP Signal Transduction", *J. Biol. Chem.*, 269: 1231–1236 (1994).

Pin et al., "Domains involved in the specificity of G protein activation in phospholipase C–coupled metabotropic glutamate receptors", *EMBO J.*, 13(2): 342–348 (1994).

Pin et al., "Alternative splicing generates metabotropic glutamte receptors inducing different patterns of calcium release in *Xenopus* oocytes", *Proc. Natl. Acad. Sci.*, 89: 10331–10335 (1992).

(List continued on next page.)

*Primary Examiner*—Prema Mertz
*Assistant Examiner*—Joseph F. Murphy
(74) *Attorney, Agent, or Firm*—David E. Wildman; Gregory D. Ferraro

(57) ABSTRACT

The present invention relates to human metabotropic glutamate receptor (hmGluR) proteins, isolated nucleic acids coding therefor, host cells producing the proteins of the invention, methods for the preparation of such proteins, nucleic acids and host cells, and uses thereof.

18 Claims, No Drawings

OTHER PUBLICATIONS

Sugiyama et al., "A new type of glutamate receptor linked to inositol phospholipid metabolism", *Nature*, 325:531–533 (1987).

Sugiyama et al., "Glutamate Receptor Subtypes May be Classified into Two Major Categories: A Study on *Xenopus Oocytes* Injected with Rat Brain mRNA", *Neuron*, 3:129–132 (1989).

Tanabe et al., "A Family of Metabotropic Glutamate Receptors", *Neuron* 8:169–179 (1992).

Tanabe et al., "Signal Transduction, Pharmacological Properties, and Expression Patterns of Two Rat Metabotropic Glutamate Receptors, mGluR3 and MGluR4", *J. Neuroscience*, 13(4): 1372–1378 (1993).

Prickett et al., A calucium–dependent antibody for identification and purification of recombinant proteins, Bio Techniques, 7(6): 580–589, 1989.*

Probst et al., Sequence alignment of the G–protein coupled receptor superfamily, DNA and Cell Biology, 11(1): 1–20, 1992.*

Darnell et al., Molecular Cell Biology, Scientific American Books: New York, NY, pp.223–235, 1986.*

Stratagene Catalogue, 1991, p. 66.*

* cited by examiner

HUMAN METABOTROPIC GLUTAMATE RECEPTOR SUBTYPES (HMR4, HMR6, HMR7) AND RELATED DNA COMPOUNDS

The present invention relates to human metabotropic glutamate receptor (hmGluR) proteins, isolated nucleic acids coding therefor, host cells producing the proteins of the invention, methods for the preparation of such proteins, nucleic acids and host cells, and uses thereof. Furthermore, the invention provides antibodies directed against the hmGluR proteins of the invention.

Metabotropic glutamate receptors (hmGluR) belong to the class of G-protein (guanine nucleotide binding protein) coupled receptors which upon binding of a glutamatergic ligand may transduce an extracellular signal via an intracellular second messenger system such as calcium ions, a cyclic nucleotide, diacylglycerol and inositol 1,4,5-triphosphate into a physiological response. Possessing seven putative transmembrane spanning segments, preceded by a large extracellular amino-terminal domain and followed by a large carboxy-terminal domain metabotropic glutamate receptors are characterized by a common structure. Based on the degree of sequence identity at the amino acid level the class of mGluR can be divided into different subfamilies comprising individual receptor subtypes (Nakanishi, Science 258, 597–603 (1992)). Each mGluR subtype is encoded by a unique gene. Regarding the homology of an individual mGluR subtype to another subtype of a different subfamily, the amino acid sequences are less than about 50% identical. Within a subfamily the degree of sequence identity is generally less than about 70%. Thus a particular subtype may be characterized by its amino acid sequence homology to another mGluR subtype, especially a subtype of the same mammalian species. Furthermore, a particular subtype may be characterized by its region and tissue distribution, its cellular and subcellular expression pattern or by its distinct physiological profile, e.g. by its electrophysiological and pharmacological properties.

The amino acid L-glutamate being the major excitatory neurotransmitter, glutamatergic systems are presumed to play an important role in numerous neuronal processes including fast excitatory synaptic transmission, regulation of neurotransmitter releases, long-term potentation, learning and memory, developmental synaptic plasticity, hypoxic-ischemic damage and neuronal cell death, epileptiform seizures, as well as the pathogenesis of several neurodegenerative disorders. Up to today, no information is available on human metabotropic glutamate receptor (hmGluR) subtypes, e.g. on their amino acid sequence or tissue distribution. This lack of knowledge particularly hampers the search for human therapeutic agents capable of specifically influencing any disorder attributable to a defect in the glutamatergic system. In view of the potential physiological and pathological significance of metabotropic glutamate receptors, there is a need for human receptor subtypes and cells producing such subtypes in amounts sufficient for elucidating the electrophysiological and pharmacological properties of these proteins. For example, drug screening assays require purified human receptor proteins in an active form, which have not yet been attainable.

It is an object of the present invention to fulfill this need, namely to provide distinct hmGluR subtypes, nucleic acids coding therefor and host cells producing such subtypes. In particular, the present invention discloses the hmGluR subfamily comprising the subtype designated hmGluR4, and the individual proteins of said subfamily. In the following, said subfamily will be referred to as the hmGluR4 subfamily. Contrary to other hmGluR subtypes the members of this subfamily are potently activated by L-2-amino-4-phosphobutyric acid (AP4) and, when expressed e.g. in Chinese hamster ovary (CHO) cells or baby hamster kidney (BHK) cells, negatively coupled to adenylate cyclase via G protein. Using a system comprising a recombinant hmGluR subtype of the invention in screening for hmGluR reactive drugs offers (among others) the possibilities of attaining a greater number of receptors per cell giving greater yield of reagent and a higher signal to noise ratio in assays as well as increased receptor subtype specificity (potentially resulting in greater biological and disease specificity).

More specifically, the present invention relates to a hmGluR subtype characterized in that its amino acid sequence is more than about 65% identical to the sequence of the hmGluR4 subtype having the amino acid sequence depicted in SEQ ID NO:2.

According to the invention the expression "hmGluR subtype" refers to a purified protein which belongs to the class of G protein-coupled receptors and which upon binding of a glutamatergic ligand transduces an extracellular signal via an intracellular second messenger system. In such case, a subtype of the invention is characterized in that it modifies the level of a cyclic nucleotide (cAMP, cGMP). Alternatively, signal transduction may occur via direct interaction of the G protein coupled to a receptor subtype of the invention with another membrane protein, such as an ion channel or another receptor. A receptor subtype of the invention is believed to be encoded by a distinct gene which does not encode another metabotropic glutamate receptor subtype. A particular subtype of the invention may be characterized by its distinct physiological profile, preferably by its signal transduction and pharmacological properties. Pharmacological properties are e.g. the selectivity for agonists and antagonist responses.

As defined herein, a glutamatergic ligand is e.g. L-glutamate or another compound interacting with, and particularly binding to, a hmGluR subtype in a glutamate like manner, such as ACPD (1S,3R-1-aminocyclopentane-1,3-dicarboxylic acid), an ACPD-like ligand, e.g. QUIS (quisqualate), AP4, and the like. Other ligands, e.g. (R,S)-α-methylcarboxyphenylglycine (MCPG) or α-methyl-L-AP4, may interact with a receptor of the invention in such a way that binding of glutamatergic ligand is prevented.

As used hereinbefore or hereinafter, the terms "purified" or "isolated" are intended to refer to a molecule of the invention in an enriched or pure form obtainable from a natural source or by means of genetic engineering. The purified proteins, DNAs and RNAs of the invention may be useful in ways that the proteins, DNAs and RNAs as they naturally occur are not, such as identification of compounds selectively modulating the expression or the activity of a hmGluR of the invention.

Purified hmGluR of the invention means a member of the hmGluR4 subfamily which has been identified and is free of one or more components of its natural environment. Purified hmGluR includes purified hmGluR of the invention in recombinant cell culture. The enriched form of a subtype of the invention refers to a preparation containing said subtype in a concentration higher than natural, e.g. a cellular membrane fraction comprising said subtype. If said subtype is in a pure form it is substantially free from other macromolecules, particularly from naturally occurring proteinaceous contaminations. If desired, the subtype of the invention may be solubilized. A preferred purified hmGluR subtype of the invention is a recombinant protein. Preferably, the subtype of the invention is in an active state meaning that it has both ligand binding and signal transduction activity. Receptor activity is measured according to methods known in the art, e.g. using a binding assay or a functional assay, e.g. an assay as described below.

Preferred hmGluR subtypes of the hmGluR4 subfamily are subtypes hmGluR4, hmGluR7 and hmGluR6. A particularly preferred hmGluR4 subtype is the protein having the amino acid sequence set forth in SEQ ID NO:2. A hmGluR7-type protein may comprise a polypeptide selected from the group consisting of the polypeptides having the amino acid sequences depicted in SEQ ID NOs: 4, 6, 8 and 10, respectively. Such hmGluR7 subtype is preferred. Particularly preferred are the hmGluR7 subtypes having the amino acid sequences set forth in SEQ ID NOs: 12 and 14, respectively. A preferred hmGluR6-type protein comprises a polypeptide having the amino acid sequence depicted in SEQ ID NO:16.

The invention is further intended to include variants of the receptor subtypes of the invention. For example, a variant of a hmGluR subtype of the invention is a functional or immunological equivalent of said subtype. A functional equivalent is a protein, particularly a human protein, displaying a physiological profile essentially identical to the profile characteristic of said particular subtype. The physiological profile in vitro and in vivo includes receptor effector function, electrophysiological and pharmacological properties, e.g. selective interaction with agonists or antagonists. Exemplary functional equivalents may be splice variants encoded by mRNA generated by alternative splicing of a primary transcript, amino acid mutants and glycosylation variants. An immunological equivalent of a particular hmGluR subtype is a protein or peptide capable of generating antibodies specific for said subtype. Portions of the extracellular domain of the receptor, e.g. peptides consisting of at least 6 to 8 amino acids, particularly 20 amino acids, are considered particularly useful immunological equivalents.

Further variants included herein are membrane-bound and soluble fragments and covalent or aggregative conjugates with other chemical moieties, these variants displaying one or more receptor functions, such as ligand binding or signal transduction. Exemplary fragments of hmGluR subtypes of the invention are the polypeptides having the amino acid sequences set forth in SEQ ID NOs: 4, 6, 8, 10 and 16, respectively. The fragments of the invention are obtainable from a natural source, by chemical synthesis or by recombinant techniques. Due to their capability of competing with the endogenous counterpart of a hmGluR subtype of the invention for its endogenous ligand, fragments, or derivatives thereof, comprising the ligand binding domain are envisaged as therapeutic agents.

Covalent derivatives include for example aliphatic esters or amides of a receptor carboxyl group, O-acyl derivatives of hydroxyl group containing residues and N-acyl derivatives of amino group containing residues. Such derivatives can be prepared by linkage of functionalities to reactable groups which are found in the side chains and at the N- and C-terminus of the receptor protein. The protein of the invention can also be labeled with a detectable group, for example radiolabeled, covalently bound to rare earth chelates or conjugated to a fluorescent moiety.

Further derivatives are covalent conjugates of a protein of the invention with another protein or peptide (fusion proteins). Examples are fusion proteins comprising different portions of different glutamate receptors. Such fusion proteins may be useful for changing the coupling to G-proteins and/or improving the sensitivity of a functional assay. For example, in such fusion proteins or chimeric receptors, the intracellular domains of a subtype of the invention may be replaced with the corresponding domains of another mGluR subtype, particularly another hmGluR subtype, e.g. a hmGLuR subtype belonging to another subfamily. Particularly suitable for the construction of such a chimeric receptor are the intracellular domains of a receptor which activates the phospholipase C/Ca$^{2+}$ signaling pathway, e.g. mGluR1 (Masu et al., Nature 349, 760–765) or mGluR5. An intracellular domain suitable for such an exchange is e.g. the second intracellular loop, also referred to as i2 (Pin et al., EMBO J. 13, 342–348 (1994)). Thus it is possible to analyze the interaction of a test compound with a ligand binding domain of a receptor of the invention using an assay for calcium ions. The chimeric receptor according to the invention can be synthesized by recombinant techniques or agents known in the art as being suitable for crosslinking proteins.

Aggregative derivatives are e.g. adsorption complexes with cell membranes.

In another embodiment, the present invention relates to a composition of matter comprising a hmGluR subtype of the invention.

The proteins of the invention are useful e.g. as immunogens, in drug screening assays, as reagents for immunoassays and in purification methods, such as for affinity purification of a binding ligand.

A protein of the invention is obtainable from a natural source, e.g. by isolation from brain tissue, by chemical synthesis or by recombinant techniques.

The invention further provides a method for preparing a hmGluR subtype of the invention characterized in that suitable host cells producing a receptor subtype of the invention are multiplied in vitro or in vivo. Preferably, the host cells are transformed (transfected) with a hybrid vector comprising an expression cassette comprising a promoter and a DNA sequence coding for said subtype which DNA is controlled by said promoter. Subsequently, the hmGluR subtype of the invention may be recovered. Recovery comprises e.g. isolating the subtype of the invention from the host cells or isolating the host cells comprising the subtype, e.g. from the culture broth. Particularly preferred is a method for preparation of a functionally active receptor.

HmGluR muteins may be produced from a DNA encoding a hmGluR protein of the invention which DNA has been subjected to in vitro mutagenesis resulting e.g. in an addition, exchange and/or deletion of one or more amino acids. For example, substitutional, deletional and insertional variants of a hmGluR subtype of the invention are prepared by recombinant methods and screened for immuno-crossreactivity with the native forms of the hmGluR.

A protein of the invention may also be derivatized in vitro according to conventional methods known in the art.

Suitable host cells include eukaryotic cells, e.g. animal cells, plant cells and fungi, and prokaryotic cells, such as gram-positive and gram-negative bacteria, e.g. *E. coli*. Preferred eukaryotic host cells are of amphibian or mammalian origin.

As used herein, in vitro means ex vivo, thus including e.g. cell culture and tissue culture conditions.

This invention further covers a nucleic acid (DNA, RNA) comprising a purified, preferably recombinant, nucleic acid (DNA, RNA) coding for a subtype of the invention, or a fragment of such a nucleic acid. In addition to being useful for the production of the above recombinant hmGluR proteins, these nucleic acid are useful as probes, thus readily enabling those skilled in the art to identify and/or isolate nucleic acid encoding a hmGluR protein of the invention. The nucleic acid may be unlabeled or labeled with a detectable moiety. Furthermore, nucleic acid according to the invention is useful e.g. in a method for determining the presence of hmGluR, said method comprising hybridizing the DNA (or RNA) encoding (or complementary to) hmGluR to test sample nucleic acid and to determine the presence of hmGluR.

Purified hmGluR encoding nucleic acid of the invention includes nucleic acid that is free from at least one contaminant nucleic acid with which it is ordinarily associated in the natural source of hmGluR nucleic acid. Purified nucleic acids thus is present in other than in the form or setting in which it is found in nature. However, purified hmGluR nucleic acid embraces hmGluR nucleic acid in ordinarily hmGluR expressing cells where the nucleic acid is in a chromosomal location different from that of natural cells or is otherwise flanked by a different DNA sequence than that found in nature.

In particular, the invention provides a purified or isolated DNA molecule encoding a hmGluR subtype of the invention, or a fragment of such DNA. By definition, such a DNA comprises a coding single DNA, a double stranded DNA consisting of said coding DNA and complementary DNA thereto, or this complementary (single stranded) DNA itself. Preferred is a DNA coding for the above captioned preferred hmGluR subtypes, or a fragment thereof. Furthermore, the invention relates to a DNA comprising such a DNA.

More specifically, preferred is a DNA coding for a hmGluR4 subtype or a portion thereof, particularly a DNA encoding the hmGluR4 subtype having the amino acid sequence set forth in SEQ ID NO:2, e.g. the DNA with the nucleotide sequence set forth in SEQ ID NO:1. An exemplary DNA fragment coding for a portion of hmGluR4 is the hmGluR4-encoding portion of cDNA cmR20 as described in the Examples.

Equally preferred is a DNA encoding a hmGluR7 subtype, particularly a DNA encoding any of the hmGluR7 subtypes having the amino acid sequences set forth in SEQ ID NOs: 12 and 14, respectively, e.g. the DNAs with the nucleotide sequences set forth in SEQ ID NOs: 11 and 13, respectively. The invention further provides a DNA fragment encoding a portion of a hmGluR7 subtype, particularly the hmGluR7 subtypes identified as preferred above. Exemplary hmGluR7 DNA fragments include the hmGluR7-encoding portions of cDNAs cmR2, cmR3, cmR5 and cR7PCR1, as described in the Examples, or a DNA fragment which encodes substantially the same amino acid sequence as that encoded by the hmGluR7-encoding portion of plasmid cmR2 deposited with the DSM on Sep. 13, 1993, under accession number DSM 8550. These DNAs encode portions of putative splice variants of the hmGluR7 subtype described herein.

Also preferred is a DNA encoding a hmGluR6 subtype or a portion thereof, particularly a DNA encoding the portion of the hmGluR6 subtype, the amino acid sequence of which is depicted in SEQ ID NO:16, or a DNA which encodes substantially the same amino acid sequence as that encoded by the hmGluR6-encoding portion of plasmid cmR1 deposited with the DSM on Sep. 13, 1993, under accession number DSM 8549. An exemplary DNA sequence is set forth in SEQ ID NO:15.

The nucleic acid sequences provided herein may be employed to identify DNAs encoding further hmGluR subtypes. For example, nucleic acid sequences of the invention may be used for identifying DNAs encoding further hmGluR subtypes belonging to the subfamily comprising hmGluR 4. A method for identifying such DNA comprises contacting human DNA with a nucleic acid probe described above and identifying DNA(s) which hybridize to that probe.

Exemplary nucleic acids of the invention can alternatively be characterized as those nucleic acids which encode a hmGluR subtype of the invention and hybridize to a DNA sequence set forth in SEQ ID NOs. 1, 3, 5, 7, 9, 11, 13 or 15, or a selected portion (fragment) of said DNA sequence. For example, selected fragments useful for hybridization are the protein-encoding portions of said DNAs. Preferred are such DNAs encoding a hmGluR of the invention which hybridize under high-stringency conditions to the above-mentioned DNAs.

Stringency of hybridization refers to conditions under which polynucleic acids hybrids are stable. Such conditions are evident to those of ordinary skill in the field. As known to those of skill in the art, the stability of hybrids is reflected in the melting temperature ($T_m$) of the hybrid which decreases approximately 1 to 1.5° C. with every 1% decrease in sequence homology. In general, the stability of a hybrid is a function of sodium ion concentration and temperature. Typically, the hybridization reaction is performed under conditions of higher stringency, followed by washes of varying stringency.

As used herein, high stringency refers to conditions that permit hybridization of only those nucleic acid sequences that form stable hybrids in 1 M $Na^+$ at 65–68° C. High stringency conditions can be provided, for example, by hybridization in an aqueous solution containing 6×SSC, 5×Denhardt's, 1% SDS (sodium dodecyl sulfate), 0.1 $Na^+$ pyrophosphate and 0.1 mg/ml denatured salmon sperm DNA as non specific competitor. Following hybridization, high stringency washing may be done in several steps, with a final wash (about 30 min) at the hybridization temperature in 0.2–0.1×SSC, 0.1% SDS.

Moderate stringency refers to conditions equivalent to hybridization in the above described solution but at about 60–62° C. In that case the final wash is performed at the hybridization temperature in 1×SSC, 0.1% SDS.

Low stringency refers to conditions equivalent to hybridization in the above described solution at about 50–52° C. In that case, the final wash is performed at the hybridization temperature in 2×SSC, 0.1% SDS.

It is understood that these conditions may be adapted and duplicated using a variety of buffers, e.g. formamide-based buffers, and temperatures. Denhart's solution and SSC are well known to those of skill in the art as are other suitable hybridization buffers (see, e.g. Sambrook, J., Fritsch, E. F. and Maniatis, T. (1989) Molecular Cloning: A Laboratory Manual (2nd edition), Cold Spring Harbor Laboratory Press, Cold Spring Harbor, USA, or Ausubel, F. M., et al. (1993) Current Protocols in Molecular Biology, Greene and Wiley, USA). Optimal hybridization conditions have to be determined empirically, as the length and the GC content of the probe also play a role.

Given the guidance of the present invention, the nucleic acids of the invention are obtainable according to methods well known in the art. The present invention further relates to a process for the preparation of such nucleic acids.

For example, a DNA of the invention is obtainable by chemical synthesis, by recombinant DNA technology or by polymerase chain reaction (PCR). Preparation by recombinant DNA technology may involve screening a suitable cDNA or genomic library. A suitable method for preparing a DNA or of the invention comprises the synthesis of a number of oligonucleotides, their amplification by PCR methods, and their splicing to give the desired DNA sequence. Suitable libraries are commercially available, e.g. the libraries employed in the Examples, or can be prepared from neural or neuronal tissue samples, e.g. hippocampus and cerebellum tissue, cell lines and the like.

For individual hmGluR subtypes (and splice variants) of the invention the expression pattern in neural or neuronal tissue may vary. Thus, in order to isolate cDNA encoding a particular subtype (or splice variant), it is advantageous to screen libraries prepared from different suitable tissues or cells. As a screening probe, there may be employed a DNA or RNA comprising substantially the entire coding region of a hmGluR subtype of the invention, or a suitable oligonucleotide probe based on said DNA. A suitable oligonucleotide probe (for screening involving hybridization) is a single stranded DNA or RNA that has a sequence of nucleotides that includes at least 14 contiguous bases that are the same as (or complementary to) any 14 or more contiguous bases set forth in any of SEQ ID NOs: 1, 3, 5, 7, 9, 11, 13 and 15. The probe may be labeled with a suitable chemical moiety for ready detection. The nucleic acid sequences selected as probes should be of sufficient length and sufficiently unambiguous so that false positive results are minimized.

Preferred regions from which to construct probes include 5' and/or 3' coding sequences, sequences predicted to encode ligand binding sites, and the like. For example, either the full-length cDNA clones disclosed herein or fragments thereof can be used as probes. Preferably, nucleic acid probes of the invention are labeled with suitable label means for ready detection upon hybridization. For example, a suitable label means is a radiolabel. The preferred method of labelling a DNA fragment is by incorporating $^{32}$P-labelled α-dATP with the Klenow fragment of DNA polymerase in a random priming reaction, as is well known in the art. Oligonucleotides are usually end-labeled with $^{32}$P-labeled γ-ATP and polynucleotide kinase. However, other methods (e.g. non-radioactive) may also be used to label the fragment or oligonucleotide, including e.g. enzyme labelling and biotinylation.

After screening the library, e.g. with a portion of DNA including substantially the entire hmGluR-encoding sequence or a suitable oligonucleotide based on a portion of said DNA, positive clones are identified by detecting a hybridization signal; the identified clones are characterized by restriction enzyme mapping and/or DNA sequence analysis, and then examined, e.g. by comparison with the sequences set forth herein, to ascertain whether they include DNA encoding a complete hmGluR (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

Furthermore, in order to detect any abnormality of an endogenous hmGluR subtype of the invention genetic screening may be carried out using the nucleotide sequences of the invention as hybridization probes. Also, based on the nucleic acid sequences provided herein antisense-type therapeutic agents may be designed.

It is envisaged that the nucleic acid of the invention can be readily modified by nucleotide substitution, nucleotide deletion, nucleotide insertion or inversion of a nucleotide stretch, and any combination thereof. Such modified sequences can be used to produce a mutant hmGluR subtype which differs from the receptor subtypes found in nature. Mutagenesis may be predetermined (site-specific) or random. A mutation which is not a silent mutation must not place sequences out of reading frames and preferably will not create complementary regions that could hybridize to produce secondary mRNA structures such as loops or hairpins.

The cDNA or genomic DNA encoding native or mutant hmGluR of the invention can be incorporated into vectors for further manipulation. Furthermore, the invention concerns a recombinant DNA which is a hybrid vector comprising at least one of the above mentioned DNAs.

The hybrid vectors of the invention comprise an origin of replication or an autonomously replicating sequence, one or more dominant marker sequences and, optionally, expression control sequences, signal sequences and additional restriction sites.

Preferably, the hybrid vector of the invention comprises an above described nucleic acid insert operably linked to an expression control sequence, in particular those described hereinafter.

Vectors typically perform two functions in collaboration with compatible host cells. One function is to facilitate the cloning of the nucleic acid that encodes the hmGluR subtype of the invention, i.e. to produce usable quantities of the nucleic acid (cloning vectors). The other function is to provide for replication and expression of the gene constructs in a suitable host, either by maintenance as an extrachromosomal element or by integration into the host chromosome (expression vectors). A cloning vector comprises the DNAs as described above, an origin of replication or an autonomously replicating sequence, selectable marker sequences, and optionally, signal sequences and additional restriction sites. An expression vector additionally comprises expression control sequences essential for the transcription and translation of the DNA of the invention. Thus an expression vector refers to a recombinant DNA construct, such as a plasmid, a phage, recombinant virus or other vector that, upon introduction into a suitable host cell, results in expression of the cloned DNA. Suitable expression vectors are well known in the art and include those that are replicable in eukaryotic and/or prokaryotic cells.

Most expression vectors are capable of replication in at least one class of organisms but can be transfected into another organism for expression. For example, a vector is cloned in *E. coli* and then the same vector is transfected into yeast or mammalian cells even though it is not capable of replicating independently of the host cell chromosome. DNA may also be amplified by insertion into the host genome. However, the recovery of genomic DNA encoding hmGluR is more complex than that of exogenously replicated vector because restriction enzyme digestion is required to excise hmGluR DNA. DNA can be amplified by PCR and be directly transfected into the host cells without any replication component.

Advantageously, expression and cloning vector contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

Since the amplification of the vectors is conveniently done in *E. coli,* an *E. coli* genetic marker and an *E. coli* origin of replication are advantageously included. These can be obtained from *E. coli* plasmids, such as pBR322, Bluescript vector or a pUC plasmid.

Suitable selectable markers for mammalian cells are those that enable the identification of cells competent to take up hmGluR nucleic acid, such as dihydrofolate reductase (DHFR, methotrexate resistance), thymidine kinase, or genes confering resistance to G418 or hygromycin. The mammalian cell transfectants are placed under selection pressure which only those transfectants are uniquely adapted to survive which have taken up and are expressing the marker.

Expression and cloning vectors usually contain a promoter that is recognized by the host organism and is operably linked to hmGluR nucleic acid. Such promoter may be inducible or constitutive. The promoters are operably linked to DNA encoding hmGluR by removing the promoter from the source DNA by restriction enzyme digestion and inserting the isolated promoter sequence into the vector. Both the native hmGluR promoter sequence and many heterologous promoters may be used to direct amplification and/or expression of hmGluR DNA. However, heterologous promoters are preferred, because they generally allow for greater transcription and higher yields of expressed hmGluR as compared to native hmGluR promoter.

Promoters suitable for use with prokaryotic hosts include, for example, the β-lactamase and lactose promoter systems, alkaline phosphatase, a tryptophan (trp) promoter system and hybrid promoters such as the tac promoter. Their nucleotide sequences have been published, thereby enabling the skilled worker operably to ligate them to DNA encoding hmGluR, using linkers or adaptors to supply any required restriction sites. Promoters for use in bacterial systems will also generally contain a Shine-Delgarno sequence operably linked to the DNA encoding hmGluR.

HmGluR gene transcription from vectors in mammalian host cells may be controlled by promoters compatible with the host cell systems, e.g. promoters derived from the genomes of viruses. Suitable plasmids for expression of a hmGluR subtype of the invention in eukaryotic host cells, particularly mammalian cells, are e.g. cytomegalovirus (CMV) promoter-containing vectors, RSV promoter-containing vectors and SV40 promoter-containing vectors and MMTV LTR promoter-containing vectors. Depending on the nature of their regulation, promoters may be constitutive or regulatable by experimental conditions.

Transcription of a DNA encoding a hmGluR subtype according to the invention by higher eukaryotes may be increased by inserting an enhancer sequence into the vector.

The various DNA segments of the vector DNA are operatively linked, i.e. they are contiguous and placed into a functional relationship to each other.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a manner known in the art. Suitable methods for constructing expression vectors, preparing in vitro transcripts, introducing DNA into host cells, and performing analyses for assessing hmGluR expression and function are known to those skilled in the art. Gene presence, amplification and/or expression may be measured in a sample directly, for example, by conventional Southern blotting, northern blotting to quantitate the transcription of mRNA, dot blotting (DNA or RNA analysis), in situ hybridization, using an appropriately labelled probe based on a sequence provided herein, binding assays, immunodetection and functional assays. Suitable methods include those decribed in detail in the Examples. Those skilled in the art will readily envisage how these methods may be modified, if desired.

The invention further provides host cells capable of producing a hmGluR subtype of the invention and including heterologous (foreign) DNA encoding said subtype.

The nucleic acids of the invention can be expressed in a wide variety of host cells, e.g. those mentioned above, that are transformed or transfected with an appropriate expression vector. The receptor of the invention (or a portion thereof) may also be expressed as a fusion protein. Recombinant cells can then be cultured under conditions whereby the protein(s) encoded by the DNA of the invention is (are) expressed.

Suitable prokaryotes include eubacteria, such as Gram-negative or Gram-prositive organisms, such as *E. coli,* e.g. *E. coli* K-12 strains, DH5α and HB 101, or Bacilli. Further host cells suitable for hmGluR encoding vectors include eukaryotic microbes such as filamentous fungi or yeast, e.g. *Saccharomyces cerevisiae.* Higher eukaryotic cells include insect, amphebian and vertebrate cells, particularly mammalian cells, e.g. neuroblastoma cell lines or fibroblast derived cell lines. Examples of preferred mammalian cell lines are e.g. HEK 293 cells, CHO cells, CV1 cells, BHK cells, L cells, LLCPK-1 cells, GH3 cells, L cells and COS cells. In recent years propagation of vertebrate cells in culture (tissue culture) has become a routine procedure. The host cells referred to in this application comprise cells in in vitro culture as well as cells that are within a host animal.

Suitable host cells for expression of an active recombinant hmGluR of the invention advantageously express endogenous or recombinant G-proteins. Preferred are cells producing little, if any, endogenous metabotropic glutamate receptor. DNA may be stably incorporated into the cells or may be transiently expressed according to conventional methods.

Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of hmGluR-encoding nucleic acid to form hmGluR of the invention. The precise amounts of DNA encoding hmGluR of the invention may be empirically determined and optimized for a particular cell and assay.

A DNA of the invention may also be expressed in non-human transgenic animals, particularly transgenic warm-blooded animals. Methods for producing transgenic animals, including mice, rats, rabbits, sheep and pigs, are known in the art and are disclosed, for example by Hammer et al. (Nature 315, 680–683, 1985). An expression unit including a DNA of the invention coding for a hmGluR together with appropriately positioned expression control sequences, is introduced into pronuclei of fertilized eggs. Introduction may be achieved, e.g. by microinjection. Integration of the injected DNA is detected, e.g. by blot analysis of DNA from suitable tissue samples. It is preferred that the introduced DNA be incorporated into the germ line of the animal so that it is passed to the animal's progeny. Preferably, a transgenic animal is developped by targeting a mutation to disrupt a hmGluR sequence. Such an animal is useful e.g. for studying the role of a metabotropic receptor in metabolism.

Furthermore, a knock-out animal may be developed by introducing a mutation in the hmGluR sequence, thereby generating an animal which does not express the functional hmGluR gene anymore. Such knock-out animal is useful e.g. for studying the role of metabotropic receptor in metabolism. methods for producing knock-out mice are known in the art.

Host cells are transfected or transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique, by electroporation or by lipofectin-mediated. Numerous methods of transfection are known to the skilled worker in the field. Successful transfection is generally recognized when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby hmGluR encoded by the DNA is expressed. The composition of suitable media is known to those in the art, so that they can be readily prepared. Suitable culturing media are also commercially available.

While the DNA provided herein may be expressed in any suitable host cell, e.g. those referred to above, preferred for expression of DNA encoding functional hmGluR are eukaryotic expression systems, particularly mammalian expression systems, including commercially available systems and other systems known to those of skill in the art.

Human mGluR DNA of the invention is ligated into a vector, and introduced into suitable host cells to produce transformed cell lines that express a particular hmGluR subtype of the invention, or specific combinations of subtypes. The resulting cell line can then be produced in amounts sufficient for reproducible qualitative and quantitative analysis of the effects of a receptor agonist, antagonist or allosteric modulator. Additionally, mRNA may be produced by in vitro transcription of a DNA encoding a subtype of the invention. This mRNA may be injected into *Xenopus oocytes* where the mRNA directs the synthesis of the active receptor subtype. Alternatively, the subtype-encoding DNA can be directly injected into oocytes. The transfected mammalian cells or injected oocytes may then be employed in an drug screening assay provided hereinafter. Such drugs are useful in diseases associated with pathogenesis of a hmGluR subtype of the invention. Such diseases include diseases resulting from excessive action of glutamate preferentially mediated by hmGluRs, such as stroke, epilepsy and chronic neurogenerative diseases. Particularly useful for assessing the specific interaction of compounds with specific hmGluR subtypes are stably transfected cell lines expressing a hmGluR of the invention.

Thus host cells expressing hmGluR of the invention are useful for drug screening and it is a further object of the present invention to provide a method for identifying a compound or signal which modulates the activity of hmGluR, said method comprising exposing cells containing heterologous DNA encoding hmGluR of the invention, wherein said cells produce functional hmGluR, to at least one compound or signal whose ability to modulate the activity of said hmGluR is sought to be determined, and thereafter monitoring said cells for changes caused by said modulation. Such an assay enables the identification of agonists, antagonists and allosteric modulators of a hmGluR of the invention.

In a further aspect, the invention relates to an assay for identifying compounds which modulate the activity of a hmGluR subtype of the invention, said assay comprising:

contacting cells expressing an active hmGluR subtype of the invention and containing heterologous DNA encoding said hmGluR subtype with at least one compound to be tested for its ability to modulate the activity of said receptor, and analysing cells for a difference in second messenger level or receptor activity.

In particular, the invention covers an assay for identifying compounds which modulate the activity of a hmGluR subtype of the invention, said assay comprising:

contacting cells expressing active hmGluR of the invention and containing heterologous DNA encoding said hmGluR subtype with at least one compound to be tested for its ability to modulate the activity of said receptor, and monitoring said cells for a resulting change in second messenger activity.

The result obtained in the assay is compared to an assay suitable as a negative control.

Assay methods generally require comparison to various controls. A change in receptor activity or in second messenger level is said to be induced by a test compound if such an effect does not occur in the absence of the test compound. An effect of a test compound on a receptor subtype of the invention is said to be mediated by said receptor if this effect is not observed in cells not expressing the receptor.

As used herein, a compound or signal that modulates the activity of a hmGluR of the invention refers to a compound or signal that alters the response pathway mediated by said hmGluR within a cell (as compared to the absence of said hmGluR). A response pathway is activated by an extracellular stimulus, resulting in a change in second messenger concentration or enzyme activity, or resulting in a change of the activity of a membrane-bound protein, such as a receptor or ion channel. A variety of response pathways may be utilized, including for example, the adenylate cyclase response pathway, the phospholipase C/intracellular calcium ion response pathway or coupling to an ion channel. Assays to determine adenylate cyclase activity are well known in the art, and include e.g. the assay disclosed by Nakajima et al., J. Biol. Chem. 267, 2437–2442 (1992)).

Thus cells expressing hmGluR of the invention may be employed for the identification of compounds, particularly low molecular weight molecules capable of acting as glutamate agonists or antagonists. Preferred are low molecular weight molecules of less than 1,000 Dalton. Within the context of the present invention, an agonist is understood to refer to a molecule that is capable of interacting with a receptor, thus mimicking the action of L-glutamate. In particular, a glutamate agonist is characterized by its ability to interact with a hmGluR of the invention, and thereby increasing or decreasing the stimulation of a response pathway within a cell. For example, an agonist increases or decreases a measurable parameter within the host cell, such as the concentration of a second messenger, as does the natural ligand increase or decrease said parameter. For example, in a suitable test system, wherein hmGluR of the invention is negatively coupled to adenylate cyclase, e.g. CHO or BHK cells expressing a hmGluR of the invention, such an agonist is capable of modulating the function of said hmGluR such that the intracellular concentration of cAMP is decreased.

By contrast, in situations where it is desirable to tone down the activity of hmGluR, antagonizing molecules are useful. Within the context of the present invention, an antagonist is understood to refer to a molecule that is capable of interacting with a receptor or with L-glutamate, but which does not stimulate a response pathway within a cell. In particular, glutamate antagonists are generally identified by their ability to interact with a hmGluR of the invention, and thereby reduce the ability of the natural ligand to stimulate a response pathway within a cell, e.g. by interfering with the binding of L-glutamate to a hmGluR of the invention or by inhibiting other cellular functions required for the activity of hmGluR. For example, in a suitable assay, e.g. an assay involving CHO or BHK cells expressing a hmGluR subtype of the invention, a glutamate antagonist is capable of modulating the activity of a hmGluR of the invention such that the ability of the natural ligand to decrease the intracellular cAMP concentration is weakened. Yet another alternative to achieve an antagonistic effect is to rely on overexpression of antisense hmGluR RNA. Preferred is an agonist or antagonist selectively acting on a receptor of the hmGluR4 subfamily, e.g. hmGluR4, hmGluR6 or hmGluR7. Particularly useful is an agonist or antagonist specifically modulating the activity of a particular hmGluR subtype without affecting the activity of any other subtype.

An allosteric modulator of a hmGluR of the invention interacts with the receptor protein at another site than L-glutamate, thus acting as agonist or antagonist. Therefore, the screening assays decribed herein are also useful for detecting an allosteric modulator of a receptor of the invention. For example, an allosteric modulator acting as agonist may enhance the specific interaction between a hmGluR of the invention and L-glutamate. If an allosteric modulator acts as an antagonist, it may e.g. interact with the receptor protein in such a way that binding of the agonist is functionally less effective.

An in vitro assay for a glutamate agonist or antagonist may require that a hmGluR of the invention is produced in sufficient amounts in a functional form using recombinant DNA methods. An assay is then designed to measure a functional property of the hmGluR protein, e.g. interaction with a glutamatergic ligand. Production of a hmGluR of the invention is regarded as occurring in sufficient amounts, if activity of said receptor results in a measurable response.

For example, mammalian cells, e.g. HEK293 cells, L cells, CHO-K1 cells, LLCPK-1 cells or GH3 cells (available e.g. from the American Tissue Type Culture Collection) are adapted to grow in a glutamate reduced, preferably a glutamate free, medium. A hmGluR expression plasmid, e.g. a plasmid described in the Examples, is transiently transfected into the cells, e.g. by calcium-phosphate precipitation (Ausubel, F. M., et al. (1993) Current Protocols in Molecular Biology, Greene and Wiley, USA). Cell lines stably expressing a hmGluR of the invention may be generated e.g. by lipofectin-mediated transfection with hmGluR expression plasmids and a plasmid comprising a selectable marker gene, e.g. pSV2-Neo (Southern and Berg, J. Mol. Appl. Genet. 1, 327–341 (1982)), a plasmid vector encoding the G-418 resistence gene. Cells surviving the selection are isolated and grown in the selection medium. Resistant clonal cell lines are analyzed, e.g. for immunoreactivity with subtype-specific hmGluR antibodies or by assays for hmGluR functional responses following agonist addition. Cells producing the desired hmGluR subtype are used in a method for detecting compounds binding to a hmGluR of the invention or in a method for identifying a glutamate agonist or antagonist.

In a further embodiment, the invention provides a method for identifying compounds binding to a hmGluR subtype, said method comprising employing a hmGluR subtype of the invention in a competitive binding assay. The principle underlying a competitive binding assay is generally kown in the art. Briefly, binding assays according to the invention are performed by allowing the compound to be tested for its hmGluR binding capability to compete with a known, suitably labeled, glutamatergic ligand for the binding site at the hmGluR target molecule. A suitably labeled ligand is e.g. a radioactively labeled ligand, such as [$^3$H]glutamate, or a ligand which can be detected by its optical properties, such as absorbance or fluorescence. After removing unbound ligand and test compound the amount of labeled ligand bound to hmGluR is measured. If the amount of labeled ligand is reduced in the presence of the test compound this compound is said to be bound to the target molecule. A competitive binding assay may be performed e.g. with transformed or transfected host cells expressing a hmGluR of the invention or a membraneous cellular fraction comprising a hmGluR of the invention.

Compound bound to the target hmGluR may modulate the functional properties of hmGluR and may thereby be identified as a glutamate agonist or antagonist in a functional assay.

Functional assays are used to detect a change in the functional activity of a hmGluR of the invention, i.e. to detect a functional response, e.g. as a result of the interaction of the compound to be tested with said hmGluR. A functional response is e.g. a change (difference) in the concentration of a relevant second messenger, or a change in the activity of another membrane-bound protein influenced by the receptor of the invention within cells expressing a functional hmGluR of the invention (as compared to a negative control). Those of skill in the art can readily identify an assay suitable for detecting a change in the level of an intracellular second messenger indicative of the expression of an active hmGluR (functional assay). Examples include cAMP assays (see, e.g. Nakajima et al., J. Biol. Chem. 267, 2437–2442 (1992), cGMP assays (see, e.g. Steiner et al., J. Biol. Chem. 247, 1106–1113 (1972)), phosphatidyl inositol (PI) turnover assays (Nakajima et al., J. Biol. Chem. 267, 2437–2442 (1992)), calcium ion flux assays (Ito et al., J. Neurochem. 56, 531–540 (1991)), arachidonic acid release assays (see, e.g. Felder et al., J. Biol. Chem. 264, 20356–20362 (1989)), and the like.

More specifically, according to the invention a method for detecting a glutamate agonist comprises the steps of (a) exposing a compound to a hmGluR subtype of the invention coupled to a response pathway, under conditions and for a time sufficient to allow interaction of the compound with the receptor and an associated response through the pathway, and (b) detecting an increase or decrease in the stimulation of the response pathway resulting from the interaction of the compound with the hmGluR subtype, relative to the absence of the tested compound and therefrom determining the presence of a glutamate agonist.

A method for identifying a glutamate antagonist comprises the steps of (a) exposing a compound in the presence of a known glutamate agonist to a hmGluR subtype of the invention coupled to a response pathway, under conditions and for a time sufficient to allow interaction of the agonist with the receptor and an associated response through the pathway, and (b) detecting an inhibition of the stimulation of the response pathway by the agonist resulting from the interaction of the compound with the hmGluR subtype, relative to the stimulation of the response pathway by the glutamate agonist alone and therefrom determining the presence of a glutamate antagonist. Inhibition may be detected, e.g. if the test compound competes with the glutamate agonist for the hmGluR of the invention. Compounds which may be screened utilizing such method are e.g. blocking antibodies specifically binding to the hmGluR subtype. Furthermore, such an assay is useful for the screening for compounds interacting with L-glutamate, e.g. soluble hmGluR fragment s comp rising part or all of the ligand binding domain.

Preferentially, interaction of an agonist or antagonist with a hmGluR of the invention denotes binding of the agonist or antagonist to said hmGluR.

As employed herein, conditions and times sufficient for interaction of a glutamate agonist or antagonist candidate to the receptor will vary with the source of the receptor, however, conditions generally suitable for binding occur between about 4° C. and about 40° C., preferably between about 4° C. and about 37° C., in a buffer solution between 0 and 2 M NaCl, preferably between 0 and 0.9 M NaCl, with 0.1 M NaCl being particularly preferred, and within a pH range of between 5 and 9, preferably between 6.5 and 8. Sufficient time for the binding and response will generally be between about 1 ms and about 24 h after exposure.

Within one embodiment of the present invention, the response pathway is a membrane-bound adenylate cyclase pathway, and, for an agonist, the step of detecting comprises measuring a reduction or increase, preferably a reduction, in cAMP production by the membrane-bound adenylate cyclase response pathway, relative to t he AMP production in the relevant control setup. For the purpose of the present invention, it is preferred that the reduction or increase in cAMP production be equivalent or greater than the reduction or increase induced by L-glutamate applied at a concentration corresponding to its $IC_{50}$ concentration. For an antagonist, the step of detecting comprises measuring in the presence of the antagonist a smaller L-glutamate induced decrease or increase in cAMP production by the membrane-bound adenylate cyclase response pathway, as compared to the cAMP production in the absence of the antagonist. The measurement of cAMP may be performed after cell destruction or by a cAMP sensitive molecular probe loaded into the cell, such as a fluorescent dye, which changes its properties, e.g. its fluorescent properties, upon binding of cAMP.

Cyclic AMP production may be measured using methods well known in the art, including for instance, methods described by Nakajima et al., supra, or using commercially available kits, e.g. kits comprising radiolabeled cAMP, e.g. [$^{125}$I]cAMP or [$^{3}$H]cAMP. Exemplary kits are the Scintillation Proximity Assay Kit by Amersham, which measures the production of cAMP by competition of iodinated-cAMP with cAMP antibodies, or the Cyclic AMP [$^{3}$H] Assay Kit by Amersham.

In assay systems using cells expressing receptor subtypes that are negatively coupled to the adenylate cyclase pathway, i.e. which cause a decrease in cAMP upon stimulation and an increase in cAMP upon reduction of stimulation, it is preferred to expose the cells to a compound which reversibly or irreversibly stimulates the adenylate cyclase, e.g. forskolin, or which is a phosphodiesterase inhibitor, such as isobutylmethylxanthine (IBMX), prior to addition of the (potential) receptor agonist or antagonist.

Within another embodiment of the invention, the response pathway is the PI hydrolysis/$Ca^{2+}$ mobilization pathway. Such an assay for determining the specific interaction of a test compound with a hmGluR subtype of the invention may be functionally linked to changes in the intracellular calcium ion ($Ca^{2+}$) concentration. Several methods for determining a change in the intracellular concentration of $Ca^{2+}$ are known in the art, e.g. a method involving a calcium ion sensitive fluoroscent dye, such as fura-2 (see Grynkiewisz et al., J. Biol. Chem. 260, 3440–3450, 1985), fluo-3 or Indo-1, such as the calcium fluor QuinZ method describe by Charest et al. (J. Biol. Chem. 259, 8679–8773 (1993)), or the aequorin photoprotein method described by Nakajima-Shimada (Proc. Natl Acad. Sci. USA 88, 6878–6882 (1991)). In one embodiment of the invention, intracellular calcium ion concentration is measured by microfluoremetry in recombinant cells loaded with calcium sensitive fluorescent dyes fluo-3 or fura-2. These measurements may be performed using cells grown in a coverslip allowing the use of an inverted microscope and video-imaging technologies or a fluorescence photometer to measure calcium concentrations at the single cell level. For both approaches, cells transformed with a hmGluR expressing plasmid have to be loaded with the calcium indicator. To this end, the growth medium is removed from the cells and replaced with a solution containing fura-2 or fluo-3. The cells are used for calcium measurements preferentially during the following 8h. The microfluorometry follows standard procedures.

$Ca^{2+}$ signals resulting from functional interaction of compounds with the target molecule can be transient if the compound is applied for a limited time period, e.g. via a perfusion system. Using transient application several measurements can be made with the same cells allowing for internal controls and high numbers of compounds tested.

Functional coupling of a hmGluR of the invention to $Ca^{2+}$ signaling may be achieved, e.g. in CHO cells, by various methods:

(i) coexpression of a recombinant hmGluR of the invention and a recombinant voltage-gated cation channel, activity of which is functionally linked to the activity of the hmGluR;

(ii) expression of a chimeric hmGluR receptor, which directly stimulates the PI/$Ca^{2+}$ pathway;

(iii) coexpression of a recombinant hmGluR of the invention with a recombinant $Ca^{2+}$-permeable cAMP dependent cation channel.

In other expression systems functional coupling of a hmGluR to $Ca^{2+}$ signalling may be achieved by transfection of a hmGluR of the invention if these cells naturally express (i) voltage gated Ca channels, activity of which is functionally linked to activity of mGluRs or (ii) $Ca^{2+}$-permeable cAMP dependent ion channels. For example, GH3 cells which naturally express voltage-gated Ca channels, directly allow application of $Ca^{2+}$ assays to test for hmGluR functional activity by cotransfection of hmGluRs.

Further cell-based screening assays can be designed e.g. by constructing cell lines in which the expression of a reporter protein, i.e. an easily assayable protein, such as β-galactosidase, chloramphenicol acetyltransferase (CAT) or luciferase, is dependent on the function of a hmGluR of the invention. For example, a DNA construct comprising a cAMP response element is operably linked to a DNA encoding luciferase. The resulting DNA construct comprising the enzyme DNA is stably transfected into a host cell. The host cell is then transfected with a second DNA construct containing a first DNA segment encoding a hmGluR of the invention operably linked to additional DNA segments necessary for the expression of the receptor. For example, if binding of a test compound to the hmGluR of the invention results in elevated cAMP levels, the expression of luciferase is induced or decreased, depending on the promoter chosen. The luciferase is exposed to luciferin, and the photons emitted during oxidation of luciferin by the luciferase is measured.

The drug screening assays provided herein will enable identification and design of receptor subtype-specific compounds, particularly ligands binding to the receptor protein, eventually leading to the development of a disease-specific drug. If designed for a very specific interaction with only one particular hmGluR subtype (or a predetermined selection of hmGluR subtypes) such a drug is most likely to exhibit fewer unwanted side effects than a drug identified by screening with cells that express a(n) (unknown) variety of receptor subtypes. Also, testing of a single receptor subtype of the invention or specific combinations of different receptor subtypes with a variety of potential agonists or antagonists provides additional information with respect to the function and activity of the individual subtypes and should lead to the identification and design of compounds that are capable of very specific interaction with one or more receptor subtypes.

In another embodiment the invention provides polyclonal and monoclonal antibodies generated against a hmGluR subtype of the invention. Such antibodies may useful e.g. for immunoassays including immunohistochemistry as well as diagnostic and therapeutic applications. For example, antibodies specific for the extracellular domain, or portions thereof, of a particular hmGluR subtype can be applied for blocking the endogenous hmGluR subtype.

The antibodies of the invention can be prepared according to methods well known in the art using as antigen a hmGluR subtype of the invention, a fragment thereof or a cell expressing said subtype or fragment. The antigen may represent the active or inactive form of the receptor of the invention. Antibodies may be capable of distinguishing between the active or inactive form. Factors to consider in selecting subtype fragments as antigens (either as synthetic peptide or as fusion protein) include antigenicity, accessibility (i.e. extracellular and cytoplasmic domains) and uniqueness to the particular subtype.

Particularly useful are antibodies selectively recognizing and binding to receptor subtypes of the above described subfamily without binding to a subtype of another subfamily and antibodies selectively recognizing and binding to one particular subtype without binding to any other subtype.

The antibodies of the invention can be administered to a subject in need thereof employing standard methods. One of skill in the art can readily determine dose forms, treatment regimens etc, depending on the mode of administration employed.

The invention particularly relates to the specific embodiments as described in the Examples which serve to illustrate the present invention but should not be construed as a limitation thereof.

Abbreviations: hmGluR=human metabotropic glutamate receptor, nt=nucleotide

EXAMPLE 1 cDNA Encoding hmGluR4

Human mGluR4 cDNA clones are isolated from human fetal brain and human cerebellum cDNA libraries by low stringency hybridization using a radiolabeled rat mGluR4 probe generated by PCR from rat brain cDNA.

1.1 Preparation of Poly(A)$^+$ RNA from Rat Forebrain

Adult male Sprague-Dawley rats are killed by suffocation, their forebrain is removed and immediately frozen in liquid $N_2$. Total RNA is isolated using the guanidinium thiocyanate-procedure (Chomczynski and Sacchi (1987), Anal. Biochem. 162, 156–159). Enrichment of poly(A)$^+$ RNA is achieved by affinity chromatography on oligo(dT)-cellulose according to standard procedures (Sambrook, J., Fritsch, E. F. and Maniatis, T. (1989) Molecular Cloning: A Laboratory Manual (2nd edition), Cold Spring Harbor Laboratory Press, Cold Spring Harbor, USA).

1.2 First Strand cDNA Synthesis for PCR

Poly(A)$^+$RNA (mRNA) is reverse-transcribed into DNA by Moloney Murine Leukemia Virus Reverse Transcriptase (M-MLV RT, BRL). 50 μl reactions are set up as follows: 10 μg of rat forebrain poly(A)$^+$RNA in 10 μl sterile $H_2O$ are heated to 70° C. for 10 min and then quickly chilled on ice. Then, 10 μl 5×reaction buffer (250 mM Tris-HCl pH 8.3, 375 mM KCl, 15 mM $MgCl_2$), 5 μl 0.1M dithiothreitol, 5 μl mixed dNTP (10 mM each of dATP, dCTP, dGTP, dTTP, Pharmacia), 1.25 μl oligo-$dT_{12-18}$ (2 mg/ml, Pharmacia), 2.5 μl RNAsin (40 U/μl, Promega), 12.25 μl sterile $H_2O$ and 4 μl (200 U/μl) M-MLV RT are added. The reaction is carried out at 37° C. for 60 min.

1.3 PCR Conditions for Generating the Rat mGluR4 Fragment

The oligodeoxynucleotide primers used for PCR are synthesized by the phosphoramidite method. Sequences are listed in Table 1.

TABLE 1

| |
|---|
| P1: 5'-GTCAAGGCCTCGGGCCGGGA- 3' (SEQ ID NO:17) corresponding to bp 1921–1940 of rat mGluR4 cDNA (Tanabe, et al., (1992), Neuron 8, 169–179) |
| P2: 5'-CTAGATGGCATGGTTGGTGTA-3' (SEQ ID NO:18) corresponding to bp 2788–2808 of rat mGluR4 cDNA (Tanabe, et al., (1992), Neuron 8, 169–179) |

Standard PCR-conditions for a 100 μl reaction mixture are: 30 ng of rat forebrain cDNA, 50 pmol each of primers P1 and P2, 200 μmol each of the four deoxynucleoside triphosphates dATP, dCTP, dGTP and dTTP, 10% DMSO in PCR-buffer (10 mM Tris-HCl, pH 8.3, 1.5 mM $MgCl_2$, 50 mM KCl, 10 mM β-mercaptoethanol, 0.05% Tween (w/v), 0.05% NP-40 (w/v)), and 0.5 U AmpliTaq Polymerase (Perkin Elmer Cetus). The amplification is performed using the following conditions: 30 sec denaturing at 93° C., 1 min 30 sec annealing at 56° C., and 3 min extension at 72° C., for a total of 40 cycles. Initial denaturation is carried out for 4 min at 94° C.

1.4 Subcloning of the Rat mGluR4 PCR Fragment

Restriction endonuclease digestions, use of modifying enzymes, vector preparation (dephosphorylation, gel purification), ligations, transformation of E. coli, and plasmid DNA preparations are performed according to standard procedures (Sambrook, et al. (1989), supra).

The PCR fragment (888 bp) obtained according to the procedure described in 1.3 is ligated into the SmaI site of the Bluescript SK$^+$ plasmid (Stratagene, La Jolla, USA). The fragment inserted into the Bluescript vector is sequenced from both ends using T7 and T3 primers (Stratagene, La Jolla, USA).

1.5 Preparation of a Radiolabeled Probe

20–50 ng of the PCR generated rat mGluR4 fragment are gel purified and $^{32}$P-labeled by random priming using a DNA Labeling Kit (Boehringer Mannheim).

1.6 cDNA Library Screening

About 1×10⁶ phages from a human fetal brain library (λZAPII, Stratagene, La Jolla, USA), human hippocampus (ZAP, Stratagene, La Jolla, USA), and a human cerebellum cDNA library (λZAP, Stratagene) are screened for hybridization to the rat mGluR4 fragment. Hybridization is performed in 5×SSC, 0.02% (w/v) Ficoll (Type 400), 0.02% (w/v) Polyvinylpyrrolidone, 0.1% (w/v) SDS, 50 μg/ml Herring Testis DNA. Prehybridization is carried out between 30 min to 3 hours at 58° C. Hybridization is carried out at low stringency at 58° C. overnight in the same solution containing the $^{32}$P-labeled fragment at a concentration of 1–3×10⁵ cpm/ml. Washes are done three times for 20 min each at 58° C. in 2×SSC/0.1% SDS.

Phages hybridizing to the rat mGluR4 probe are purified by a second and third round of screening under the conditions described above. The cDNA inserts harbored by the purified phages are rescued by in vivo excision using the ExAssist/SOLR system (Stratagene, La Jolla, USA).

1.7 Characterization of Isolated cDNA Clones

Several cDNA inserts are characterized by restriction enzyme mapping and DNA sequence analysis. One of these clones, cDNA cmR20 (isolated from human cerebellar library) contains an insert of approximately 3.3 kb. Sequence analysis of cmR20 indicates that it contains almost the complete coding region of human mGluR4 including a translation termination codon (nt 158 to 2739, cf. SEQ ID NO:1) as well as approximately 750 nt of 3' untranslated region. The 5' end including the translational start codon is lacking.

1.8 Isolation of the 5' End of Human mGluR4

To complete the coding region of human mGluR4 PCR reactions are carried out using human genomic DNA or first strand cDNA of human brain RNA as a template. The sense primer P3 corresponds to the 5' end of the rat mGluR4 cDNA, the antisense primer P4 to nt 440–459 of the rat mGluR4 cDNA.

TABLE 2

P3: 5'-GCGCTGCAGGCGGCCGCAGGGCCTGCTAGGGCTAGGAGCGGGGC-3' (SEQ ID NO:19)
    corresponding to nt 11–37 of rat mGluR4 CDNA
    (Tanabe, et al., (1992), Neuron 8, 169–179)
P4: 5'-GCGGAATTCCCTCCGTGCCGTCCTTCTCG-3' (SEQ ID NO:20)
    corresponding to nt 440–459 of rat mGluR4 cDNA
    (Tanabe, et al., (1992), Neuron 8, 169–179)

Additional sequences are underlined, sites for restriction enzymes are indicated in boldface.

PCR reactions for a 100 μl reaction mixture are: 400 ng of human genomic DNA, 1 μM of each primer, 2 mM of each deoxynucleoside triphosphate (dATP, dCTP, dGTP and dTTP) in PCR-buffer (10 mM Tris-HCl, pH 8.3, 1.5 mM MgCl$_2$, 50 mM KCl, and 2 U AmpliTaq Polymerase. The amplification is performed using, the following conditions: 1 min denaturation at 95° C., 1 min annealing at 56° C., and 1 min extension at 72° C., for a total of 32 cycles. Initial denaturation is carried out for 3 min at 94° C.

Products of several independent PCRs are digested with restriction enzymes PstI and EcoRI, gel purified, and ligated into the PstI/EcoRI sites of pBluescript SK (Stratagene). Subcloned fragments of several independent PCRs are analyzed by DNA sequence analysis (cR4PCR1–4). Sequence analysis reveals that clone cR4PCR2 encodes 380 nt of hmGluR4 coding region including the translation initiation codon (nt 1–380, cf. SEQ ID NO:1). cR4PCR2 overlaps at the 3' end for 223 nt with cmR20.

The complete deduced amino acid sequence of the hmGluR4 protein is set forth in SEQ ID NO:2.

EXAMPLE 2 cDNA Clones Encoding hmGluR7

Screening of human fetal brain and human cerebellum cDNA libraries by low-stringency hybridization using radio-labeled rat mGluR4 fragment (as described in 1.5 and 1.6) allows the isolation of cDNA clones that identify the human metabotropic glutamate receptor subtype mGluR7. Characterization of cDNA clones by DNA sequence analysis reveals that isolated cDNAs represent at least two apparent splice variants of human mGluR7 mRNA.

cDNA cmR2 (isolated from human fetal brain cDNA library) has a size of 3804 nt. Clone cmR2 contains 2604 nt of hmGluR7 coding sequence including a translation termination codon followed by 1200 nt of 3' untranslated sequence (cf. SEQ ID NO:3).

cDNA cmR3 (isolated from human hippocampus cDNA library) has a size of 1399 nt (SEQ ID NO:5). cmR3 contains 270 nt of the hmGluR7 3' end coding region including a translation termination stop codon (the deduced amino acid sequence is set forth in SEQ ID NO:6) followed by 1129 nt of 3' untranslated sequence. The sequence of cmR3 is completely contained in cmR2 but differs from cmR2 by deletion of the 92 nucleotides extending from the nt at position 2534 to the nt at position 2625 in SEQ ID NO:3). This apparent splice variant of hmGluR7 generates a different 3' end of the deduced hmGluR7 amino acid sequence.

cDNA cmR5 (isolated from human fetal brain cDNA library) has a size of 1588 nt (SEQ ID NO:7). cDNA cmR5 overlaps 1424 nt with cDNA cmR2. It diverges at the 3' end exactly at the position of the 92-nt-insertion/deletion of cmR2/cmR3. Additional 164 nt of cmR5 either encode intronic sequences as indicated by presence of a conserved splice donor sequence immediately following the site of cmR5 and cmR2/cmR3 sequence divergence, or represent a third splice variant.

The 5' end coding region of hmGluR7 DNA missing in cDNA clones cmR2, cmR3, and cmR5, is isolated by a combination of genomic library screening and PCR techniques. A Lamda-Fix genomic library (Stratagene) is screened with a EcoRI/SmaI restriction fragment comprising nt 1–1304 of cDNA cmR2 under high stringency hybridization conditions as described in Sambrook, et al. (1989), supra. Lambda clones hybridizing to the 5' end of cDNA clone cmR2 are purified and analyzed by restriction analyses and DNA sequencing. The complete 5' end of the coding region of human mGluR7 including the ATG translation initiation codon is amplified by PCR from human brain cDNA using primer sequences derived from cloned genomic fragments. The PCR fragments has a size of 557 nt. It is designated as cR7PCR1 and depicted as SEQ ID NO:9. The deduced amino acid sequence is set forth in SEQ ID NO:10. cR7PCR1 overlaps at the 3' end with cmR2 for 392 nt.

The DNA sequences coding for the complete hmGluR7a and b proteins are set forth in SEQ ID NOs:11 and 13, respectively. The deduced amino acid sequences are given in SEQ ID NOs:12 and 14, respectively. Comparison of the deduced amino acid sequences reveals approximately 70% sequence identity to the hmGluR4 subtype of Example 1.

EXAMPLE 3
cDNA Encoding Partial hmGluR6

A single cDNA clone, cmR1, with an insert of 1.0 kb is isolated from a human hippocampus library by low stringency hybridization using the hmGluR fragment as described above in example 1.5 and 1.6. Approximately 630 nucleotides are homologous to human mGluR4. Additional sequences at the 5' and 3' end of cmR1 apparently encode intronic sequences as indicated by the presence of putative splice donor and splice acceptor site sequences. cDNA cmR1 identifies a portion of the human metabotropic glutamate receptor subtype hmGluR6 (SEQ ID NOs. 15). The deduced amino acid sequence is set forth in SEQ ID NO:16.

The complete coding region of hmGluR6 is isolated by screening of cDNA and genomic libraries under high stringency conditions with cDNA cmR1 as a probe. Comparison of the deduced amino acid sequences reveals approximately 70% sequence identity to hmGluR4 of Example 1.

EXAMPLE 4
Expression of hmGluR cDNAs in Mammalian Cells
4.1 Receptor Expression Plasmids cDNAs encoding the above full-length hmGluR4, hmGluR6, and hmGluR7 proteins are generated from cDNA fragments and ligated into mammalian expression vectors based on constitutive promoters (CMV, SV40, RSV) or inducible promoters. Examples are pBK-CMV (Stratagene), pBK-RSV (Stratagene), pCMV-T7 (Sibia, Inc.) and pICP4 (Novagen, USA).

The full-length cDNA encoding the hmGluR4 subtype is incorporated into the mammalian expression vector pBK-CMV by ligating the hmGluR4 5' end fragment (clone cR4PCR2) with cDNA cmR20 at the unique XhoI site that is located at nt 346–351 of the hmGluR4 cDNA. Specifically, plasmid pBK-CMV-hmGluR4 is generated by three-way-ligation of the NotI/XhoI fragment of cR4PCR2, the XhoI/NotI fragment of cDNA cmR20 and the NotI digested vector pBK-CMV. Plasmid pCMV-T7-hmGluR4 is generated by three-way-ligation of the PstI/XhoI fragment of cR4PCR4, the XhoI/EcoRI fragment of cmR20 and the PstI/EcoRI digested vector pCMV-T7-2. Both expression constructs contain the complete coding region of the hmGluR4 as well as approximately 750 nt of 3' untranslated sequences.

Full-length cDNAs representing the two hmGluR7 splice variants, designated hmGluR7a (SEQ ID NO:12) and hmGluR7b SEQ ID NO:14), are incorporated in pCMV-T7-2 (SIBIA Inc.) using the overlapping cDNA clones cmR2, cmR3 and hcR7PCR1. A full-length hmGluR7b expression construct, designated pCMV-T7-hmGluR7b, is prepared by three-way-ligation of the PstV/BsaI fragment of hcR7PCR 1, the BsaV/EagI fragment of cmR2 and the PstI/NotI of pCMV-T7-2. Plasmid pCMV-T7-hmGluR7b contains the complete coding region of hmGluR7b and 191 nt of 3' untranslated sequences. To construct a full-length hmGluR7a expression construct, designated pCMV-T7-hmGluR7a, a 370 bp HindIII/EagI fragment of cmR2 is exchanged with the corresponding fragment of cmR3. The BsaI/EagI fragment of the resulting clone is used for a three-way-ligation as describe above.

Plasmid pBK-CMV-hmGluR6 is generated analogously using conventional techniques (Sambrook et al. supra).
4.2 Transfection of Mammalian Cells Mammalian cells (e.g. CHO-K1, GH3; American Tissue Type Culture Collection) are adapted to grow in glutamate free medium (Dulbecco's modified Eagle's medium lacking L-glutamate and containing a reduced concentration of 2 mM L-glutamine, supplemented with 0.046 mg/ml proline and 10% dialyzed fetal bovine serum, Gibco-BRL). HmGluR expression plasmids are transiently transfected into the cells by calcium-phophate precipitation (Ausubel, F. M., et al. (1993) Current Protocols in Molecular Biology, Greene and Wiley, USA).

Cell lines stably expressing hmGluRs are generated by lipofectin-mediated transfection (Gibco-BRL) of CHO-KL cells with hmGluR expression plasmids and pSV2-Neo (Southern and Berg, 1982), a plasmid vector encoding the G-418 resistence gene. Cells are grown for 48 hours prior to the addition of 1 mg/ml G-418 sulfate (Geneticin, Gibco). Medium is replaced every two to three days. Cells surviving the G-418 selection are isolated and grown in the selection medium. 32 G-418 resistant clonal cell lines are analyzed six to eight weeks after the initial transfection for hmGluR protein expression by immunoreactivity with the anti-hmGluR7 antibody (immunodetection, cf. 4.3, infra) and functional responses following agonist addition via cAMP radioimmunoassay (cf. 5.1, infra).

Likewise, the hmGluR expression constructs pBK-CMV-hmGluR4, pCMV-T7-hmGluR4, pCMV-T7-hmGluR7b and pCMV-T7-hmGluR7a are transiently and stably expressed in mammalian cells (CV 1, CHO, HEK293, COS) according to standard procedures (Ausubel, F. M., et al. (1993) Current Protocols in Molecular Biology, Greene and Wiley, USA). The transfected cells are analyzed for hmGluR expression by various assays: [$^3$H]-glutamate binding studies, immunocytochemistry using hmGluR subtype specific antibodies, and assays detecting a change in the intracellular concentration of cAMP ([cAMP]).
4.3 Immunodetection of hmGluR Protein Expression with Subtype-Specific hmGluR Antibodies HmGluR protein expression is analyzed by immunocytochemistry with subtype-specific hmGluR antibodies (see Example 7). 1 to 3 days after transfection cells are washed twice with phosphate buffered saline (PBS), fixed with PBS/4% paraformaldehyde for 10 min and washed with PBS. Cells are permeabilized with PBS/0.4% Triton X-100, followed by washing with PBS/10 mM glycine, and PBS. Cells are blocked with PBSTB (1×PBS/0.1% Triton X-100/1% BSA) for 1 h and subsequently incubated with immunopurified hmGluR antiserum (0.5–2.0 µg/ml in PBSTB) for 1 h. After three washes with PBS, cells are incubated for 1 h with alkaline peroxidase conjugated goat anti-rabbit IgG (1:200 in PBSTB; Jackson Immuno Research). Cells are washed three times with PBS and immunoreactivity is detected with 0.4 mg/ml naphtolphosphate (Biorad)/1 mg/ml Fast Red (Biorad)/10 mM Levamisole (Sigma)/100 mM Tris/HCl pH 8.8/100 mM NaCl/50 mM MgCl$_2$. The staining reaction is stopped after 15 min by subsequent washing with PBS. 2 to 4 cell lines, each homogenously expressing hmGluR4, hmGluR6 or hmGluR7, are identified by immunostaining.

EXAMPLE 5
Use of Stable Cell Lines Expressing hmGluRs for the Screening of Modulators of Receptor Activity Stable cell lines expressing hmGluR4, hmGluR6 and hmGluR7 are used to screen for agonists, antagonists and allosteric modulators. Such compounds are identified by binding studies employing [$^3$H]glutamate and/or measurement of changes in intracellular second messenger levels ([cAMP], [Ca$^{2+}$]).
5.1 cAMP Radioimmunoassay Ligand binding and agonist-induced depression of forskolin stimulated cAMP accumulation (changes in the intracellular cAMP concentration) are analyzed by cAMP radioimmunoassay (Amersham). Cells are seeded in 12-well plates at a density of 0.5–2.0×10$^5$ cells per well and grown for 2 to 4 days until a confluent layer of cells is obtained. Cells are washed twice with PBS and incubated for 20 min in PBS containing 1 mM 3-isobutyl-1-methylxanthine (IBMX). Cells are incubated with fresh PBS containing 10 µM forskolin, 1 mM IBMX and a known hmGluR agonist for 20 min. The agonistic effect is stopped and cAMP produced by the cells is released by adding 1 ml of ethanol-water-HCl mix (100 ml of ethanol, 50 ml of water, 1 ml of 1 M HCl) after having aspirated the drug containing medium. cAMP levels are determined by a cAMP radioimmunoassay involving [$^3$H] cAMP (Amersham).

HmGluR subtypes 4, 6 and 7 are negatively coupled to adenylate cyclase when expressed in CHO cells. Agonist binding leads to an inhibition of forskolin induced cAMP accumulation. All subtypes are AP-4 sensitive, meaning that AP 4 has an agonistic effect in a concentration less than 1 mM.

5.2 Measurement of Intracellular [Ca$^{2+}$]

Cells transformed with one of the above expression plasmids are loaded with a calcium sensitive fluorescent dye such as fura-2 or fluro-3. To achieve this cells are plated in single wells, single wells containing a coverslip, or 96-well plates and grown for 1 to 5 days until a 50–100% confluent layer of cells is obtained. Wells are washed three times with a balance salt solution (BBS) and incubated for 1 h in BBS followed by three additional washings with BBS. Then cells are incubated for 20 to 60 min in a solution containing 50 µg fura-2-AM (or fluro3-AM) (Molecular Probes, Inc.) 4.99 ml BBS, 75 µl DMSO and 6.25 µg Pluronic (Molecular Probes, Inc). The cells are washed 3 times with BBS containing 2 mg/ml bovine albumin followed by three washes in BBS. After allowing recovery of the cells for at least 10 min they are used for microfluorometric measurements of [Ca$^{2+}$].

Cells are transferred to an apparatus for fluometry such as an inverted microscope, a spectrofluometer of a fluorescence reader. Fluorescence of the calcium indicator (e.g. fura-2 or fluo-3) is induced by illumination with light of a wavelength covered by the excitation spectrum of the dye (fura-2: 340/380 nm, fluo-3 3 480 nm). An increase in intracellular free claciom ion concentration is monitored as an increase of fura-2 or fluo-3 fluorescence excited at 340 nm and 480 nm, respectively, or a decrease of fura-2 fluorescence excited at 380 nm.

As a positive control L-glutamate is applied at a concentration corresponding to its EC$_{50}$ value onto the cells, thereby inducing a measurable increase in the intracellular calcium ion concentration. A test compound is said to be an agonist if it induces a Ca$^{2+}$ signal comparable to that induced by glutamate. A test compound is said to be an antagonist if the glutamate induced calcium signal is smaller in the presence of the test compound than in the absence of the test compound.

EXAMPLE 6

Chimeric hmGluR4, 6 and 7 Receptors

Intracellular domains of mGluR1, particularly the second intracellular loop (i2) and the C-terminal region, have been shown to be critical for binding of G-proteins, which activate the phospholipase C/Ca$^{2+}$ signaling pathway, without changing the pharmacological profile of the receptor (Pin et al., EMBO J. 13, 342–348, (1994)). Conventional PCR mutagenesis techniques are used to exchange intracellular domains of hmGluRs 4,6, and 7 with corresponding domains of hmGluR1. Stable CHO cell lines are generated with hmGluR4/1, 6/1 and 7/1 chimeric expression constructs allowing to analyze the influence of modulators of receptor activity (hmGluRs 4,6,7) using Ca$^{2+}$-dependent assays. In the following, we describe the generation of a chimeric hmGluR7/1 receptor. Expression constructs with chimeric hmGluR4/1 and hmGluR6/1 are generated using analogous cloning and PCR techniques.

(i) The expression construct pCMV-hmGluR7b is digested with EagI, thereby releasing the complete cDNA insert. The cDNA is cloned into the NotI site of pBluescript-Not, a derivative of pBluescript II (Stratagene) where the polylinker sequences between the unique KpnI and NotI sites are deleted. The resulting clone is designated as pBluescript-Not-hmGluR7.

(ii) The transmembrane region of hmGluR1 is cloned by PCR using primers derived from Masu et al., 1991, supra. The oligonucleotide with the sequence

5'-TATCTTGAGTGGAGTGACATAG-3' (SEQ ID NO:21)

(corresponding to nt 1753 to 1774 of the Masu sequence) is used as sense primer. The antisense primer has the sequence

5'-ACTGCGGACGTTCCTCTCAGG-3' (SEQ ID NO:22)

corresponding to nt 2524 to 2544 of the Masu sequence. The C-terminal end of splice variants 1a, 1b and 1c is cleaved by PCR using primers derived from Masu et al., 1991, Tanabe et al., 1992, supra, and Pin et al., 1992 (Proc. Natl. Acad. Sci, USA, 89, 10331–10335 (1992)), respectively. The oligonucleotide having the sequence

5'-AAACCTGAGAGGAACGTCCGCAG-3' (SEQ ID NO:23)

(corresponding to nt 2521 to nt 2543 of the Masu sequence) is used as sense primer. The oligonucleotides having the sequences 5'-CTACAGGGTGGAAGAGCTTTGCTT-3' SEQ ID NO:24 corresponding to nt 3577 to 3600 of the Masu sequence, 5'-TCAAAGCTGCGCATGTGCCGACGG-3' SEQ ID NO:25 corresponding to nt 2698 to 2721 of the Tanabe sequence, and 5'-TCAATAGACAGTGTTTTGGCGGTC-3' SEQ ID NO:26 corresponding to nt 2671 to 2694 of the Pin sequence are used as antisense primers for hmGluR1a, 1b and 1c, respectively.

The PCR fragment is cloned into pBluescript II and sequenced completely.

(iii) A chimeric cDNA fragment wherein the i2-loop of hmGluR7a or hmGluR7b (nt 2035 to 2106 of SEQ IDs 11 and 13, respectively) is replaced with the corresponding sequences of hmGluR1 is generated by PCR (as described in Pin et al., 1994, supra). The fragment is digested with SmaI and BglII which cut at unique restriction sites flanking the i2-loop. The chimeric SmaI/BglII fragment is exchanged for the SmaI/BglII fragments is pBluescript-Not-mGluR7.

(iv) Additional replacement of the C-terminal domain of hmGluR7b or hmGluR7a with the corresponding sequences of the above mentioned hmGluR1 splice variants is achieved by using the unique restriction sites BglII and SacII flanking the C-terminal end of hmGluR7.

(v) The resulting chimeric hmGluR7/hmGluR1 cDNAs are sequenced and digested with EagI, thereby releasing the complete cDNAs from pBluescript-Not. For stable expression in CHO cells, the chimeric cDNAs are cloned into the unique NotI site of the mammalian expression vector pCMV-T7-2.

EXAMPLE 7
Generation and Application of Anti-hmGluR Antibodies

Peptides corresponding to the deduced C-terminal amino acid sequences of hmGluR4 and hmGluR7 are synthesized and coupled to ovalbumin or Tentagel. Polyclonal antisera are raised in rabbits. Human mGluR specific antibodies are purified from the antisera by immunoaffinity chromatography on peptide columns. The hmGluR specific antibodies are characterized by ELISA and immunoblotting with glutathione-S-transferase/hmGluR fusion proteins (produced in *E. coli*) or human brain extracts. Antibodies specific for hmGluR4 and hmGluR7, respectively, are used to detect hmGluR receptors in transfected cells and to analyze the cellular and subcellular expression pattern of the hmGluR receptor proteins in tissue sections of human brain material. Antibodies are raised against different hmGluR-specific peptides consisting of 20 amino acids and fusion proteins expressed in *E.coli*. Peptides are synthesized by solid-phase synthesis, coupled to keyhole limpit hemocyanin (KLH) or ovalbumin with glutaraldehyde. PCR fragments containing the entire putative intracellular C-terminal fragment of hmGluRs are cloned as BamHI/EcoRI fragments into the *E. coli* expression plasmid pGEX-2T (Guan and Dixon, Analytical Biochemistry 192, 262–267 (1991)) generating glutathione-S-transferase(GST)/hmGluR fusion genes. *E. coli* DH5a cells (Gibco-BRL) carrying expression plasmids with GST/hmGluR fusion genes are grown overnight at 37° C. in LB medium/100 mg/ml ampicillin. The cultures are diluted 1:30 in LB and grown for 2 h at 30° C. Expression of fusion proteins is induced by treatment with 0.1 mM isopropyl-b-D-thiogalactopyranoside for 3 h at 30° C. Cells are harvested by centrifugation at 5,000×g. The fusion protein is isolated using glutathione affinity chromatography.

Deposition Data

The following plasmids were deposited with the Deutsche Sammlung von Mikroorganismen und Zellkulturen GmbH (DSM), Mascheroder Weg 1b, D-38124 Braunschweig on Sep. 13, 1993:

Plasmid cmR1; accession no. DSM 8549
Plasmid cmR2; accession no. DSM 8550

What is claimed is:

1. A purified human metabotropic glutamate receptor comprising the amino acid sequence set forth in SEQ ID NO:2.

2. An isolated composition which comprises:
   (a) a receptor of claim 1 and
   (b) one or more chemical entities,
   wherein said one or more chemical entities is covalently bonded to or adsorptively associated with said receptor of claim 1.

3. Process for the production of a receptor according to claim 1 which comprises culturing a suitable host cell transformed with a hybrid vector comprising an expression cassette comprising a promoter and a DNA coding for a receptor according to claim 1 wherein the DNA is controlled by said promoter; expressing the receptor according to claim 1 in said host cell; and isolating the receptor.

4. An isolated nucleic acid comprising a nucleic acid sequence coding for the amino acid sequence set forth in SEQ ID NO:2.

5. An isolated nucleic acid according to claim 4, wherein the nucleic acid is a DNA.

6. A process for the preparation of a nucleic acid according to claim 5 which comprises:
   chemically synthesizing said nucleic acid; or
   incorporating said nucleic acid into a hybrid vector comprising an origin of replication and replicating said vector in a suitable host organism; or
   amplifying said nucleic acid by polymerase chain reaction; and
   isolating said nucleic acid.

7. A DNA according to claim 5 which is a hybrid vector.

8. An isolated host cell comprising the DNA of claim 5.

9. An isolated eukaryotic host cell comprising the DNA of claim 5, an mRNA transcribed from the DNA of claim 5, and a protein translated from said mRNA.

10. An isolated host cell according to claim 8 which is a mammalian cell.

11. A process for the preparation of an isolated host cell comprising a DNA encoding the receptor of claim 1, wherein said process comprises transfection or transformation of the isolated host cell with a hybrid vector comprising a DNA encoding said receptor.

12. An assay for identifying compounds which modulate the activity of a hmGluR receptor according to claim 1 comprising:
   contacting cells expressing DNA encoding said hmGluR receptor according to claim 1 with a compound to be tested for its ability to modulate the activity of said receptor under conditions appropriate for binding to said receptor; and subsequently
   monitoring said cells for a resulting change in second messenger activity;
   wherein a difference in the second messenger activity of the cell in the presence compared to the absence of said compound indicates that the compound modulates activity of the receptor.

13. A method for identifying an agonist or an allosteric modulator having agonistic activity of a hmGluR receptor according to claim 1 comprising the steps of (a) exposing a test compound to a hmGluR receptor of claim 1 coupled to a response pathway, under conditions and for a time sufficient to allow (i) interaction of the test compound with the receptor and (ii) stimulation of the activity of the response pathway, and (b) detecting a stimulation in the activity of the response pathway resulting from the interaction of the test compound with the hmGluR receptor, relative to the activity of the response pathway in the absence of the test compound, wherein detection of a stimulation of the activity of the response pathway relative to the activity of the response pathway in the absence of the tested compound indicates that the test compound is an agonist or an allosteric modulator having agonist-like activity of the receptor.

14. A method for identifying an antagonist or an allosteric modulator having antagonistic activity of a hmGluR receptor according to claim 1 comprising the steps of (a) exposing a test compound in the presence of a known glutamate agonist to a hmGluR receptor of claim 1 coupled to a response pathway, under conditions and for a time sufficient to allow (i) interaction of the agonist with the receptor and (ii) stimulation of the activity of the response pathway by the agonist, and (b) detecting an inhibition of the stimulation of the activity of the response pathway by the agonist resulting from the interaction of the test compound with the hmGluR receptor, relative to the stimulation of the activity of the response pathway induced by the glutamate agonist alone, wherein detection of an inhibition in the stimulation of the activity of the response pathway indicates that the test compound is an antagonist or an allosteric modulator having antagonist-like activity of the receptor.

15. A fusion protein comprising a receptor according to claim 1.

16. A purified protein according to claim 1 consisting of the amino acid sequence set forth in SEQ ID NO:2.

17. The composition of claim 2, wherein said chemical entity is selected from the group consisting of acyl moieties, cell membranes, polypeptides, sugar molecules, alkyl groups, amino groups, radioactive moieties, and fluorescent moieties.

18. The nucleic acid of claim 4 wherein said nucleic acid sequence comprises SEQ ID NO:1.

* * * * *

UNITED STATES PATENT AND TRADEMARK OFFICE
CERTIFICATE OF CORRECTION

PATENT NO.   : 6,228,610 B1                                                      Page 1 of 1
DATED        : May 8, 2001
INVENTOR(S)  : Flor et al.

It is certified that error appears in the above-identified patent and that said Letters Patent is hereby corrected as shown below:

<u>Title page,</u>
Item [30], Foreign Application Priority Data; the second priority foreign application should read:
-- Aug. 19, 1994         (GB)…………………..9416553 --

Signed and Sealed this

First Day of July, 2003

JAMES E. ROGAN
*Director of the United States Patent and Trademark Office*

SEQUENCE LISTING

```
<160> NUMBER OF SEQ ID NOS: 26

<210> SEQ ID NO 1
<211> LENGTH: 2736
<212> TYPE: DNA
<213> ORGANISM: Homo sapiens
<220> FEATURE:
<221> NAME/KEY: CDS
<222> LOCATION: (1)..(2736)

<400> SEQUENCE: 1 atg cct ggg aag aga ggc ttg ggc tgg tgg tgg gcc cgg ctg ccc ctt      48
Met Pro Gly Lys Arg Gly Leu Gly Trp Trp Trp Ala Arg Leu Pro Leu
 1               5                  10                  15 tgc ctg ctc ctc agc ctt tac ggc ccc tgg atg cct tcc tcc ctg gga      96
Cys Leu Leu Leu Ser Leu Tyr Gly Pro Trp Met Pro Ser Ser Leu Gly
                20                  25                  30 aag ccc aaa ggc cac cct cac atg aat tcc atc cgc ata gat ggg gac     144
Lys Pro Lys Gly His Pro His Met Asn Ser Ile Arg Ile Asp Gly Asp
            35                  40                  45 atc aca ctg gga ggc ctg ttc ccg gtg cat ggc cgg ggc tca gag ggc     192
Ile Thr Leu Gly Gly Leu Phe Pro Val His Gly Arg Gly Ser Glu Gly
        50                  55                  60 aag ccc tgt gga gaa ctt aag aag gaa aag ggc atc cac cgg ctg gag     240
Lys Pro Cys Gly Glu Leu Lys Lys Glu Lys Gly Ile His Arg Leu Glu
 65                  70                  75                  80 gcc atg ctg ttc gcc ctg gat cgc atc aac aac gac ccg gac ctg ctg     288
Ala Met Leu Phe Ala Leu Asp Arg Ile Asn Asn Asp Pro Asp Leu Leu
                85                  90                  95 cct aac atc acg ctg ggc gcc cgc att ctg gac acc tgc tcc agg gac     336
Pro Asn Ile Thr Leu Gly Ala Arg Ile Leu Asp Thr Cys Ser Arg Asp
            100                 105                 110 acc cat gcc ctc gag cag tcg ctg acc ttt gtg cag gcg ctc atc gag     384
Thr His Ala Leu Glu Gln Ser Leu Thr Phe Val Gln Ala Leu Ile Glu
        115                 120                 125 aag gat ggc aca gag gtc cgc tgt ggc agt ggc ggc cca ccc atc atc     432
Lys Asp Gly Thr Glu Val Arg Cys Gly Ser Gly Gly Pro Pro Ile Ile
    130                 135                 140 acc aag cct gaa cgt gtg gtg ggt gtc atc ggt gct tca ggg agc tcg     480
```

```
                                                              -continued

Thr Lys Pro Glu Arg Val Val Gly Val Ile Gly Ala Ser Gly Ser Ser
145                 150                 155                 160 gtc tcc atc atg gtg gcc aac atc ctt cgc ctc ttc aag ata ccc cag    528
Val Ser Ile Met Val Ala Asn Ile Leu Arg Leu Phe Lys Ile Pro Gln
                165                 170                 175 atc agc tac gcc tcc aca gcg cca gac ctg agt gac aac agc cgc tac    576
Ile Ser Tyr Ala Ser Thr Ala Pro Asp Leu Ser Asp Asn Ser Arg Tyr
            180                 185                 190 gac ttc ttc tcc cgc gtg gtg ccc tcg gac acg tac cag gcc cag gcc    624
Asp Phe Phe Ser Arg Val Val Pro Ser Asp Thr Tyr Gln Ala Gln Ala
        195                 200                 205 atg gtg gac atc gtc cgt gcc ctc aag tgg aac tat gtg tcc aca gtg    672
Met Val Asp Ile Val Arg Ala Leu Lys Trp Asn Tyr Val Ser Thr Val
    210                 215                 220 gcc tcg gag ggc agc tat ggt gag agc ggt gtg gag gcc ttc atc cag    720
Ala Ser Glu Gly Ser Tyr Gly Glu Ser Gly Val Glu Ala Phe Ile Gln
225                 230                 235                 240 aag tcc cgt gag gac ggg ggc gtg tgc atc gcc cag tcg gtg aag ata    768
Lys Ser Arg Glu Asp Gly Gly Val Cys Ile Ala Gln Ser Val Lys Ile
                245                 250                 255 cca cgg gag ccc aag gca ggc gag ttc gac aag atc atc cgc cgc ctc    816
Pro Arg Glu Pro Lys Ala Gly Glu Phe Asp Lys Ile Ile Arg Arg Leu
            260                 265                 270 ctg gag act tcg aac gcc agg gca gtc atc atc ttt gcc aac gag gat    864
Leu Glu Thr Ser Asn Ala Arg Ala Val Ile Ile Phe Ala Asn Glu Asp
        275                 280                 285 gac atc agg cgt gtg ctg gag gca gca cga agg gcc aac cag aca ggc    912
Asp Ile Arg Arg Val Leu Glu Ala Ala Arg Arg Ala Asn Gln Thr Gly
    290                 295                 300 cat ttc ttc tgg atg ggc tct gac agc tgg ggc tcc aag att gca cct    960
His Phe Phe Trp Met Gly Ser Asp Ser Trp Gly Ser Lys Ile Ala Pro
305                 310                 315                 320 gtg ctg cac ctg gag gag gtg gct gag ggt gct gtc acg atc ctc ccc   1008
Val Leu His Leu Glu Glu Val Ala Glu Gly Ala Val Thr Ile Leu Pro
                325                 330                 335 aag agg atg tcc gta cga ggc ttc gac cgc tac ttc tcc agc cgc acg   1056
Lys Arg Met Ser Val Arg Gly Phe Asp Arg Tyr Phe Ser Ser Arg Thr
            340                 345                 350 ctg gac aac aac cgg cgc aac atc tgg ttt gcc gag ttc tgg gag gac   1104
Leu Asp Asn Asn Arg Arg Asn Ile Trp Phe Ala Glu Phe Trp Glu Asp
        355                 360                 365 aac ttc cac tgc aag ctg agc cgc cac gcc ctc aag aag ggc agc cac   1152
Asn Phe His Cys Lys Leu Ser Arg His Ala Leu Lys Lys Gly Ser His
    370                 375                 380 gtc aag aag tgc acc aac cgt gag cga att ggg cag gat tca gct tat   1200
Val Lys Lys Cys Thr Asn Arg Glu Arg Ile Gly Gln Asp Ser Ala Tyr
385                 390                 395                 400 gag cag gag ggg aag gtg cag ttt gtg atc gat gcc gtg tac gcc atg   1248
Glu Gln Glu Gly Lys Val Gln Phe Val Ile Asp Ala Val Tyr Ala Met
                405                 410                 415 ggc cac gcg ctg cac gcc atg cac cgt gac ctg tgt ccc ggc cgc gtg   1296
Gly His Ala Leu His Ala Met His Arg Asp Leu Cys Pro Gly Arg Val
            420                 425                 430 ggg ctc tgc ccg cgc atg gac cct gta gat ggc acc cag ctg ctt aag   1344
Gly Leu Cys Pro Arg Met Asp Pro Val Asp Gly Thr Gln Leu Leu Lys
        435                 440                 445 tac atc cga aac gtc aac ttc tca ggc atc gca ggg aac cct gtg acc   1392
Tyr Ile Arg Asn Val Asn Phe Ser Gly Ile Ala Gly Asn Pro Val Thr
    450                 455                 460
```

```
                                                        -continued
ttc aat gag aat gga gat gcg cct ggg cgc tat gac atc tac caa tac      1440
Phe Asn Glu Asn Gly Asp Ala Pro Gly Arg Tyr Asp Ile Tyr Gln Tyr
465                 470                 475                 480 cag ctg cgc aac gat tct gcc gag tac aag gtc att ggc tcc tgg act      1488
Gln Leu Arg Asn Asp Ser Ala Glu Tyr Lys Val Ile Gly Ser Trp Thr
                485                 490                 495 gac cac ctg cac ctt aga ata gag cgg atg cac tgg ccg ggg agc ggg      1536
Asp His Leu His Leu Arg Ile Glu Arg Met His Trp Pro Gly Ser Gly
            500                 505                 510 cag cag ctg ccc cgc tcc atc tgc agc ctg ccc tgc caa ccg ggt gag      1584
Gln Gln Leu Pro Arg Ser Ile Cys Ser Leu Pro Cys Gln Pro Gly Glu
        515                 520                 525 cgg aag aag aca gtg aag ggc atg cct tgc tgc tgg cac tgc gag cct      1632
Arg Lys Lys Thr Val Lys Gly Met Pro Cys Cys Trp His Cys Glu Pro
    530                 535                 540 tgc aca ggg tac cag tac cag gtg gac cgc tac acc tgt aag acg tgt      1680
Cys Thr Gly Tyr Gln Tyr Gln Val Asp Arg Tyr Thr Cys Lys Thr Cys
545                 550                 555                 560 ccc tat gac atg cgg ccc aca gag aac cgc acg ggc tgc cgg ccc atc      1728
Pro Tyr Asp Met Arg Pro Thr Glu Asn Arg Thr Gly Cys Arg Pro Ile
                565                 570                 575 ccc atc atc aag ctt gag tgg ggc tcg ccc tgg gcc gtg ctg ccc ctc      1776
Pro Ile Ile Lys Leu Glu Trp Gly Ser Pro Trp Ala Val Leu Pro Leu
            580                 585                 590 ttc ctg gcc gtg gtg ggc atc gct gcc acg ttg ttc gtg gtg atc acc      1824
Phe Leu Ala Val Val Gly Ile Ala Ala Thr Leu Phe Val Val Ile Thr
        595                 600                 605 ttt gtg cgc tac aac gac acg ccc atc gtc aag gcc tcg ggc cgt gaa      1872
Phe Val Arg Tyr Asn Asp Thr Pro Ile Val Lys Ala Ser Gly Arg Glu
    610                 615                 620 ctg agc tac gtg ctg ctg gca ggc atc ttc ctg tgc tat gcc acc acc      1920
Leu Ser Tyr Val Leu Leu Ala Gly Ile Phe Leu Cys Tyr Ala Thr Thr
625                 630                 635                 640 ttc ctc atg atc gct gag ccc gac ctt ggc acc tgc tcg ctg cgc cga      1968
Phe Leu Met Ile Ala Glu Pro Asp Leu Gly Thr Cys Ser Leu Arg Arg
                645                 650                 655 atc ttc ctg gga cta ggg atg agc atc agc tat gca gcc ctg ctc acc      2016
Ile Phe Leu Gly Leu Gly Met Ser Ile Ser Tyr Ala Ala Leu Leu Thr
            660                 665                 670 aag acc aac cgc atc tac cgc atc ttc gag cag ggc aag cgc tcg gtc      2064
Lys Thr Asn Arg Ile Tyr Arg Ile Phe Glu Gln Gly Lys Arg Ser Val
        675                 680                 685 agt gcc cca cgc ttc atc agc ccc gcc tca cag ctg gcc atc acc ttc      2112
Ser Ala Pro Arg Phe Ile Ser Pro Ala Ser Gln Leu Ala Ile Thr Phe
    690                 695                 700 agc ctc atc tcg ctg cag ctg ctg ggc atc tgt gtg tgg ttt gtg gtg      2160
Ser Leu Ile Ser Leu Gln Leu Leu Gly Ile Cys Val Trp Phe Val Val
705                 710                 715                 720 gac ccc tcc cac tcg gtg gtg gac ttc cag gac cag cgg aca ctc gac      2208
Asp Pro Ser His Ser Val Val Asp Phe Gln Asp Gln Arg Thr Leu Asp
                725                 730                 735 ccc cgc ttc gcc agg ggt gtg ctc aag tgt gac atc tcg gac ctg tcg      2256
Pro Arg Phe Ala Arg Gly Val Leu Lys Cys Asp Ile Ser Asp Leu Ser
            740                 745                 750 ctc atc tgc ctg ctg ggc tac agc atg ctg ctc atg gtc acg tgc acc      2304
Leu Ile Cys Leu Leu Gly Tyr Ser Met Leu Leu Met Val Thr Cys Thr
        755                 760                 765 gtg tat gcc atc aag aca cgc ggc gtg ccc gag acc ttc aat gag gcc      2352
Val Tyr Ala Ile Lys Thr Arg Gly Val Pro Glu Thr Phe Asn Glu Ala
    770                 775                 780
```

-continued

```
aag ccc att ggc ttc acc atg tac acc act tgc atc gtc tgg ctg gcc    2400
Lys Pro Ile Gly Phe Thr Met Tyr Thr Thr Cys Ile Val Trp Leu Ala
785             790                 795                 800 ttc atc ccc atc ttc ttt ggc acc tcg cag tcg gcc gac aag ctg tac    2448
Phe Ile Pro Ile Phe Phe Gly Thr Ser Gln Ser Ala Asp Lys Leu Tyr
                805                 810                 815 atc cag acg acg acg ctg acg gtc tcg gtg agt ctg agc gcc tcg gtg    2496
Ile Gln Thr Thr Thr Leu Thr Val Ser Val Ser Leu Ser Ala Ser Val
            820                 825                 830 tcc ctg gga atg ctc tac atg ccc aaa gtc tac atc atc ctc ttc cac    2544
Ser Leu Gly Met Leu Tyr Met Pro Lys Val Tyr Ile Ile Leu Phe His
        835                 840                 845 ccg gag cag aac gtg ccc aag cgc aag cgc agc ctc aaa gcc gtc gtt    2592
Pro Glu Gln Asn Val Pro Lys Arg Lys Arg Ser Leu Lys Ala Val Val
    850                 855                 860 acg gcg gcc acc atg tcc aac aag ttc acg cag aag ggc aac ttc cgg    2640
Thr Ala Ala Thr Met Ser Asn Lys Phe Thr Gln Lys Gly Asn Phe Arg
865                 870                 875                 880 ccc aac gga gag gcc aag tct gag ctc tgc gag aac ctt gag gcc cca    2688
Pro Asn Gly Glu Ala Lys Ser Glu Leu Cys Glu Asn Leu Glu Ala Pro
                885                 890                 895 gcg ctg gcc acc aaa cag act tac gtc act tac acc aac cat gca atc    2736
Ala Leu Ala Thr Lys Gln Thr Tyr Val Thr Tyr Thr Asn His Ala Ile
            900                 905                 910

<210> SEQ ID NO 2
<211> LENGTH: 912
<212> TYPE: PRT
<213> ORGANISM: Homo sapiens

<400> SEQUENCE: 2

Met Pro Gly Lys Arg Gly Leu Gly Trp Trp Ala Arg Leu Pro Leu
 1               5                  10                  15

Cys Leu Leu Leu Ser Leu Tyr Gly Pro Trp Met Pro Ser Ser Leu Gly
                20                  25                  30

Lys Pro Lys Gly His Pro His Met Asn Ser Ile Arg Ile Asp Gly Asp
            35                  40                  45

Ile Thr Leu Gly Gly Leu Phe Pro Val His Gly Arg Gly Ser Glu Gly
        50                  55                  60

Lys Pro Cys Gly Glu Leu Lys Lys Glu Lys Gly Ile His Arg Leu Glu
65                  70                  75                  80

Ala Met Leu Phe Ala Leu Asp Arg Ile Asn Asn Asp Pro Asp Leu Leu
                85                  90                  95

Pro Asn Ile Thr Leu Gly Ala Arg Ile Leu Asp Thr Cys Ser Arg Asp
            100                 105                 110

Thr His Ala Leu Glu Gln Ser Leu Thr Phe Val Gln Ala Leu Ile Glu
        115                 120                 125

Lys Asp Gly Thr Glu Val Arg Cys Gly Ser Gly Gly Pro Pro Ile Ile
    130                 135                 140

Thr Lys Pro Glu Arg Val Val Gly Val Ile Gly Ala Ser Gly Ser Ser
145                 150                 155                 160

Val Ser Ile Met Val Ala Asn Ile Leu Arg Leu Phe Lys Ile Pro Gln
                165                 170                 175

Ile Ser Tyr Ala Ser Thr Ala Pro Asp Leu Ser Asp Asn Ser Arg Tyr
            180                 185                 190

Asp Phe Phe Ser Arg Val Val Pro Ser Asp Thr Tyr Gln Ala Gln Ala
        195                 200                 205
```

```
Met Val Asp Ile Val Arg Ala Leu Lys Trp Asn Tyr Val Ser Thr Val
    210                 215                 220
Ala Ser Glu Gly Ser Tyr Gly Glu Ser Gly Val Glu Ala Phe Ile Gln
225                 230                 235                 240
Lys Ser Arg Glu Asp Gly Gly Val Cys Ile Ala Gln Ser Val Lys Ile
                245                 250                 255
Pro Arg Glu Pro Lys Ala Gly Glu Phe Asp Lys Ile Ile Arg Arg Leu
                260                 265                 270
Leu Glu Thr Ser Asn Ala Arg Ala Val Ile Ile Phe Ala Asn Glu Asp
            275                 280                 285
Asp Ile Arg Arg Val Leu Glu Ala Ala Arg Ala Asn Gln Thr Gly
290                 295                 300
His Phe Phe Trp Met Gly Ser Asp Ser Trp Gly Ser Lys Ile Ala Pro
305                 310                 315                 320
Val Leu His Leu Glu Glu Val Ala Glu Gly Ala Val Thr Ile Leu Pro
                325                 330                 335
Lys Arg Met Ser Val Arg Gly Phe Asp Arg Tyr Phe Ser Ser Arg Thr
                340                 345                 350
Leu Asp Asn Asn Arg Arg Asn Ile Trp Phe Ala Glu Phe Trp Glu Asp
            355                 360                 365
Asn Phe His Cys Lys Leu Ser Arg His Ala Leu Lys Lys Gly Ser His
370                 375                 380
Val Lys Lys Cys Thr Asn Arg Glu Arg Ile Gly Gln Asp Ser Ala Tyr
385                 390                 395                 400
Glu Gln Glu Gly Lys Val Gln Phe Val Ile Asp Ala Val Tyr Ala Met
                405                 410                 415
Gly His Ala Leu His Ala Met His Arg Asp Leu Cys Pro Gly Arg Val
                420                 425                 430
Gly Leu Cys Pro Arg Met Asp Pro Val Asp Gly Thr Gln Leu Leu Lys
            435                 440                 445
Tyr Ile Arg Asn Val Asn Phe Ser Gly Ile Ala Gly Asn Pro Val Thr
450                 455                 460
Phe Asn Glu Asn Gly Asp Ala Pro Gly Arg Tyr Asp Ile Tyr Gln Tyr
465                 470                 475                 480
Gln Leu Arg Asn Asp Ser Ala Glu Tyr Lys Val Ile Gly Ser Trp Thr
                485                 490                 495
Asp His Leu His Leu Arg Ile Glu Arg Met His Trp Pro Gly Ser Gly
            500                 505                 510
Gln Gln Leu Pro Arg Ser Ile Cys Ser Leu Pro Cys Gln Pro Gly Glu
            515                 520                 525
Arg Lys Lys Thr Val Lys Gly Met Pro Cys Cys Trp His Cys Glu Pro
530                 535                 540
Cys Thr Gly Tyr Gln Tyr Gln Val Asp Arg Tyr Thr Cys Lys Thr Cys
545                 550                 555                 560
Pro Tyr Asp Met Arg Pro Thr Glu Asn Arg Thr Gly Cys Arg Pro Ile
                565                 570                 575
Pro Ile Ile Lys Leu Glu Trp Gly Ser Pro Trp Ala Val Leu Pro Leu
            580                 585                 590
Phe Leu Ala Val Val Gly Ile Ala Ala Thr Leu Phe Val Val Ile Thr
            595                 600                 605
Phe Val Arg Tyr Asn Asp Thr Pro Ile Val Lys Ala Ser Gly Arg Glu
610                 615                 620
```

```
Leu Ser Tyr Val Leu Leu Ala Gly Ile Phe Leu Cys Tyr Ala Thr Thr
625                 630                 635                 640

Phe Leu Met Ile Ala Glu Pro Asp Leu Gly Thr Cys Ser Leu Arg Arg
            645                 650                 655

Ile Phe Leu Gly Leu Gly Met Ser Ile Ser Tyr Ala Ala Leu Leu Thr
                660                 665                 670

Lys Thr Asn Arg Ile Tyr Arg Ile Phe Glu Gln Gly Lys Arg Ser Val
            675                 680                 685

Ser Ala Pro Arg Phe Ile Ser Pro Ala Ser Gln Leu Ala Ile Thr Phe
690                 695                 700

Ser Leu Ile Ser Leu Gln Leu Leu Gly Ile Cys Val Trp Phe Val Val
705                 710                 715                 720

Asp Pro Ser His Ser Val Val Asp Phe Gln Asp Gln Arg Thr Leu Asp
                725                 730                 735

Pro Arg Phe Ala Arg Gly Val Leu Lys Cys Asp Ile Ser Asp Leu Ser
                740                 745                 750

Leu Ile Cys Leu Leu Gly Tyr Ser Met Leu Leu Met Val Thr Cys Thr
            755                 760                 765

Val Tyr Ala Ile Lys Thr Arg Gly Val Pro Glu Thr Phe Asn Glu Ala
770                 775                 780

Lys Pro Ile Gly Phe Thr Met Tyr Thr Thr Cys Ile Val Trp Leu Ala
785                 790                 795                 800

Phe Ile Pro Ile Phe Phe Gly Thr Ser Gln Ser Ala Asp Lys Leu Tyr
                805                 810                 815

Ile Gln Thr Thr Thr Leu Thr Val Ser Val Ser Leu Ser Ala Ser Val
            820                 825                 830

Ser Leu Gly Met Leu Tyr Met Pro Lys Val Tyr Ile Ile Leu Phe His
            835                 840                 845

Pro Glu Gln Asn Val Pro Lys Arg Lys Arg Ser Leu Lys Ala Val Val
850                 855                 860

Thr Ala Ala Thr Met Ser Asn Lys Phe Thr Gln Lys Gly Asn Phe Arg
865                 870                 875                 880

Pro Asn Gly Glu Ala Lys Ser Glu Leu Cys Glu Asn Leu Glu Ala Pro
                885                 890                 895

Ala Leu Ala Thr Lys Gln Thr Tyr Val Thr Tyr Thr Asn His Ala Ile
                900                 905                 910

<210> SEQ ID NO 3
<211> LENGTH: 3804
<212> TYPE: DNA
<213> ORGANISM: Homo sapiens
<220> FEATURE:
<221> NAME/KEY: CDS
<222> LOCATION: (1)..(2604)
<220> FEATURE:
<221> NAME/KEY: unsure
<222> LOCATION: (3325)..(3495)
<223> OTHER INFORMATION: nucleotides designated as n could be a or g or
      c or t/u

<400> SEQUENCE: 3 ccc gta cac gcc aag ggt ccc agc gga gtg ccc tgc ggc gac atc aag       48
Pro Val His Ala Lys Gly Pro Ser Gly Val Pro Cys Gly Asp Ile Lys
  1               5                  10                  15 agg gaa aac ggg atc cac agg ctg gaa gcg atg ctc tac gcc ctg gac       96
Arg Glu Asn Gly Ile His Arg Leu Glu Ala Met Leu Tyr Ala Leu Asp
             20                  25                  30 cag atc aac agt gat ccc aac cta ctg ccc aac gtg acg ctg ggc gcg      144
```

-continued

| | |
|---|---|
| Gln Ile Asn Ser Asp Pro Asn Leu Leu Pro Asn Val Thr Leu Gly Ala<br>           35                   40                   45 | |
| cgg atc ctg gac act tgt tcc agg gac act tac gcg ctc gaa cag tcg<br>Arg Ile Leu Asp Thr Cys Ser Arg Asp Thr Tyr Ala Leu Glu Gln Ser<br> 50                    55                 60 | 192 |
| ctt act ttc gtc cag gcg ctc atc cag aag gac acc tcc gac gtg cgc<br>Leu Thr Phe Val Gln Ala Leu Ile Gln Lys Asp Thr Ser Asp Val Arg<br> 65                    70                75                80 | 240 |
| tgc acc aac ggc gaa ccg ccg gtt ttc gtc aag ccg gag aaa gta gtt<br>Cys Thr Asn Gly Glu Pro Pro Val Phe Val Lys Pro Glu Lys Val Val<br>                 85                 90                95 | 288 |
| gga gtg att ggg gct tcg ggg agt tcg gtc tcc atc atg gta gcc aac<br>Gly Val Ile Gly Ala Ser Gly Ser Ser Val Ser Ile Met Val Ala Asn<br>                100               105            110 | 336 |
| atc ctg agg ctc ttc cag atc ccc cag att agt tat gca tca acg gca<br>Ile Leu Arg Leu Phe Gln Ile Pro Gln Ile Ser Tyr Ala Ser Thr Ala<br>                115               120            125 | 384 |
| ccc gag cta agt gat gac cgg cgc tat gac ttc ttc tct cgc gtg gtg<br>Pro Glu Leu Ser Asp Asp Arg Arg Tyr Asp Phe Phe Ser Arg Val Val<br>       130                 135               140 | 432 |
| cca ccc gat tcc ttc caa gcc cag gcc atg gta gac att gta aag gcc<br>Pro Pro Asp Ser Phe Gln Ala Gln Ala Met Val Asp Ile Val Lys Ala<br>145                   150               155            160 | 480 |
| cta ggc tgg aat tat gtg tct acc ctc gca tcg gaa gga agt tat gga<br>Leu Gly Trp Asn Tyr Val Ser Thr Leu Ala Ser Glu Gly Ser Tyr Gly<br>                165               170            175 | 528 |
| gag aaa ggt gtg gag tcc ttc acg cag att tcc aaa gag gca ggt gga<br>Glu Lys Gly Val Glu Ser Phe Thr Gln Ile Ser Lys Glu Ala Gly Gly<br>       180                 185               190 | 576 |
| ctc tgc att gcc cag tcc gtg aga atc ccc cag gaa cgc aaa gac agg<br>Leu Cys Ile Ala Gln Ser Val Arg Ile Pro Gln Glu Arg Lys Asp Arg<br>                195               200            205 | 624 |
| acc att gac ttt gat aga att atc aaa cag ctc ctg gac acc ccc aac<br>Thr Ile Asp Phe Asp Arg Ile Ile Lys Gln Leu Leu Asp Thr Pro Asn<br>       210                 215               220 | 672 |
| tcc agg gcc gtc gtg att ttt gcc aac gat gag gat ata aag cag atc<br>Ser Arg Ala Val Val Ile Phe Ala Asn Asp Glu Asp Ile Lys Gln Ile<br>225                   230               235            240 | 720 |
| ctt gca gca gcc aaa aga gct gac caa gtt ggc cat ttt ctt tgg gtg<br>Leu Ala Ala Ala Lys Arg Ala Asp Gln Val Gly His Phe Leu Trp Val<br>                245               250            255 | 768 |
| gga tca gac agc tgg gga tcc aaa ata aac cca ctg cac cag cat gaa<br>Gly Ser Asp Ser Trp Gly Ser Lys Ile Asn Pro Leu His Gln His Glu<br>       260                 265               270 | 816 |
| gat atc gca gaa ggg gcc atc acc att cag ccc aag cga gcc acg gtg<br>Asp Ile Ala Glu Gly Ala Ile Thr Ile Gln Pro Lys Arg Ala Thr Val<br>                275               280            285 | 864 |
| gaa ggg ttt gat gcc tac ttt acg tcc cgt aca ctt gaa aac aac aga<br>Glu Gly Phe Asp Ala Tyr Phe Thr Ser Arg Thr Leu Glu Asn Asn Arg<br>       290                 295               300 | 912 |
| aga aat gta tgg ttt gcc gaa tac tgg gag gaa aac ttc aac tgc aag<br>Arg Asn Val Trp Phe Ala Glu Tyr Trp Glu Glu Asn Phe Asn Cys Lys<br>305                   310               315            320 | 960 |
| ttg acg att agt ggg tca aaa aaa gaa gac aca gat cgc aaa tgc aca<br>Leu Thr Ile Ser Gly Ser Lys Lys Glu Asp Thr Asp Arg Lys Cys Thr<br>                325               330            335 | 1008 |
| gga cag gag aga att gga aaa gat tcc aac tat gag cag gag ggt aaa<br>Gly Gln Glu Arg Ile Gly Lys Asp Ser Asn Tyr Glu Gln Glu Gly Lys<br>       340                 345               350 | 1056 |

-continued

| | |
|---|---|
| gtc cag ttc gtg att gac gca gtc tat gct atg gct cac gcc ctt cac<br>Val Gln Phe Val Ile Asp Ala Val Tyr Ala Met Ala His Ala Leu His<br>      355                        360                  365 | 1104 |
| cac atg aac aag gat ctc tgt gct gac tac cgg ggt gtc tgc cca gag<br>His Met Asn Lys Asp Leu Cys Ala Asp Tyr Arg Gly Val Cys Pro Glu<br>370                        375                      380 | 1152 |
| atg gag caa gct gga ggc aag aag ttg ctg aag tat ata cgc aat gtt<br>Met Glu Gln Ala Gly Gly Lys Lys Leu Leu Lys Tyr Ile Arg Asn Val<br>385                        390                      395                  400 | 1200 |
| aat ttc aat ggt agt gct ggc act cca gtg atg ttt aac aag aac ggg<br>Asn Phe Asn Gly Ser Ala Gly Thr Pro Val Met Phe Asn Lys Asn Gly<br>                        405                      410                      415 | 1248 |
| gat gca cct ggg cgt tat gac atc ttt cag tac cag acc aca aac acc<br>Asp Ala Pro Gly Arg Tyr Asp Ile Phe Gln Tyr Gln Thr Thr Asn Thr<br>                  420                      425                      430 | 1296 |
| agc aac ccg ggt tac cgt ctg atc ggg cag tgg aca gac gaa ctt cag<br>Ser Asn Pro Gly Tyr Arg Leu Ile Gly Gln Trp Thr Asp Glu Leu Gln<br>              435                      440                      445 | 1344 |
| ctc aat ata gaa gac atg cag tgg ggt aaa gga gtc cga gag ata ccc<br>Leu Asn Ile Glu Asp Met Gln Trp Gly Lys Gly Val Arg Glu Ile Pro<br>450                        455                      460 | 1392 |
| gcc tca gtg tgc aca cta cca tgt aag cca gga cag aga aag aag aca<br>Ala Ser Val Cys Thr Leu Pro Cys Lys Pro Gly Gln Arg Lys Lys Thr<br>465                        470                      475                  480 | 1440 |
| cag aaa gga act cct tgc tgt tgg acc tgt gag cct tgc gat ggt tac<br>Gln Lys Gly Thr Pro Cys Cys Trp Thr Cys Glu Pro Cys Asp Gly Tyr<br>                        485                      490                      495 | 1488 |
| cag tac cag ttt gat gag atg aca tgc cag cat tgc ccc tat gac cag<br>Gln Tyr Gln Phe Asp Glu Met Thr Cys Gln His Cys Pro Tyr Asp Gln<br>                  500                      505                      510 | 1536 |
| agg ccc aat gaa aat cga acc gga tgc cag gat att ccc atc atc aaa<br>Arg Pro Asn Glu Asn Arg Thr Gly Cys Gln Asp Ile Pro Ile Ile Lys<br>              515                      520                      525 | 1584 |
| ctg gag tgg cac tcc ccc tgg gct gtg att cct gtc ttc ctg gca atg<br>Leu Glu Trp His Ser Pro Trp Ala Val Ile Pro Val Phe Leu Ala Met<br>530                        535                      540 | 1632 |
| ttg ggg atc att gcc acc atc ttt gtc atg gcc act ttc atc cgc tac<br>Leu Gly Ile Ile Ala Thr Ile Phe Val Met Ala Thr Phe Ile Arg Tyr<br>545                        550                      555                  560 | 1680 |
| aat gac acg ccc att gtc cgg gca tct ggg cgg gaa ctc agc tat gtt<br>Asn Asp Thr Pro Ile Val Arg Ala Ser Gly Arg Glu Leu Ser Tyr Val<br>                        565                      570                      575 | 1728 |
| ctt ttg acg ggc atc ttt ctt tgc tac atc atc act ttc ctg atg att<br>Leu Leu Thr Gly Ile Phe Leu Cys Tyr Ile Ile Thr Phe Leu Met Ile<br>                  580                      585                      590 | 1776 |
| gcc aaa cca gat gtg gca gtg tgt tct ttc cgg cga gtt ttc ttg ggc<br>Ala Lys Pro Asp Val Ala Val Cys Ser Phe Arg Arg Val Phe Leu Gly<br>              595                      600                      605 | 1824 |
| ttg ggt atg tgc atc agt tat gca gcc ctc ttg acg aaa aca aat cgg<br>Leu Gly Met Cys Ile Ser Tyr Ala Ala Leu Leu Thr Lys Thr Asn Arg<br>610                        615                      620 | 1872 |
| att tat cgc ata ttt gag cag ggc aag aaa tca gta aca gct ccc aga<br>Ile Tyr Arg Ile Phe Glu Gln Gly Lys Lys Ser Val Thr Ala Pro Arg<br>625                        630                      635                  640 | 1920 |
| ctc ata agc cca aca tca caa ctg gca atc act tcc agt tta ata tca<br>Leu Ile Ser Pro Thr Ser Gln Leu Ala Ile Thr Ser Ser Leu Ile Ser<br>                  645                      650                      655 | 1968 |
| gtt cag ctt cta ggg gtg ttc att tgg ttt ggt gtt gat cca ccc aac<br>Val Gln Leu Leu Gly Val Phe Ile Trp Phe Gly Val Asp Pro Pro Asn<br>              660                      665                      670 | 2016 |

```
atc atc ata gac tac gat gaa cac aag aca atg aac cct gag caa gcc   2064
Ile Ile Ile Asp Tyr Asp Glu His Lys Thr Met Asn Pro Glu Gln Ala
            675                 680                 685 aga ggg gtt ctc aag tgt gac att aca gat ctc caa atc att tgc tcc   2112
Arg Gly Val Leu Lys Cys Asp Ile Thr Asp Leu Gln Ile Ile Cys Ser
690                 695                 700 ttg gga tat agc att ctt ctc atg gtc aca tgt act gtg tat gcc atc   2160
Leu Gly Tyr Ser Ile Leu Leu Met Val Thr Cys Thr Val Tyr Ala Ile
705                 710                 715                 720 aag act cgg ggt gta ccc gag aat ttt aac gaa gcc aag ccc att gga   2208
Lys Thr Arg Gly Val Pro Glu Asn Phe Asn Glu Ala Lys Pro Ile Gly
                725                 730                 735 ttc act atg tac acg aca tgt ata gta tgg ctt gcc ttc att cca att   2256
Phe Thr Met Tyr Thr Thr Cys Ile Val Trp Leu Ala Phe Ile Pro Ile
            740                 745                 750 ttt ttt ggc acc gct caa tca gcg gaa aag ctc tac ata caa act acc   2304
Phe Phe Gly Thr Ala Gln Ser Ala Glu Lys Leu Tyr Ile Gln Thr Thr
        755                 760                 765 acg ctt aca atc tcc atg aac cta agt gca tca gtg gcg ctg ggg atg   2352
Thr Leu Thr Ile Ser Met Asn Leu Ser Ala Ser Val Ala Leu Gly Met
770                 775                 780 cta tac atg ccg aaa gtg tac atc atc att ttc cac cct gaa ctc aat   2400
Leu Tyr Met Pro Lys Val Tyr Ile Ile Ile Phe His Pro Glu Leu Asn
785                 790                 795                 800 gtc cag aaa cgg aag cga agc ttc aag gcg gta gtc aca gca gcc acc   2448
Val Gln Lys Arg Lys Arg Ser Phe Lys Ala Val Val Thr Ala Ala Thr
                805                 810                 815 atg tca tcg agg ctg tca cac aaa ccc agt gac aga ccc aac ggt gag   2496
Met Ser Ser Arg Leu Ser His Lys Pro Ser Asp Arg Pro Asn Gly Glu
            820                 825                 830 gca aag acc gag ctc tgt gaa aac gta gac cca aac aac tgt ata cca   2544
Ala Lys Thr Glu Leu Cys Glu Asn Val Asp Pro Asn Asn Cys Ile Pro
        835                 840                 845 cca gta aga aag agt gta caa aag tct gtt act tgg tac act atc cca   2592
Pro Val Arg Lys Ser Val Gln Lys Ser Val Thr Trp Tyr Thr Ile Pro
850                 855                 860 cca aca gta tag cttttgactg ctttcccaaa ggccctgctg caaaaaagaa        2644
Pro Thr Val
865 gtatgtcagt tataataacc tggttatcta acctgttcca ttccatggaa ccatggagga   2704 ggaagaccct cagttatttt gtcacccaac ctggcatagg actctttggt cctacccgct   2764 tcccatcacc ggaggagctt ccccggccgg gagaccagtg ttagaggatc caagcgacct   2824 aaacagctgc tttatgaaat atccttactt tatctgggct taataagtca ctgacatcag   2884 cactgccaac ttggctgcaa ttgtggacct tccctaccaa agggagtgtt gaaactcaag   2944 tcccgccccg gctctttaga atggaccact gagagccaca ggaccgtttt ggggctgacc   3004 tgtcttatta cgtatgtact tctaggttgc aaggttttga aattttctgt acagtttgtg   3064 aggacctttg cactttgcca tctgatgtcg tacctcggtt cactgtttgt tttcgaatgc   3124 cttgttttca tagagcccta ttctctcaga cggtggaata tttggaaaaa ttttaaaaca   3184 attaaaattt taaagcaatc ttggcagact aaaacaagta catctgtaca tgactgtata   3244 attacgttat agtaccactg cacatcatgt ttttttttt aagacaaaaa agatgtttaa   3304 agaccaaaaa ctgtgctgag naagtatgcc ccacctatct ttngnatatg ataggttaca   3364 taaaaggaag gtattggctg aactgnatag aggtcttgat ctttggaatg catgccagta   3424
```

-continued

```
atgtatttac agtacatgtt tattatgttc aatatttgta tttgtgttct cttttgttat    3484
ttttaattag ngtatatgaa tattttgcaa taattttaat aattattaag ctgtttgaag    3544
gaaagaatat ggattttca tgtcttgagg ttttgttcat gccccctttg actgatcagt    3604
gtgataagga ctttaggaaa aaaagcatgt atgtttttta ctgtttgtaa taagtacttt    3664
cgttaatctt gctgcttatg tgccaattta gtggaaaaga acaacccttg ctgaaaaatt    3724
ccctctttcc attctctttc aattctgtga tattgtccaa gaatgtatca ataaaatact    3784
ttggttaact ttaaaaaaaa                                                3804
```

<210> SEQ ID NO 4
<211> LENGTH: 867
<212> TYPE: PRT
<213> ORGANISM: Homo sapiens

<400> SEQUENCE: 4

```
Pro Val His Ala Lys Gly Pro Ser Gly Val Pro Cys Gly Asp Ile Lys
 1               5                  10                  15

Arg Glu Asn Gly Ile His Arg Leu Glu Ala Met Leu Tyr Ala Leu Asp
            20                  25                  30

Gln Ile Asn Ser Asp Pro Asn Leu Leu Pro Asn Val Thr Leu Gly Ala
        35                  40                  45

Arg Ile Leu Asp Thr Cys Ser Arg Asp Thr Tyr Ala Leu Glu Gln Ser
    50                  55                  60

Leu Thr Phe Val Gln Ala Leu Ile Gln Lys Asp Thr Ser Asp Val Arg
65                  70                  75                  80

Cys Thr Asn Gly Glu Pro Pro Val Phe Val Lys Pro Glu Lys Val Val
                85                  90                  95

Gly Val Ile Gly Ala Ser Gly Ser Val Ser Ile Met Val Ala Asn
            100                 105                 110

Ile Leu Arg Leu Phe Gln Ile Pro Gln Ile Ser Tyr Ala Ser Thr Ala
        115                 120                 125

Pro Glu Leu Ser Asp Asp Arg Arg Tyr Asp Phe Phe Ser Arg Val Val
    130                 135                 140

Pro Pro Asp Ser Phe Gln Ala Gln Ala Met Val Asp Ile Val Lys Ala
145                 150                 155                 160

Leu Gly Trp Asn Tyr Val Ser Thr Leu Ala Ser Glu Gly Ser Tyr Gly
                165                 170                 175

Glu Lys Gly Val Glu Ser Phe Thr Gln Ile Ser Lys Glu Ala Gly Gly
            180                 185                 190

Leu Cys Ile Ala Gln Ser Val Arg Ile Pro Gln Glu Arg Lys Asp Arg
        195                 200                 205

Thr Ile Asp Phe Asp Arg Ile Ile Lys Gln Leu Leu Asp Thr Pro Asn
    210                 215                 220

Ser Arg Ala Val Val Ile Phe Ala Asn Asp Glu Asp Ile Lys Gln Ile
225                 230                 235                 240

Leu Ala Ala Ala Lys Arg Ala Asp Gln Val Gly His Phe Leu Trp Val
                245                 250                 255

Gly Ser Asp Ser Trp Gly Ser Lys Ile Asn Pro Leu His Gln His Glu
            260                 265                 270

Asp Ile Ala Glu Gly Ala Ile Thr Ile Gln Pro Lys Arg Ala Thr Val
        275                 280                 285

Glu Gly Phe Asp Ala Tyr Phe Thr Ser Arg Thr Leu Glu Asn Asn Arg
    290                 295                 300
```

-continued

```
Arg Asn Val Trp Phe Ala Glu Tyr Trp Glu Asn Phe Asn Cys Lys
305                 310                 315                 320

Leu Thr Ile Ser Gly Ser Lys Lys Glu Asp Thr Asp Arg Lys Cys Thr
                325                 330                 335

Gly Gln Glu Arg Ile Gly Lys Asp Ser Asn Tyr Glu Gln Glu Gly Lys
            340                 345                 350

Val Gln Phe Val Ile Asp Ala Val Tyr Ala Met Ala His Ala Leu His
        355                 360                 365

His Met Asn Lys Asp Leu Cys Ala Asp Tyr Arg Gly Val Cys Pro Glu
    370                 375                 380

Met Glu Gln Ala Gly Gly Lys Lys Leu Leu Lys Tyr Ile Arg Asn Val
385                 390                 395                 400

Asn Phe Asn Gly Ser Ala Gly Thr Pro Val Met Phe Asn Lys Asn Gly
                405                 410                 415

Asp Ala Pro Gly Arg Tyr Asp Ile Phe Gln Tyr Gln Thr Thr Asn Thr
            420                 425                 430

Ser Asn Pro Gly Tyr Arg Leu Ile Gly Gln Trp Thr Asp Glu Leu Gln
        435                 440                 445

Leu Asn Ile Glu Asp Met Gln Trp Gly Lys Gly Val Arg Glu Ile Pro
    450                 455                 460

Ala Ser Val Cys Thr Leu Pro Cys Lys Pro Gly Gln Arg Lys Lys Thr
465                 470                 475                 480

Gln Lys Gly Thr Pro Cys Cys Trp Thr Cys Glu Pro Cys Asp Gly Tyr
                485                 490                 495

Gln Tyr Gln Phe Asp Glu Met Thr Cys Gln His Cys Pro Tyr Asp Gln
            500                 505                 510

Arg Pro Asn Glu Asn Arg Thr Gly Cys Gln Asp Ile Pro Ile Ile Lys
        515                 520                 525

Leu Glu Trp His Ser Pro Trp Ala Val Ile Pro Val Phe Leu Ala Met
    530                 535                 540

Leu Gly Ile Ile Ala Thr Ile Phe Val Met Ala Thr Phe Ile Arg Tyr
545                 550                 555                 560

Asn Asp Thr Pro Ile Val Arg Ala Ser Gly Arg Glu Leu Ser Tyr Val
                565                 570                 575

Leu Leu Thr Gly Ile Phe Leu Cys Tyr Ile Ile Thr Phe Leu Met Ile
            580                 585                 590

Ala Lys Pro Asp Val Ala Val Cys Ser Phe Arg Arg Val Phe Leu Gly
        595                 600                 605

Leu Gly Met Cys Ile Ser Tyr Ala Ala Leu Leu Thr Lys Thr Asn Arg
    610                 615                 620

Ile Tyr Arg Ile Phe Glu Gln Gly Lys Lys Ser Val Thr Ala Pro Arg
625                 630                 635                 640

Leu Ile Ser Pro Thr Ser Gln Leu Ala Ile Thr Ser Ser Leu Ile Ser
                645                 650                 655

Val Gln Leu Leu Gly Val Phe Ile Trp Phe Gly Val Asp Pro Pro Asn
            660                 665                 670

Ile Ile Ile Asp Tyr Asp Glu His Lys Thr Met Asn Pro Glu Gln Ala
        675                 680                 685

Arg Gly Val Leu Lys Cys Asp Ile Thr Asp Leu Gln Ile Ile Cys Ser
    690                 695                 700

Leu Gly Tyr Ser Ile Leu Leu Met Val Thr Cys Thr Val Tyr Ala Ile
705                 710                 715                 720

Lys Thr Arg Gly Val Pro Glu Asn Phe Asn Glu Ala Lys Pro Ile Gly
```

```
                      725                 730                 735
Phe Thr Met Tyr Thr Thr Cys Ile Val Trp Leu Ala Phe Ile Pro Ile
                740                 745                 750

Phe Phe Gly Thr Ala Gln Ser Ala Glu Lys Leu Tyr Ile Gln Thr Thr
            755                 760                 765

Thr Leu Thr Ile Ser Met Asn Leu Ser Ala Ser Val Ala Leu Gly Met
        770                 775                 780

Leu Tyr Met Pro Lys Val Tyr Ile Ile Phe His Pro Glu Leu Asn
785                 790                 795                 800

Val Gln Lys Arg Lys Arg Ser Phe Lys Ala Val Val Thr Ala Ala Thr
                805                 810                 815

Met Ser Ser Arg Leu Ser His Lys Pro Ser Asp Arg Pro Asn Gly Glu
                820                 825                 830

Ala Lys Thr Glu Leu Cys Glu Asn Val Asp Pro Asn Asn Cys Ile Pro
            835                 840                 845

Pro Val Arg Lys Ser Val Gln Lys Ser Val Thr Trp Tyr Thr Ile Pro
        850                 855                 860

Pro Thr Val
865

<210> SEQ ID NO 5
<211> LENGTH: 1399
<212> TYPE: DNA
<213> ORGANISM: Homo sapiens
<220> FEATURE:
<221> NAME/KEY: CDS
<222> LOCATION: (1)..(270)
<220> FEATURE:
<221> NAME/KEY: unsure
<222> LOCATION: (920)..(1090)
<223> OTHER INFORMATION: Nucleotides designated as n could be a or g or
      c or t/u

<400> SEQUENCE: 5 atc tcc atg aac cta agt gca tca gtg gcg ctg ggg atg cta tac atg      48
Ile Ser Met Asn Leu Ser Ala Ser Val Ala Leu Gly Met Leu Tyr Met
  1               5                  10                  15 ccg aaa gtg tac atc atc att ttc cac cct gaa ctc aat gtc cag aaa      96
Pro Lys Val Tyr Ile Ile Ile Phe His Pro Glu Leu Asn Val Gln Lys
             20                  25                  30 cgg aag cga agc ttc aag gcg gta gtc aca gca gcc acc atg tca tcg     144
Arg Lys Arg Ser Phe Lys Ala Val Val Thr Ala Ala Thr Met Ser Ser
         35                  40                  45 agg ctg tca cac aaa ccc agt gac aga ccc aac ggt gag gca aag acc     192
Arg Leu Ser His Lys Pro Ser Asp Arg Pro Asn Gly Glu Ala Lys Thr
     50                  55                  60 gag ctc tgt gaa aac gta gac cca aac agc cct gct gca aaa aag aag     240
Glu Leu Cys Glu Asn Val Asp Pro Asn Ser Pro Ala Ala Lys Lys Lys
 65                  70                  75                  80 tat gtc agt tat aat aac ctg gtt atc taa cctgttccat tccatggaac       290
Tyr Val Ser Tyr Asn Asn Leu Val Ile
                 85 catggaggag gaagaccctc agttattttg tcacccaacc tggcatagga ctctttggtc   350 ctacccgctt cccatcaccg gaggagcttc cccggccggg agaccagtgt tagaggatcc   410 aagcgaccta acagctgct ttatgaaata tccttacttt atctgggctt aataagtcac    470 tgacatcagc actgccaact ggctgcaat tgtggacctt ccctaccaaa gggagtgttg    530 aaactcaagt cccgccccgg ctctttagaa tggaccactg agagccacag gaccgttttg   590
```

-continued

```
gggctgacct gtcttattac gtatgtactt ctaggttgca aggttttgaa attttctgta    650
cagtttgtga ggacctttgc actttgccat ctgatgtcgt acctcggttc actgtttgtt    710
ttcgaatgcc ttgttttcat agagccctat tctctcagac ggtggaatat ttggaaaaat    770
tttaaaacaa ttaaaatttt aaagcaatct tggcagacta aaacaagtac atctgtacat    830
gactgtataa ttacgttata gtaccactgc acatcatgtt tttttttta agacaaaaaa    890 gatgtttaaa gaccaaaaac tgtgctgagn aagtatgccc cacctatctt tngnatatga    950
taggttacat aaaaggaagg tattggctga actgnataga ggtcttgatc tttggaatgc   1010
atgccagtaa tgtatttaca gtacatgttt attatgttca atatttgtat ttgtgttctc   1070
ttttgttatt tttaattagn gtatatgaat attttgcaat aattttaata attattaagc   1130
tgtttgaagg aaagaatatg gattttcat gtcttgaggt tttgttcatg cccctttga   1190 ctgatcagtg tgataaggac tttaggaaaa aaagcatgta tgttttttac tgtttgtaat   1250
aagtactttc gttaatcttg ctgcttatgt gccaatttag tggaaaagaa caacccttgc   1310
tgaaaaattc cctctttcca ttctctttca attctgtgat attgtccaag aatgtatcaa   1370
taaaatactt tggttaactt taaaaaaaa                                     1399
```

<210> SEQ ID NO 6
<211> LENGTH: 89
<212> TYPE: PRT
<213> ORGANISM: Homo sapiens

<400> SEQUENCE: 6

```
Ile Ser Met Asn Leu Ser Ala Ser Val Ala Leu Gly Met Leu Tyr Met
  1               5                  10                  15
Pro Lys Val Tyr Ile Ile Phe His Pro Glu Leu Asn Val Gln Lys
             20                  25                  30
Arg Lys Arg Ser Phe Lys Ala Val Val Thr Ala Ala Thr Met Ser Ser
         35                  40                  45
Arg Leu Ser His Lys Pro Ser Asp Arg Pro Asn Gly Glu Ala Lys Thr
     50                  55                  60
Glu Leu Cys Glu Asn Val Asp Pro Asn Ser Pro Ala Ala Lys Lys Lys
 65                  70                  75                  80
Tyr Val Ser Tyr Asn Asn Leu Val Ile
                 85
```

<210> SEQ ID NO 7
<211> LENGTH: 1588
<212> TYPE: DNA
<213> ORGANISM: Homo sapiens
<220> FEATURE:
<221> NAME/KEY: CDS
<222> LOCATION: (2)..(1447)

<400> SEQUENCE: 7

```
g aac aag gat ctc tgt gct gac tac cgg ggt gtc tgc cca gag atg gag     49
  Asn Lys Asp Leu Cys Ala Asp Tyr Arg Gly Val Cys Pro Glu Met Glu
  1               5                  10                  15 caa gct gga ggc aag aag ttg ctg aag tat ata cgc aat gtt aat ttc      97
Gln Ala Gly Gly Lys Lys Leu Leu Lys Tyr Ile Arg Asn Val Asn Phe
             20                  25                  30 aat ggt agt gct ggc act cca gtg atg ttt aac aag aac ggg gat gca     145
Asn Gly Ser Ala Gly Thr Pro Val Met Phe Asn Lys Asn Gly Asp Ala
         35                  40                  45 cct ggg cgt tat gac atc ttt cag tac cag acc aca aac acc agc aac     193
Pro Gly Arg Tyr Asp Ile Phe Gln Tyr Gln Thr Thr Asn Thr Ser Asn
```

```
          50                    55                    60
ccg ggt tac cgt ctg atc ggg cag tgg aca gac gaa ctt cag ctc aat    241
Pro Gly Tyr Arg Leu Ile Gly Gln Trp Thr Asp Glu Leu Gln Leu Asn
 65                  70                  75                  80 ata gaa gac atg cag tgg ggt aaa gga gtc cga gag ata ccc gcc tca    289
Ile Glu Asp Met Gln Trp Gly Lys Gly Val Arg Glu Ile Pro Ala Ser
                 85                  90                  95 gtg tgc aca cta cca tgt aag cca gga cag aga aag aag aca cag aaa    337
Val Cys Thr Leu Pro Cys Lys Pro Gly Gln Arg Lys Lys Thr Gln Lys
            100                 105                 110 gga act cct tgc tgt tgg acc tgt gag cct tgc gat ggt tac cag tac    385
Gly Thr Pro Cys Cys Trp Thr Cys Glu Pro Cys Asp Gly Tyr Gln Tyr
        115                 120                 125 cag ttt gat gag atg aca tgc cag cat tgc ccc tat gac cag agg ccc    433
Gln Phe Asp Glu Met Thr Cys Gln His Cys Pro Tyr Asp Gln Arg Pro
    130                 135                 140 aat gaa aat cga acc gga tgc cag gat att ccc atc atc aaa ctg gag    481
Asn Glu Asn Arg Thr Gly Cys Gln Asp Ile Pro Ile Ile Lys Leu Glu
145                 150                 155                 160 tgg cac tcc ccc tgg gct gtg att cct gtc ttc ctg gca atg ttg ggg    529
Trp His Ser Pro Trp Ala Val Ile Pro Val Phe Leu Ala Met Leu Gly
                165                 170                 175 atc att gcc acc atc ttt gtc atg gcc act ttc atc cgc tac aat gac    577
Ile Ile Ala Thr Ile Phe Val Met Ala Thr Phe Ile Arg Tyr Asn Asp
            180                 185                 190 acg ccc att gtc cgg gca tct ggg cgg gaa ctc agc tat gtt ctt ttg    625
Thr Pro Ile Val Arg Ala Ser Gly Arg Glu Leu Ser Tyr Val Leu Leu
        195                 200                 205 acg ggc atc ttt ctt tgc tac atc atc act ttc ctg atg att gcc aaa    673
Thr Gly Ile Phe Leu Cys Tyr Ile Ile Thr Phe Leu Met Ile Ala Lys
    210                 215                 220 cca gat gtg gca gtg tgt tct ttc cgg cga gtt ttc ttg ggc ttg ggt    721
Pro Asp Val Ala Val Cys Ser Phe Arg Arg Val Phe Leu Gly Leu Gly
225                 230                 235                 240 atg tgc atc agt tat gca gcc ctc ttg acg aaa aca aat cgg att tat    769
Met Cys Ile Ser Tyr Ala Ala Leu Leu Thr Lys Thr Asn Arg Ile Tyr
                245                 250                 255 cgc ata ttt gag cag ggc aag aaa tca gta aca gct ccc aga ctc ata    817
Arg Ile Phe Glu Gln Gly Lys Lys Ser Val Thr Ala Pro Arg Leu Ile
            260                 265                 270 agc cca aca tca caa ctg gca atc act tcc agt tta ata tca gtt cag    865
Ser Pro Thr Ser Gln Leu Ala Ile Thr Ser Ser Leu Ile Ser Val Gln
        275                 280                 285 ctt cta ggg gtg ttc att tgg ttt ggt gtt gat cca ccc aac atc atc    913
Leu Leu Gly Val Phe Ile Trp Phe Gly Val Asp Pro Pro Asn Ile Ile
    290                 295                 300 ata gac tac gat gaa cac aag aca atg aac cct gag caa gcc aga ggg    961
Ile Asp Tyr Asp Glu His Lys Thr Met Asn Pro Glu Gln Ala Arg Gly
305                 310                 315                 320 gtt ctc aag tgt gac att aca gat ctc caa atc att tgc tcc ttg gga   1009
Val Leu Lys Cys Asp Ile Thr Asp Leu Gln Ile Ile Cys Ser Leu Gly
                325                 330                 335 tat agc att ctt ctc atg gtc aca tgt act gtg tat gcc atc aag act   1057
Tyr Ser Ile Leu Leu Met Val Thr Cys Thr Val Tyr Ala Ile Lys Thr
            340                 345                 350 cgg ggt gta ccc gag aat ttt aac gaa gcc aag ccc att gga ttc act   1105
Arg Gly Val Pro Glu Asn Phe Asn Glu Ala Lys Pro Ile Gly Phe Thr
        355                 360                 365 atg tac acg aca tgt ata gta tgg ctt gcc ttc att cca att ttt ttt   1153
```

```
Met Tyr Thr Thr Cys Ile Val Trp Leu Ala Phe Ile Pro Ile Phe Phe
        370                 375                 380 ggc acc gct caa tca gcg gaa aag ctc tac ata caa act acc acg ctt    1201
Gly Thr Ala Gln Ser Ala Glu Lys Leu Tyr Ile Gln Thr Thr Thr Leu
385                 390                 395                 400 aca atc tcc atg aac cta agt gca tca gtg gcg ctg ggg atg cta tac    1249
Thr Ile Ser Met Asn Leu Ser Ala Ser Val Ala Leu Gly Met Leu Tyr
                405                 410                 415 atg ccg aaa gtg tac atc atc att ttc cac cct gaa ctc aat gtc cag    1297
Met Pro Lys Val Tyr Ile Ile Ile Phe His Pro Glu Leu Asn Val Gln
            420                 425                 430 aaa cgg aag cga agc ttc aag gcg gta gtc aca gca gcc acc atg tca    1345
Lys Arg Lys Arg Ser Phe Lys Ala Val Val Thr Ala Ala Thr Met Ser
        435                 440                 445 tcg agg ctg tca cac aaa ccc agt gac aga ccc aac ggt gag gca aag    1393
Ser Arg Leu Ser His Lys Pro Ser Asp Arg Pro Asn Gly Glu Ala Lys
450                 455                 460 acc gag ctc tgt gaa aac gta gac cca aac agt gag aag tgc aac tgc    1441
Thr Glu Leu Cys Glu Asn Val Asp Pro Asn Ser Glu Lys Cys Asn Cys
465                 470                 475                 480 tac tga ccatctgcac tggcatctag tcaagcgatt gtctgaggaa aggatttttgg    1497
Tyr agattcccat ctgatattct tctatttggt ctcttgtacc cattgtcatc ctgtaccaca   1557
cataataaag tttaagaatg tcaagcaaaa g                                  1588

<210> SEQ ID NO 8
<211> LENGTH: 481
<212> TYPE: PRT
<213> ORGANISM: Homo sapiens

<400> SEQUENCE: 8

Asn Lys Asp Leu Cys Ala Asp Tyr Arg Gly Val Cys Pro Glu Met Glu
  1               5                  10                  15

Gln Ala Gly Gly Lys Lys Leu Leu Lys Tyr Ile Arg Asn Val Asn Phe
             20                  25                  30

Asn Gly Ser Ala Gly Thr Pro Val Met Phe Asn Lys Asn Gly Asp Ala
         35                  40                  45

Pro Gly Arg Tyr Asp Ile Phe Gln Tyr Gln Thr Thr Asn Thr Ser Asn
     50                  55                  60

Pro Gly Tyr Arg Leu Ile Gly Gln Trp Thr Asp Glu Leu Gln Leu Asn
 65                  70                  75                  80

Ile Glu Asp Met Gln Trp Gly Lys Gly Val Arg Glu Ile Pro Ala Ser
                 85                  90                  95

Val Cys Thr Leu Pro Cys Lys Pro Gly Gln Arg Lys Lys Thr Gln Lys
            100                 105                 110

Gly Thr Pro Cys Cys Trp Thr Cys Glu Pro Cys Asp Gly Tyr Gln Tyr
        115                 120                 125

Gln Phe Asp Glu Met Thr Cys Gln His Cys Pro Tyr Asp Gln Arg Pro
    130                 135                 140

Asn Glu Asn Arg Thr Gly Cys Gln Asp Ile Pro Ile Ile Lys Leu Glu
145                 150                 155                 160

Trp His Ser Pro Trp Ala Val Ile Pro Val Phe Leu Ala Met Leu Gly
                165                 170                 175

Ile Ile Ala Thr Ile Phe Val Met Ala Thr Phe Ile Arg Tyr Asn Asp
            180                 185                 190

Thr Pro Ile Val Arg Ala Ser Gly Arg Glu Leu Ser Tyr Val Leu Leu
```

```
                195                 200                 205
Thr Gly Ile Phe Leu Cys Tyr Ile Ile Thr Phe Leu Met Ile Ala Lys
        210                 215                 220

Pro Asp Val Ala Val Cys Ser Phe Arg Arg Val Phe Leu Gly Leu Gly
225                 230                 235                 240

Met Cys Ile Ser Tyr Ala Ala Leu Leu Thr Lys Thr Asn Arg Ile Tyr
                245                 250                 255

Arg Ile Phe Glu Gln Gly Lys Lys Ser Val Thr Ala Pro Arg Leu Ile
            260                 265                 270

Ser Pro Thr Ser Gln Leu Ala Ile Thr Ser Ser Leu Ile Ser Val Gln
        275                 280                 285

Leu Leu Gly Val Phe Ile Trp Phe Gly Val Asp Pro Pro Asn Ile Ile
    290                 295                 300

Ile Asp Tyr Asp Glu His Lys Thr Met Asn Pro Glu Gln Ala Arg Gly
305                 310                 315                 320

Val Leu Lys Cys Asp Ile Thr Asp Leu Gln Ile Ile Cys Ser Leu Gly
                325                 330                 335

Tyr Ser Ile Leu Leu Met Val Thr Cys Thr Val Tyr Ala Ile Lys Thr
            340                 345                 350

Arg Gly Val Pro Glu Asn Phe Asn Glu Ala Lys Pro Ile Gly Phe Thr
        355                 360                 365

Met Tyr Thr Thr Cys Ile Val Trp Leu Ala Phe Ile Pro Ile Phe Phe
    370                 375                 380

Gly Thr Ala Gln Ser Ala Glu Lys Leu Tyr Ile Gln Thr Thr Thr Leu
385                 390                 395                 400

Thr Ile Ser Met Asn Leu Ser Ala Ser Val Ala Leu Gly Met Leu Tyr
                405                 410                 415

Met Pro Lys Val Tyr Ile Ile Phe His Pro Glu Leu Asn Val Gln
            420                 425                 430

Lys Arg Lys Arg Ser Phe Lys Ala Val Val Thr Ala Ala Thr Met Ser
        435                 440                 445

Ser Arg Leu Ser His Lys Pro Ser Asp Arg Pro Asn Gly Glu Ala Lys
    450                 455                 460

Thr Glu Leu Cys Glu Asn Val Asp Pro Asn Ser Glu Lys Cys Asn Cys
465                 470                 475                 480

Tyr

<210> SEQ ID NO 9
<211> LENGTH: 558
<212> TYPE: DNA
<213> ORGANISM: Homo sapiens
<220> FEATURE:
<221> NAME/KEY: CDS
<222> LOCATION: (1)..(558)

<400> SEQUENCE: 9 atg gtc cag ctg agg aag ctg ctc cgc gtc ctg act ttg atg aag ttc    48
Met Val Gln Leu Arg Lys Leu Leu Arg Val Leu Thr Leu Met Lys Phe
  1               5                  10                  15 ccc tgc tgc gtg ctg gag gtg ctc ctg tgc gcg ctg gcg gcg gcg gcg    96
Pro Cys Cys Val Leu Glu Val Leu Leu Cys Ala Leu Ala Ala Ala Ala
             20                  25                  30 cgc ggc cag gag atg tac gcc ccg cac tca atc cgg atc gag ggg gac   144
Arg Gly Gln Glu Met Tyr Ala Pro His Ser Ile Arg Ile Glu Gly Asp
         35                  40                  45 gtc acc ctc ggg ggg ctg ttc ccc gta cac gcc aag ggt ccc agc gga   192
```

```
Val Thr Leu Gly Gly Leu Phe Pro Val His Ala Lys Gly Pro Ser Gly
         50                  55                  60 gtg ccc tgc ggc gac atc aag agg gaa aac ggg atc cac agg ctg gaa          240
Val Pro Cys Gly Asp Ile Lys Arg Glu Asn Gly Ile His Arg Leu Glu
 65                  70                  75                  80 gcg atg ctc tac gcc ctg gac cag atc aac agt gat ccc aac cta ctg          288
Ala Met Leu Tyr Ala Leu Asp Gln Ile Asn Ser Asp Pro Asn Leu Leu
                 85                  90                  95 ccc aac gtg acg ctg ggc gcg cgg atc ctg gac act tgt tcc agg gac          336
Pro Asn Val Thr Leu Gly Ala Arg Ile Leu Asp Thr Cys Ser Arg Asp
                100                 105                 110 act tac gcg ctc gaa cag tcg ctt act ttc gtc cag gcg ctc atc cag          384
Thr Tyr Ala Leu Glu Gln Ser Leu Thr Phe Val Gln Ala Leu Ile Gln
            115                 120                 125 aag gac acc tcc gac gtg cgc tgc acc aac ggc gaa ccg ccg gtt ttc          432
Lys Asp Thr Ser Asp Val Arg Cys Thr Asn Gly Glu Pro Pro Val Phe
130                 135                 140 gtc aag ccg gag aaa gta gtt gga gtg att ggg gct tcg ggg agt tcg          480
Val Lys Pro Glu Lys Val Val Gly Val Ile Gly Ala Ser Gly Ser Ser
145                 150                 155                 160 gtc tcc atc atg gta gcc aac atc ctg agg ctc ttc cag atc ccc cag          528
Val Ser Ile Met Val Ala Asn Ile Leu Arg Leu Phe Gln Ile Pro Gln
                165                 170                 175 att agt tat gca tca acg gca ccc gag cta                                  558
Ile Ser Tyr Ala Ser Thr Ala Pro Glu Leu
            180                 185

<210> SEQ ID NO 10
<211> LENGTH: 186
<212> TYPE: PRT
<213> ORGANISM: Homo sapiens

<400> SEQUENCE: 10

Met Val Gln Leu Arg Lys Leu Leu Arg Val Leu Thr Leu Met Lys Phe
  1               5                  10                  15

Pro Cys Cys Val Leu Glu Val Leu Leu Cys Ala Leu Ala Ala Ala Ala
                 20                  25                  30

Arg Gly Gln Glu Met Tyr Ala Pro His Ser Ile Arg Ile Glu Gly Asp
             35                  40                  45

Val Thr Leu Gly Gly Leu Phe Pro Val His Ala Lys Gly Pro Ser Gly
 50                  55                  60

Val Pro Cys Gly Asp Ile Lys Arg Glu Asn Gly Ile His Arg Leu Glu
 65                  70                  75                  80

Ala Met Leu Tyr Ala Leu Asp Gln Ile Asn Ser Asp Pro Asn Leu Leu
                 85                  90                  95

Pro Asn Val Thr Leu Gly Ala Arg Ile Leu Asp Thr Cys Ser Arg Asp
                100                 105                 110

Thr Tyr Ala Leu Glu Gln Ser Leu Thr Phe Val Gln Ala Leu Ile Gln
            115                 120                 125

Lys Asp Thr Ser Asp Val Arg Cys Thr Asn Gly Glu Pro Pro Val Phe
130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu
            180                 185
```

-continued

```
<210> SEQ ID NO 11
<211> LENGTH: 2745
<212> TYPE: DNA
<213> ORGANISM: Homo sapiens
<220> FEATURE:
<221> NAME/KEY: CDS
<222> LOCATION: (1)..(2745)

<400> SEQUENCE: 11
```

| | | | | | | | | | | | | | | | | |
|---|---|---|---|---|---|---|---|---|---|---|---|---|---|---|---|---|
| atg | gtc | cag | ctg | agg | aag | ctg | ctc | cgc | gtc | ctg | act | ttg | atg | aag | ttc | 48 |
| Met | Val | Gln | Leu | Arg | Lys | Leu | Leu | Arg | Val | Leu | Thr | Leu | Met | Lys | Phe | |
| 1 | | | | 5 | | | | | 10 | | | | | 15 | | |
| ccc | tgc | tgc | gtg | ctg | gag | gtg | ctc | ctg | tgc | gcg | ctg | gcg | gcg | gcg | gcg | 96 |
| Pro | Cys | Cys | Val | Leu | Glu | Val | Leu | Leu | Cys | Ala | Leu | Ala | Ala | Ala | Ala | |
| | | | 20 | | | | | 25 | | | | | 30 | | | |
| cgc | ggc | cag | gag | atg | tac | gcc | ccg | cac | tca | atc | cgg | atc | gag | ggg | gac | 144 |
| Arg | Gly | Gln | Glu | Met | Tyr | Ala | Pro | His | Ser | Ile | Arg | Ile | Glu | Gly | Asp | |
| | | 35 | | | | | 40 | | | | | 45 | | | | |
| gtc | acc | ctc | ggg | ggg | ctg | ttc | ccc | gta | cac | gcc | aag | ggt | ccc | agc | gga | 192 |
| Val | Thr | Leu | Gly | Gly | Leu | Phe | Pro | Val | His | Ala | Lys | Gly | Pro | Ser | Gly | |
| | 50 | | | | | 55 | | | | | 60 | | | | | |
| gtg | ccc | tgc | ggc | gac | atc | aag | agg | gaa | aac | ggg | atc | cac | agg | ctg | gaa | 240 |
| Val | Pro | Cys | Gly | Asp | Ile | Lys | Arg | Glu | Asn | Gly | Ile | His | Arg | Leu | Glu | |
| 65 | | | | | 70 | | | | | 75 | | | | | 80 | |
| gcg | atg | ctc | tac | gcc | ctg | gac | cag | atc | aac | agt | gat | ccc | aac | cta | ctg | 288 |
| Ala | Met | Leu | Tyr | Ala | Leu | Asp | Gln | Ile | Asn | Ser | Asp | Pro | Asn | Leu | Leu | |
| | | | 85 | | | | | 90 | | | | | 95 | | | |
| ccc | aac | gtg | acg | ctg | ggc | gcg | cgg | atc | ctg | gac | act | tgt | tcc | agg | gac | 336 |
| Pro | Asn | Val | Thr | Leu | Gly | Ala | Arg | Ile | Leu | Asp | Thr | Cys | Ser | Arg | Asp | |
| | | | 100 | | | | | 105 | | | | | 110 | | | |
| act | tac | gcg | ctc | gaa | cag | tcg | ctt | act | ttc | gtc | cag | gcg | ctc | atc | cag | 384 |
| Thr | Tyr | Ala | Leu | Glu | Gln | Ser | Leu | Thr | Phe | Val | Gln | Ala | Leu | Ile | Gln | |
| | | 115 | | | | | 120 | | | | | 125 | | | | |
| aag | gac | acc | tcc | gac | gtg | cgc | tgc | acc | aac | ggc | gaa | ccg | ccg | gtt | ttc | 432 |
| Lys | Asp | Thr | Ser | Asp | Val | Arg | Cys | Thr | Asn | Gly | Glu | Pro | Pro | Val | Phe | |
| | 130 | | | | | 135 | | | | | 140 | | | | | |
| gtc | aag | ccg | gag | aaa | gta | gtt | gga | gtg | att | ggg | gct | tcg | ggg | agt | tcg | 480 |
| Val | Lys | Pro | Glu | Lys | Val | Val | Gly | Val | Ile | Gly | Ala | Ser | Gly | Ser | Ser | |
| 145 | | | | | 150 | | | | | 155 | | | | | 160 | |
| gtc | tcc | atc | atg | gta | gcc | aac | atc | ctg | agg | ctc | ttc | cag | atc | ccc | cag | 528 |
| Val | Ser | Ile | Met | Val | Ala | Asn | Ile | Leu | Arg | Leu | Phe | Gln | Ile | Pro | Gln | |
| | | | 165 | | | | | 170 | | | | | 175 | | | |
| att | agt | tat | gca | tca | acg | gca | ccc | gag | cta | agt | gat | gac | cgg | cgc | tat | 576 |
| Ile | Ser | Tyr | Ala | Ser | Thr | Ala | Pro | Glu | Leu | Ser | Asp | Asp | Arg | Arg | Tyr | |
| | | | 180 | | | | | 185 | | | | | 190 | | | |
| gac | ttc | ttc | tct | cgc | gtg | gtg | cca | ccc | gat | tcc | ttc | caa | gcc | cag | gcc | 624 |
| Asp | Phe | Phe | Ser | Arg | Val | Val | Pro | Pro | Asp | Ser | Phe | Gln | Ala | Gln | Ala | |
| | | 195 | | | | | 200 | | | | | 205 | | | | |
| atg | gta | gac | att | gta | aag | gcc | cta | ggc | tgg | aat | tat | gtg | tct | acc | ctc | 672 |
| Met | Val | Asp | Ile | Val | Lys | Ala | Leu | Gly | Trp | Asn | Tyr | Val | Ser | Thr | Leu | |
| | 210 | | | | | 215 | | | | | 220 | | | | | |
| gca | tcg | gaa | gga | agt | tat | gga | gag | aaa | ggt | gtg | gag | tcc | ttc | acg | cag | 720 |
| Ala | Ser | Glu | Gly | Ser | Tyr | Gly | Glu | Lys | Gly | Val | Glu | Ser | Phe | Thr | Gln | |
| 225 | | | | | 230 | | | | | 235 | | | | | 240 | |
| att | tcc | aaa | gag | gca | ggt | gga | ctc | tgc | att | gcc | cag | tcc | gtg | aga | atc | 768 |
| Ile | Ser | Lys | Glu | Ala | Gly | Gly | Leu | Cys | Ile | Ala | Gln | Ser | Val | Arg | Ile | |
| | | | 245 | | | | | 250 | | | | | 255 | | | |
| ccc | cag | gaa | cgc | aaa | gac | agg | acc | att | gac | ttt | gat | aga | att | atc | aaa | 816 |
| Pro | Gln | Glu | Arg | Lys | Asp | Arg | Thr | Ile | Asp | Phe | Asp | Arg | Ile | Ile | Lys | |
| | | | 260 | | | | | 265 | | | | | 270 | | | |

```
cag ctc ctg gac acc ccc aac tcc agg gcc gtc gtg att ttt gcc aac      864
Gln Leu Leu Asp Thr Pro Asn Ser Arg Ala Val Val Ile Phe Ala Asn
        275                 280                 285 gat gag gat ata aag cag atc ctt gca gca gcc aaa aga gct gac caa      912
Asp Glu Asp Ile Lys Gln Ile Leu Ala Ala Ala Lys Arg Ala Asp Gln
    290                 295                 300 gtt ggc cat ttt ctt tgg gtg gga tca gac agc tgg gga tcc aaa ata      960
Val Gly His Phe Leu Trp Val Gly Ser Asp Ser Trp Gly Ser Lys Ile
305                 310                 315                 320 aac cca ctg cac cag cat gaa gat atc gca gaa ggg gcc atc acc att     1008
Asn Pro Leu His Gln His Glu Asp Ile Ala Glu Gly Ala Ile Thr Ile
                325                 330                 335 cag ccc aag cga gcc acg gtg gaa ggg ttt gat gcc tac ttt acg tcc     1056
Gln Pro Lys Arg Ala Thr Val Glu Gly Phe Asp Ala Tyr Phe Thr Ser
            340                 345                 350 cgt aca ctt gaa aac aac aga aga aat gta tgg ttt gcc gaa tac tgg     1104
Arg Thr Leu Glu Asn Asn Arg Arg Asn Val Trp Phe Ala Glu Tyr Trp
        355                 360                 365 gag gaa aac ttc aac tgc aag ttg acg att agt ggg tca aaa aaa gaa     1152
Glu Glu Asn Phe Asn Cys Lys Leu Thr Ile Ser Gly Ser Lys Lys Glu
370                 375                 380 gac aca gat cgc aaa tgc aca gga cag gag aga att gga aaa gat tcc     1200
Asp Thr Asp Arg Lys Cys Thr Gly Gln Glu Arg Ile Gly Lys Asp Ser
385                 390                 395                 400 aac tat gag cag gag ggt aaa gtc cag ttc gtg att gac gca gtc tat     1248
Asn Tyr Glu Gln Glu Gly Lys Val Gln Phe Val Ile Asp Ala Val Tyr
                405                 410                 415 gct atg gct cac gcc ctt cac cac atg aac aag gat ctc tgt gct gac     1296
Ala Met Ala His Ala Leu His His Met Asn Lys Asp Leu Cys Ala Asp
            420                 425                 430 tac cgg ggt gtc tgc cca gag atg gag caa gct gga ggc aag aag ttg     1344
Tyr Arg Gly Val Cys Pro Glu Met Glu Gln Ala Gly Gly Lys Lys Leu
        435                 440                 445 ctg aag tat ata cgc aat gtt aat ttc aat ggt agt gct ggc act cca     1392
Leu Lys Tyr Ile Arg Asn Val Asn Phe Asn Gly Ser Ala Gly Thr Pro
450                 455                 460 gtg atg ttt aac aag aac ggg gat gca cct ggg cgt tat gac atc ttt     1440
Val Met Phe Asn Lys Asn Gly Asp Ala Pro Gly Arg Tyr Asp Ile Phe
465                 470                 475                 480 cag tac cag acc aca aac acc agc aac ccg ggt tac cgt ctg atc ggg     1488
Gln Tyr Gln Thr Thr Asn Thr Ser Asn Pro Gly Tyr Arg Leu Ile Gly
                485                 490                 495 cag tgg aca gac gaa ctt cag ctc aat ata gaa gac atg cag tgg ggt     1536
Gln Trp Thr Asp Glu Leu Gln Leu Asn Ile Glu Asp Met Gln Trp Gly
            500                 505                 510 aaa gga gtc cga gag ata ccc gcc tca gtg tgc aca cta cca tgt aag     1584
Lys Gly Val Arg Glu Ile Pro Ala Ser Val Cys Thr Leu Pro Cys Lys
        515                 520                 525 cca gga cag aga aag aag aca cag aaa gga act cct tgc tgt tgg acc     1632
Pro Gly Gln Arg Lys Lys Thr Gln Lys Gly Thr Pro Cys Cys Trp Thr
530                 535                 540 tgt gag cct tgc gat ggt tac cag tac cag ttt gat gag atg aca tgc     1680
Cys Glu Pro Cys Asp Gly Tyr Gln Tyr Gln Phe Asp Glu Met Thr Cys
545                 550                 555                 560 cag cat tgc ccc tat gac cag agg ccc aat gaa aat cga acc gga tgc     1728
Gln His Cys Pro Tyr Asp Gln Arg Pro Asn Glu Asn Arg Thr Gly Cys
                565                 570                 575 cag gat att ccc atc atc aaa ctg gag tgg cac tcc ccc tgg gct gtg     1776
Gln Asp Ile Pro Ile Ile Lys Leu Glu Trp His Ser Pro Trp Ala Val
            580                 585                 590
```

```
att cct gtc ttc ctg gca atg ttg ggg atc att gcc acc atc ttt gtc      1824
Ile Pro Val Phe Leu Ala Met Leu Gly Ile Ile Ala Thr Ile Phe Val
        595                 600                 605 atg gcc act ttc atc cgc tac aat gac acg ccc att gtc cgg gca tct      1872
Met Ala Thr Phe Ile Arg Tyr Asn Asp Thr Pro Ile Val Arg Ala Ser
610                 615                 620 ggg cgg gaa ctc agc tat gtt ctt ttg acg ggc atc ttt ctt tgc tac      1920
Gly Arg Glu Leu Ser Tyr Val Leu Leu Thr Gly Ile Phe Leu Cys Tyr
625                 630                 635                 640 atc atc act ttc ctg atg att gcc aaa cca gat gtg gca gtg tgt tct      1968
Ile Ile Thr Phe Leu Met Ile Ala Lys Pro Asp Val Ala Val Cys Ser
                645                 650                 655 ttc cgg cga gtt ttc ttg ggc ttg ggt atg tgc atc agt tat gca gcc      2016
Phe Arg Arg Val Phe Leu Gly Leu Gly Met Cys Ile Ser Tyr Ala Ala
            660                 665                 670 ctc ttg acg aaa aca aat cgg att tat cgc ata ttt gag cag ggc aag      2064
Leu Leu Thr Lys Thr Asn Arg Ile Tyr Arg Ile Phe Glu Gln Gly Lys
        675                 680                 685 aaa tca gta aca gct ccc aga ctc ata agc cca aca tca caa ctg gca      2112
Lys Ser Val Thr Ala Pro Arg Leu Ile Ser Pro Thr Ser Gln Leu Ala
690                 695                 700 atc act tcc agt tta ata tca gtt cag ctt cta ggg gtg ttc att tgg      2160
Ile Thr Ser Ser Leu Ile Ser Val Gln Leu Leu Gly Val Phe Ile Trp
705                 710                 715                 720 ttt ggt gtt gat cca ccc aac atc atc ata gac tac gat gaa cac aag      2208
Phe Gly Val Asp Pro Pro Asn Ile Ile Ile Asp Tyr Asp Glu His Lys
                725                 730                 735 aca atg aac cct gag caa gcc aga ggg gtt ctc aag tgt gac att aca      2256
Thr Met Asn Pro Glu Gln Ala Arg Gly Val Leu Lys Cys Asp Ile Thr
            740                 745                 750 gat ctc caa atc att tgc tcc ttg gga tat agc att ctt ctc atg gtc      2304
Asp Leu Gln Ile Ile Cys Ser Leu Gly Tyr Ser Ile Leu Leu Met Val
        755                 760                 765 aca tgt act gtg tat gcc atc aag act cgg ggt gta ccc gag aat ttt      2352
Thr Cys Thr Val Tyr Ala Ile Lys Thr Arg Gly Val Pro Glu Asn Phe
770                 775                 780 aac gaa gcc aag ccc att gga ttc act atg tac acg aca tgt ata gta      2400
Asn Glu Ala Lys Pro Ile Gly Phe Thr Met Tyr Thr Thr Cys Ile Val
785                 790                 795                 800 tgg ctt gcc ttc att cca att ttt ttt ggc acc gct caa tca gcg gaa      2448
Trp Leu Ala Phe Ile Pro Ile Phe Phe Gly Thr Ala Gln Ser Ala Glu
                805                 810                 815 aag ctc tac ata caa act acc acg ctt aca atc tcc atg aac cta agt      2496
Lys Leu Tyr Ile Gln Thr Thr Thr Leu Thr Ile Ser Met Asn Leu Ser
            820                 825                 830 gca tca gtg gcg ctg ggg atg cta tac atg ccg aaa gtg tac atc atc      2544
Ala Ser Val Ala Leu Gly Met Leu Tyr Met Pro Lys Val Tyr Ile Ile
        835                 840                 845 att ttc cac cct gaa ctc aat gtc cag aaa cgg aag cga agc ttc aag      2592
Ile Phe His Pro Glu Leu Asn Val Gln Lys Arg Lys Arg Ser Phe Lys
850                 855                 860 gcg gta gtc aca gca gcc acc atg tca tcg agg ctg tca cac aaa ccc      2640
Ala Val Val Thr Ala Ala Thr Met Ser Ser Arg Leu Ser His Lys Pro
865                 870                 875                 880 agt gac aga ccc aac ggt gag gca aag acc gag ctc tgt gaa aac gta      2688
Ser Asp Arg Pro Asn Gly Glu Ala Lys Thr Glu Leu Cys Glu Asn Val
                885                 890                 895 gac cca aac agc cct gct gca aaa aag aag tat gtc agt tat aat aac      2736
Asp Pro Asn Ser Pro Ala Ala Lys Lys Lys Tyr Val Ser Tyr Asn Asn
```

-continued

```
                    900             905             910
ctg gtt atc                                                                 2745
Leu Val Ile
        915
```

<210> SEQ ID NO 12
<211> LENGTH: 915
<212> TYPE: PRT
<213> ORGANISM: Homo sapiens

<400> SEQUENCE: 12

```
Met Val Gln Leu Arg Lys Leu Leu Arg Val Leu Thr Leu Met Lys Phe
 1               5                  10                  15

Pro Cys Cys Val Leu Glu Val Leu Leu Cys Ala Leu Ala Ala Ala
            20                  25                  30

Arg Gly Gln Glu Met Tyr Ala Pro His Ser Ile Arg Ile Glu Gly Asp
        35                  40                  45

Val Thr Leu Gly Gly Leu Phe Pro Val His Ala Lys Gly Pro Ser Gly
    50                  55                  60

Val Pro Cys Gly Asp Ile Lys Arg Glu Asn Gly Ile His Arg Leu Glu
65                  70                  75                  80

Ala Met Leu Tyr Ala Leu Asp Gln Ile Asn Ser Asp Pro Asn Leu Leu
                85                  90                  95

Pro Asn Val Thr Leu Gly Ala Arg Ile Leu Asp Thr Cys Ser Arg Asp
            100                 105                 110

Thr Tyr Ala Leu Glu Gln Ser Leu Thr Phe Val Gln Ala Leu Ile Gln
        115                 120                 125

Lys Asp Thr Ser Asp Val Arg Cys Thr Asn Gly Glu Pro Pro Val Phe
130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
            180                 185                 190

Asp Phe Phe Ser Arg Val Val Pro Pro Asp Ser Phe Gln Ala Gln Ala
        195                 200                 205

Met Val Asp Ile Val Lys Ala Leu Gly Trp Asn Tyr Val Ser Thr Leu
    210                 215                 220

Ala Ser Glu Gly Ser Tyr Gly Glu Lys Gly Val Glu Ser Phe Thr Gln
225                 230                 235                 240

Ile Ser Lys Glu Ala Gly Gly Leu Cys Ile Ala Gln Ser Val Arg Ile
                245                 250                 255

Pro Gln Glu Arg Lys Asp Arg Thr Ile Asp Phe Asp Arg Ile Ile Lys
            260                 265                 270

Gln Leu Leu Asp Thr Pro Asn Ser Arg Ala Val Val Ile Phe Ala Asn
        275                 280                 285

Asp Glu Asp Ile Lys Gln Ile Leu Ala Ala Ala Lys Arg Ala Asp Gln
    290                 295                 300

Val Gly His Phe Leu Trp Val Gly Ser Asp Ser Trp Gly Ser Lys Ile
305                 310                 315                 320

Asn Pro Leu His Gln His Glu Asp Ile Ala Glu Gly Ala Ile Thr Ile
                325                 330                 335

Gln Pro Lys Arg Ala Thr Val Glu Gly Phe Asp Ala Tyr Phe Thr Ser
            340                 345                 350
```

```
Arg Thr Leu Glu Asn Asn Arg Arg Asn Val Trp Phe Ala Glu Tyr Trp
        355                 360                 365

Glu Glu Asn Phe Asn Cys Lys Leu Thr Ile Ser Gly Ser Lys Lys Glu
    370                 375                 380

Asp Thr Asp Arg Lys Cys Thr Gly Gln Glu Arg Ile Gly Lys Asp Ser
385                 390                 395                 400

Asn Tyr Glu Gln Glu Gly Lys Val Gln Phe Val Ile Asp Ala Val Tyr
                405                 410                 415

Ala Met Ala His Ala Leu His His Met Asn Lys Asp Leu Cys Ala Asp
                420                 425                 430

Tyr Arg Gly Val Cys Pro Glu Met Glu Gln Ala Gly Gly Lys Lys Leu
        435                 440                 445

Leu Lys Tyr Ile Arg Asn Val Asn Phe Asn Gly Ser Ala Gly Thr Pro
    450                 455                 460

Val Met Phe Asn Lys Asn Gly Asp Ala Pro Gly Arg Tyr Asp Ile Phe
465                 470                 475                 480

Gln Tyr Gln Thr Thr Asn Thr Ser Asn Pro Gly Tyr Arg Leu Ile Gly
                485                 490                 495

Gln Trp Thr Asp Glu Leu Gln Leu Asn Ile Glu Asp Met Gln Trp Gly
            500                 505                 510

Lys Gly Val Arg Glu Ile Pro Ala Ser Val Cys Thr Leu Pro Cys Lys
        515                 520                 525

Pro Gly Gln Arg Lys Lys Thr Gln Lys Gly Thr Pro Cys Cys Trp Thr
    530                 535                 540

Cys Glu Pro Cys Asp Gly Tyr Gln Tyr Gln Phe Asp Glu Met Thr Cys
545                 550                 555                 560

Gln His Cys Pro Tyr Asp Gln Arg Pro Asn Glu Asn Arg Thr Gly Cys
                565                 570                 575

Gln Asp Ile Pro Ile Ile Lys Leu Glu Trp His Ser Pro Trp Ala Val
            580                 585                 590

Ile Pro Val Phe Leu Ala Met Leu Gly Ile Ile Ala Thr Ile Phe Val
        595                 600                 605

Met Ala Thr Phe Ile Arg Tyr Asn Asp Thr Pro Ile Val Arg Ala Ser
    610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
                645                 650                 655

Phe Arg Arg Val Phe Leu Gly Leu Gly Met Cys Ile Ser Tyr Ala Ala
            660                 665                 670

Leu Leu Thr Lys Thr Asn Arg Ile Tyr Arg Ile Phe Glu Gln Gly Lys
        675                 680                 685

Lys Ser Val Thr Ala Pro Arg Leu Ile Ser Pro Thr Ser Gln Leu Ala
    690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
                725                 730                 735

Thr Met Asn Pro Glu Gln Ala Arg Gly Val Leu Lys Cys Asp Ile Thr
            740                 745                 750

Asp Leu Gln Ile Ile Cys Ser Leu Gly Tyr Ser Ile Leu Leu Met Val
        755                 760                 765
```

```
Thr Cys Thr Val Tyr Ala Ile Lys Thr Arg Gly Val Pro Glu Asn Phe
        770                 775                 780
Asn Glu Ala Lys Pro Ile Gly Phe Thr Met Tyr Thr Thr Cys Ile Val
785                 790                 795                 800
Trp Leu Ala Phe Ile Pro Ile Phe Phe Gly Thr Ala Gln Ser Ala Glu
                805                 810                 815
Lys Leu Tyr Ile Gln Thr Thr Thr Leu Thr Ile Ser Met Asn Leu Ser
            820                 825                 830
Ala Ser Val Ala Leu Gly Met Leu Tyr Met Pro Lys Val Tyr Ile Ile
        835                 840                 845
Ile Phe His Pro Glu Leu Asn Val Gln Lys Lys Arg Ser Phe Lys
    850                 855                 860
Ala Val Val Thr Ala Ala Thr Met Ser Ser Arg Leu Ser His Lys Pro
865                 870                 875                 880
Ser Asp Arg Pro Asn Gly Glu Ala Lys Thr Glu Leu Cys Glu Asn Val
                885                 890                 895
Asp Pro Asn Ser Pro Ala Ala Lys Lys Lys Tyr Val Ser Tyr Asn Asn
            900                 905                 910
Leu Val Ile
        915

<210> SEQ ID NO 13
<211> LENGTH: 2766
<212> TYPE: DNA
<213> ORGANISM: Homo sapiens
<220> FEATURE:
<221> NAME/KEY: CDS
<222> LOCATION: (1)..(2766)

<400> SEQUENCE: 13 atg gtc cag ctg agg aag ctg ctc cgc gtc ctg act ttg atg aag ttc     48
Met Val Gln Leu Arg Lys Leu Leu Arg Val Leu Thr Leu Met Lys Phe
 1               5                  10                  15 ccc tgc tgc gtg ctg gag gtg ctc ctg tgc gcg ctg gcg gcg gcg gcg     96
Pro Cys Cys Val Leu Glu Val Leu Leu Cys Ala Leu Ala Ala Ala Ala
                20                  25                  30 cgc ggc cag gag atg tac gcc ccg cac tca atc cgg atc gag ggg gac    144
Arg Gly Gln Glu Met Tyr Ala Pro His Ser Ile Arg Ile Glu Gly Asp
            35                  40                  45 gtc acc ctc ggg ggg ctg ttc ccc gta cac gcc aag ggt ccc agc gga    192
Val Thr Leu Gly Gly Leu Phe Pro Val His Ala Lys Gly Pro Ser Gly
        50                  55                  60 gtg ccc tgc ggc gac atc aag agg gaa aac ggg atc cac agg ctg gaa    240
Val Pro Cys Gly Asp Ile Lys Arg Glu Asn Gly Ile His Arg Leu Glu
65                  70                  75                  80 gcg atg ctc tac gcc ctg gac cag atc aac agt gat ccc aac cta ctg    288
Ala Met Leu Tyr Ala Leu Asp Gln Ile Asn Ser Asp Pro Asn Leu Leu
                85                  90                  95 ccc aac gtg acg ctg ggc gcg cgg atc ctg gac act tgt tcc agg gac    336
Pro Asn Val Thr Leu Gly Ala Arg Ile Leu Asp Thr Cys Ser Arg Asp
                100                 105                 110 act tac gcg ctc gaa cag tcg ctt act ttc gtc cag gcg ctc atc cag    384
Thr Tyr Ala Leu Glu Gln Ser Leu Thr Phe Val Gln Ala Leu Ile Gln
            115                 120                 125 aag gac acc tcc gac gtg cgc tgc acc aac ggc gaa ccg ccg gtt ttc    432
Lys Asp Thr Ser Asp Val Arg Cys Thr Asn Gly Glu Pro Pro Val Phe
        130                 135                 140 gtc aag ccg gag aaa gta gtt gga gtg att ggg gct tcg ggg agt tcg    480
Val Lys Pro Glu Lys Val Val Gly Val Ile Gly Ala Ser Gly Ser Ser
145                 150                 155                 160
```

-continued

| | | |
|---|---|---|
| 145 150 155 160 | | |
| gtc tcc atc atg gta gcc aac atc ctg agg ctc ttc cag atc ccc cag<br>Val Ser Ile Met Val Ala Asn Ile Leu Arg Leu Phe Gln Ile Pro Gln<br>165 170 175 | 528 | |
| att agt tat gca tca acg gca ccc gag cta agt gat gac cgg cgc tat<br>Ile Ser Tyr Ala Ser Thr Ala Pro Glu Leu Ser Asp Asp Arg Arg Tyr<br>180 185 190 | 576 | |
| gac ttc ttc tct cgc gtg gtg cca ccc gat tcc ttc caa gcc cag gcc<br>Asp Phe Phe Ser Arg Val Val Pro Pro Asp Ser Phe Gln Ala Gln Ala<br>195 200 205 | 624 | |
| atg gta gac att gta aag gcc cta ggc tgg aat tat gtg tct acc ctc<br>Met Val Asp Ile Val Lys Ala Leu Gly Trp Asn Tyr Val Ser Thr Leu<br>210 215 220 | 672 | |
| gca tcg gaa gga agt tat gga gag aaa ggt gtg gag tcc ttc acg cag<br>Ala Ser Glu Gly Ser Tyr Gly Glu Lys Gly Val Glu Ser Phe Thr Gln<br>225 230 235 240 | 720 | |
| att tcc aaa gag gca ggt gga ctc tgc att gcc cag tcc gtg aga atc<br>Ile Ser Lys Glu Ala Gly Gly Leu Cys Ile Ala Gln Ser Val Arg Ile<br>245 250 255 | 768 | |
| ccc cag gaa cgc aaa gac agg acc att gac ttt gat aga att atc aaa<br>Pro Gln Glu Arg Lys Asp Arg Thr Ile Asp Phe Asp Arg Ile Ile Lys<br>260 265 270 | 816 | |
| cag ctc ctg gac acc ccc aac tcc agg gcc gtc gtg att ttt gcc aac<br>Gln Leu Leu Asp Thr Pro Asn Ser Arg Ala Val Val Ile Phe Ala Asn<br>275 280 285 | 864 | |
| gat gag gat ata aag cag atc ctt gca gca gcc aaa aga gct gac caa<br>Asp Glu Asp Ile Lys Gln Ile Leu Ala Ala Ala Lys Arg Ala Asp Gln<br>290 295 300 | 912 | |
| gtt ggc cat ttt ctt tgg gtg gga tca gac agc tgg gga tcc aaa ata<br>Val Gly His Phe Leu Trp Val Gly Ser Asp Ser Trp Gly Ser Lys Ile<br>305 310 315 320 | 960 | |
| aac cca ctg cac cag cat gaa gat atc gca gaa ggg gcc atc acc att<br>Asn Pro Leu His Gln His Glu Asp Ile Ala Glu Gly Ala Ile Thr Ile<br>325 330 335 | 1008 | |
| cag ccc aag cga gcc acg gtg gaa ggg ttt gat gcc tac ttt acg tcc<br>Gln Pro Lys Arg Ala Thr Val Glu Gly Phe Asp Ala Tyr Phe Thr Ser<br>340 345 350 | 1056 | |
| cgt aca ctt gaa aac aac aga aga aat gta tgg ttt gcc gaa tac tgg<br>Arg Thr Leu Glu Asn Asn Arg Arg Asn Val Trp Phe Ala Glu Tyr Trp<br>355 360 365 | 1104 | |
| gag gaa aac ttc aac tgc aag ttg acg att agt ggg tca aaa aaa gaa<br>Glu Glu Asn Phe Asn Cys Lys Leu Thr Ile Ser Gly Ser Lys Lys Glu<br>370 375 380 | 1152 | |
| gac aca gat cgc aaa tgc aca gga cag gag aga att gga aaa gat tcc<br>Asp Thr Asp Arg Lys Cys Thr Gly Gln Glu Arg Ile Gly Lys Asp Ser<br>385 390 395 400 | 1200 | |
| aac tat gag cag gag ggt aaa gtc cag ttc gtg att gac gca gtc tat<br>Asn Tyr Glu Gln Glu Gly Lys Val Gln Phe Val Ile Asp Ala Val Tyr<br>405 410 415 | 1248 | |
| gct atg gct cac gcc ctt cac cac atg aac aag gat ctc tgt gct gac<br>Ala Met Ala His Ala Leu His His Met Asn Lys Asp Leu Cys Ala Asp<br>420 425 430 | 1296 | |
| tac cgg ggt gtc tgc cca gag atg gag caa gct gga ggc aag aag ttg<br>Tyr Arg Gly Val Cys Pro Glu Met Glu Gln Ala Gly Gly Lys Lys Leu<br>435 440 445 | 1344 | |
| ctg aag tat ata cgc aat gtt aat ttc aat ggt agt gct ggc act cca<br>Leu Lys Tyr Ile Arg Asn Val Asn Phe Asn Gly Ser Ala Gly Thr Pro<br>450 455 460 | 1392 | |
| gtg atg ttt aac aag aac ggg gat gca cct ggg cgt tat gac atc ttt | 1440 | |

```
                                                                            -continued Val Met Phe Asn Lys Asn Gly Asp Ala Pro Gly Arg Tyr Asp Ile Phe
465                 470                 475                 480 cag tac cag acc aca aac acc agc aac ccg ggt tac cgt ctg atc ggg           1488
Gln Tyr Gln Thr Thr Asn Thr Ser Asn Pro Gly Tyr Arg Leu Ile Gly
                    485                 490                 495 cag tgg aca gac gaa ctt cag ctc aat ata gaa gac atg cag tgg ggt           1536
Gln Trp Thr Asp Glu Leu Gln Leu Asn Ile Glu Asp Met Gln Trp Gly
                500                 505                 510 aaa gga gtc cga gag ata ccc gcc tca gtg tgc aca cta cca tgt aag           1584
Lys Gly Val Arg Glu Ile Pro Ala Ser Val Cys Thr Leu Pro Cys Lys
            515                 520                 525 cca gga cag aga aag aag aca cag aaa gga act cct tgc tgt tgg acc           1632
Pro Gly Gln Arg Lys Lys Thr Gln Lys Gly Thr Pro Cys Cys Trp Thr
        530                 535                 540 tgt gag cct tgc gat ggt tac cag tac cag ttt gat gag atg aca tgc           1680
Cys Glu Pro Cys Asp Gly Tyr Gln Tyr Gln Phe Asp Glu Met Thr Cys
545                 550                 555                 560 cag cat tgc ccc tat gac cag agg ccc aat gaa aat cga acc gga tgc           1728
Gln His Cys Pro Tyr Asp Gln Arg Pro Asn Glu Asn Arg Thr Gly Cys
                    565                 570                 575 cag gat att ccc atc atc aaa ctg gag tgg cac tcc ccc tgg gct gtg           1776
Gln Asp Ile Pro Ile Ile Lys Leu Glu Trp His Ser Pro Trp Ala Val
                580                 585                 590 att cct gtc ttc ctg gca atg ttg ggg atc att gcc acc atc ttt gtc           1824
Ile Pro Val Phe Leu Ala Met Leu Gly Ile Ile Ala Thr Ile Phe Val
            595                 600                 605 atg gcc act ttc atc cgc tac aat gac acg ccc att gtc cgg gca tct           1872
Met Ala Thr Phe Ile Arg Tyr Asn Asp Thr Pro Ile Val Arg Ala Ser
        610                 615                 620 ggg cgg gaa ctc agc tat gtt ctt ttg acg ggc atc ttt ctt tgc tac           1920
Gly Arg Glu Leu Ser Tyr Val Leu Leu Thr Gly Ile Phe Leu Cys Tyr
625                 630                 635                 640 atc atc act ttc ctg atg att gcc aaa cca gat gtg gca gtg tgt tct           1968
Ile Ile Thr Phe Leu Met Ile Ala Lys Pro Asp Val Ala Val Cys Ser
                    645                 650                 655 ttc cgg cga gtt ttc ttg ggc ttg ggt atg tgc atc agt tat gca gcc           2016
Phe Arg Arg Val Phe Leu Gly Leu Gly Met Cys Ile Ser Tyr Ala Ala
                660                 665                 670 ctc ttg acg aaa aca aat cgg att tat cgc ata ttt gag cag ggc aag           2064
Leu Leu Thr Lys Thr Asn Arg Ile Tyr Arg Ile Phe Glu Gln Gly Lys
            675                 680                 685 aaa tca gta aca gct ccc aga ctc ata agc cca aca tca caa ctg gca           2112
Lys Ser Val Thr Ala Pro Arg Leu Ile Ser Pro Thr Ser Gln Leu Ala
        690                 695                 700 atc act tcc agt tta ata tca gtt cag ctt cta ggg gtg ttc att tgg           2160
Ile Thr Ser Ser Leu Ile Ser Val Gln Leu Leu Gly Val Phe Ile Trp
705                 710                 715                 720 ttt ggt gtt gat cca ccc aac atc atc ata gac tac gat gaa cac aag           2208
Phe Gly Val Asp Pro Pro Asn Ile Ile Ile Asp Tyr Asp Glu His Lys
                    725                 730                 735 aca atg aac cct gag caa gcc aga ggg gtt ctc aag tgt gac att aca           2256
Thr Met Asn Pro Glu Gln Ala Arg Gly Val Leu Lys Cys Asp Ile Thr
                740                 745                 750 gat ctc caa atc att tgc tcc ttg gga tat agc att ctt ctc atg gtc           2304
Asp Leu Gln Ile Ile Cys Ser Leu Gly Tyr Ser Ile Leu Leu Met Val
            755                 760                 765 aca tgt act gtg tat gcc atc aag act cgg ggt gta ccc gag aat ttt           2352
Thr Cys Thr Val Tyr Ala Ile Lys Thr Arg Gly Val Pro Glu Asn Phe
        770                 775                 780
```

-continued

```
aac gaa gcc aag ccc att gga ttc act atg tac acg aca tgt ata gta    2400
Asn Glu Ala Lys Pro Ile Gly Phe Thr Met Tyr Thr Thr Cys Ile Val
785                 790                 795                 800 tgg ctt gcc ttc att cca att ttt ttt ggc acc gct caa tca gcg gaa    2448
Trp Leu Ala Phe Ile Pro Ile Phe Phe Gly Thr Ala Gln Ser Ala Glu
                805                 810                 815 aag ctc tac ata caa act acc acg ctt aca atc tcc atg aac cta agt    2496
Lys Leu Tyr Ile Gln Thr Thr Thr Leu Thr Ile Ser Met Asn Leu Ser
            820                 825                 830 gca tca gtg gcg ctg ggg atg cta tac atg ccg aaa gtg tac atc atc    2544
Ala Ser Val Ala Leu Gly Met Leu Tyr Met Pro Lys Val Tyr Ile Ile
        835                 840                 845 att ttc cac cct gaa ctc aat gtc cag aaa cgg aag cga agc ttc aag    2592
Ile Phe His Pro Glu Leu Asn Val Gln Lys Arg Lys Arg Ser Phe Lys
    850                 855                 860 gcg gta gtc aca gca gcc acc atg tca tcg agg ctg tca cac aaa ccc    2640
Ala Val Val Thr Ala Ala Thr Met Ser Ser Arg Leu Ser His Lys Pro
865                 870                 875                 880 agt gac aga ccc aac ggt gag gca aag acc gag ctc tgt gaa aac gta    2688
Ser Asp Arg Pro Asn Gly Glu Ala Lys Thr Glu Leu Cys Glu Asn Val
                885                 890                 895 gac cca aac aac tgt ata cca cca gta aga aag agt gta caa aag tct    2736
Asp Pro Asn Asn Cys Ile Pro Pro Val Arg Lys Ser Val Gln Lys Ser
            900                 905                 910 gtt act tgg tac act atc cca cca aca gta                            2766
Val Thr Trp Tyr Thr Ile Pro Pro Thr Val
        915                 920
```

<210> SEQ ID NO 14
<211> LENGTH: 922
<212> TYPE: PRT
<213> ORGANISM: Homo sapiens

<400> SEQUENCE: 14

```
Met Val Gln Leu Arg Lys Leu Arg Val Leu Thr Leu Met Lys Phe
  1               5                  10                  15

Pro Cys Cys Val Leu Glu Val Leu Leu Cys Ala Leu Ala Ala Ala
                 20                  25                  30

Arg Gly Gln Glu Met Tyr Ala Pro His Ser Ile Arg Ile Glu Gly Asp
         35                  40                  45

Val Thr Leu Gly Gly Leu Phe Pro Val His Ala Lys Gly Pro Ser Gly
     50                  55                  60

Val Pro Cys Gly Asp Ile Lys Arg Glu Asn Gly Ile His Arg Leu Glu
 65                  70                  75                  80

Ala Met Leu Tyr Ala Leu Asp Gln Ile Asn Ser Asp Pro Asn Leu Leu
                 85                  90                  95

Pro Asn Val Thr Leu Gly Ala Arg Ile Leu Asp Thr Cys Ser Arg Asp
                100                 105                 110

Thr Tyr Ala Leu Glu Gln Ser Leu Thr Phe Val Gln Ala Leu Ile Gln
        115                 120                 125

Lys Asp Thr Ser Asp Val Arg Cys Thr Asn Gly Glu Pro Pro Val Phe
    130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
            180                 185                 190
```

-continued

```
Asp Phe Phe Ser Arg Val Val Pro Pro Asp Ser Phe Gln Ala Gln Ala
            195                 200                 205
Met Val Asp Ile Val Lys Ala Leu Gly Trp Asn Tyr Val Ser Thr Leu
            210                 215                 220
Ala Ser Glu Gly Ser Tyr Gly Glu Lys Gly Val Glu Ser Phe Thr Gln
225                 230                 235                 240
Ile Ser Lys Glu Ala Gly Gly Leu Cys Ile Ala Gln Ser Val Arg Ile
                245                 250                 255
Pro Gln Glu Arg Lys Asp Arg Thr Ile Asp Phe Asp Arg Ile Ile Lys
            260                 265                 270
Gln Leu Leu Asp Thr Pro Asn Ser Arg Ala Val Val Ile Phe Ala Asn
            275                 280                 285
Asp Glu Asp Ile Lys Gln Ile Leu Ala Ala Ala Lys Arg Ala Asp Gln
            290                 295                 300
Val Gly His Phe Leu Trp Val Gly Ser Asp Ser Trp Gly Ser Lys Ile
305                 310                 315                 320
Asn Pro Leu His Gln His Glu Asp Ile Ala Glu Gly Ala Ile Thr Ile
                325                 330                 335
Gln Pro Lys Arg Ala Thr Val Glu Gly Phe Asp Ala Tyr Phe Thr Ser
            340                 345                 350
Arg Thr Leu Glu Asn Asn Arg Arg Asn Val Trp Phe Ala Glu Tyr Trp
            355                 360                 365
Glu Glu Asn Phe Asn Cys Lys Leu Thr Ile Ser Gly Ser Lys Lys Glu
            370                 375                 380
Asp Thr Asp Arg Lys Cys Thr Gly Gln Glu Arg Ile Gly Lys Asp Ser
385                 390                 395                 400
Asn Tyr Glu Gln Glu Gly Lys Val Gln Phe Val Ile Asp Ala Val Tyr
                405                 410                 415
Ala Met Ala His Ala Leu His His Met Asn Lys Asp Leu Cys Ala Asp
            420                 425                 430
Tyr Arg Gly Val Cys Pro Glu Met Glu Gln Ala Gly Gly Lys Lys Leu
            435                 440                 445
Leu Lys Tyr Ile Arg Asn Val Asn Phe Asn Gly Ser Ala Gly Thr Pro
450                 455                 460
Val Met Phe Asn Lys Asn Gly Asp Ala Pro Gly Arg Tyr Asp Ile Phe
465                 470                 475                 480
Gln Tyr Gln Thr Thr Asn Thr Ser Asn Pro Gly Tyr Arg Leu Ile Gly
                485                 490                 495
Gln Trp Thr Asp Glu Leu Gln Leu Asn Ile Glu Asp Met Gln Trp Gly
            500                 505                 510
Lys Gly Val Arg Glu Ile Pro Ala Ser Val Cys Thr Leu Pro Cys Lys
            515                 520                 525
Pro Gly Gln Arg Lys Lys Thr Gln Lys Gly Thr Pro Cys Cys Trp Thr
            530                 535                 540
Cys Glu Pro Cys Asp Gly Tyr Gln Tyr Gln Phe Asp Glu Met Thr Cys
545                 550                 555                 560
Gln His Cys Pro Tyr Asp Gln Arg Pro Asn Glu Asn Arg Thr Gly Cys
                565                 570                 575
Gln Asp Ile Pro Ile Ile Lys Leu Glu Trp His Ser Pro Trp Ala Val
            580                 585                 590
Ile Pro Val Phe Leu Ala Met Leu Gly Ile Ile Ala Thr Ile Phe Val
            595                 600                 605
```

```
Met Ala Thr Phe Ile Arg Tyr Asn Asp Thr Pro Ile Val Arg Ala Ser
    610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
                645                 650                 655

Phe Arg Arg Val Phe Leu Gly Leu Gly Met Cys Ile Ser Tyr Ala Ala
                660                 665                 670

Leu Leu Thr Lys Thr Asn Arg Ile Tyr Arg Ile Phe Glu Gln Gly Lys
            675                 680                 685

Lys Ser Val Thr Ala Pro Arg Leu Ile Ser Pro Thr Ser Gln Leu Ala
690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
                725                 730                 735

Thr Met Asn Pro Glu Gln Ala Arg Gly Val Leu Lys Cys Asp Ile Thr
                740                 745                 750

Asp Leu Gln Ile Ile Cys Ser Leu Gly Tyr Ser Ile Leu Leu Met Val
            755                 760                 765

Thr Cys Thr Val Tyr Ala Ile Lys Thr Arg Gly Val Pro Glu Asn Phe
770                 775                 780

Asn Glu Ala Lys Pro Ile Gly Phe Thr Met Tyr Thr Thr Cys Ile Val
785                 790                 795                 800

Trp Leu Ala Phe Ile Pro Ile Phe Phe Gly Thr Ala Gln Ser Ala Glu
                805                 810                 815

Lys Leu Tyr Ile Gln Thr Thr Thr Leu Thr Ile Ser Met Asn Leu Ser
            820                 825                 830

Ala Ser Val Ala Leu Gly Met Leu Tyr Met Pro Lys Val Tyr Ile Ile
            835                 840                 845

Ile Phe His Pro Glu Leu Asn Val Gln Lys Arg Lys Arg Ser Phe Lys
850                 855                 860

Ala Val Val Thr Ala Ala Thr Met Ser Ser Arg Leu Ser His Lys Pro
865                 870                 875                 880

Ser Asp Arg Pro Asn Gly Glu Ala Lys Thr Glu Leu Cys Glu Asn Val
                885                 890                 895

Asp Pro Asn Asn Cys Ile Pro Pro Val Arg Lys Ser Val Gln Lys Ser
                900                 905                 910

Val Thr Trp Tyr Thr Ile Pro Pro Thr Val
            915                 920

<210> SEQ ID NO 15
<211> LENGTH: 630
<212> TYPE: DNA
<213> ORGANISM: Homo sapiens
<220> FEATURE:
<221> NAME/KEY: CDS
<222> LOCATION: (1)..(630)
<220> FEATURE:
<221> NAME/KEY: unsure
<222> LOCATION: (65)..(72)
<223> OTHER INFORMATION: Applicants are unsure of the identity of amino
      acids 65, 70 and 72 and nucleotides designated as n could be a or
      g or c or t/u

<400> SEQUENCE: 15 gtg gag gcc ctg cag tgg tct ggc gac ccc cac gag gtg ccc tcg tct      48
Val Glu Ala Leu Gln Trp Ser Gly Asp Pro His Glu Val Pro Ser Ser
```

```
                1               5                        10                       15
        ctg tgc agc ctg ccc tgc ggg ccg ggg gag cgg aag aag atg gtg aag      96
        Leu Cys Ser Leu Pro Cys Gly Pro Gly Glu Arg Lys Lys Met Val Lys
                        20                      25                      30 ggc gtc ccc tgc tgt tgg cac tgc gag gcc tgt gac ggg tac cgc ttc      144
        Gly Val Pro Cys Cys Trp His Cys Glu Ala Cys Asp Gly Tyr Arg Phe
                35                      40                      45 cag gtg gac gag ttc aca tgc gag gcc tgt cct ggg tac atg agg ccc      192
        Gln Val Asp Glu Phe Thr Cys Glu Ala Cys Pro Gly Tyr Met Arg Pro
                50                      55                      60 acn ccc aac cac atc nna ctt nng ccc aca cct gtg gtg cgc ctg agc      240
        Xaa Pro Asn His Ile Xaa Leu Xaa Pro Thr Pro Val Val Arg Leu Ser
        65                      70                      75                      80 tgg tcc tcc ccc tgg gca gcc ccg ccg ctc ctc ctg gcc gtg ctg ggc      288
        Trp Ser Ser Pro Trp Ala Ala Pro Pro Leu Leu Leu Ala Val Leu Gly
                        85                      90                      95 atc gtg gcc act acc acg gtg gtg gcc acc ttc gtg cgg tac aac aac      336
        Ile Val Ala Thr Thr Thr Val Val Ala Thr Phe Val Arg Tyr Asn Asn
                        100                     105                     110 acg ccc atc gtc cgg gcc tcg ggc cga gag ctc agc tac gtc ctc ctc      384
        Thr Pro Ile Val Arg Ala Ser Gly Arg Glu Leu Ser Tyr Val Leu Leu
                        115                     120                     125 acc ggc atc ttc ctc atc tac gcc atc acc ttc ctc atg gtg gct gag      432
        Thr Gly Ile Phe Leu Ile Tyr Ala Ile Thr Phe Leu Met Val Ala Glu
                130                     135                     140 cct ggg gca gcg gtc tgt gcc gcc cgc agg ctc ttc ctg ggc ctg ggc      480
        Pro Gly Ala Ala Val Cys Ala Ala Arg Arg Leu Phe Leu Gly Leu Gly
        145                     150                     155                     160 acg acc ctc agc tac tct gcc ctc ctc acc aag acc aac cgt atc tac      528
        Thr Thr Leu Ser Tyr Ser Ala Leu Leu Thr Lys Thr Asn Arg Ile Tyr
                        165                     170                     175 cgc atc ttt gag cag ggc aag cgc tcg gtc aca ccc cct ccc ttc atc      576
        Arg Ile Phe Glu Gln Gly Lys Arg Ser Val Thr Pro Pro Pro Phe Ile
                        180                     185                     190 agc ccc acc tca cag ctg gtc atc acc ttc agc ctc acc tcc ctg cag      624
        Ser Pro Thr Ser Gln Leu Val Ile Thr Phe Ser Leu Thr Ser Leu Gln
                        195                     200                     205 gtg ggg                                                                630
        Val Gly
            210

<210> SEQ ID NO 16
<211> LENGTH: 210
<212> TYPE: PRT
<213> ORGANISM: Homo sapiens

<400> SEQUENCE: 16

Val Glu Ala Leu Gln Trp Ser Gly Asp Pro His Glu Val Pro Ser Ser
 1               5                       10                      15

Leu Cys Ser Leu Pro Cys Gly Pro Gly Glu Arg Lys Lys Met Val Lys
                20                      25                      30

Gly Val Pro Cys Cys Trp His Cys Glu Ala Cys Asp Gly Tyr Arg Phe
        35                      40                      45

Gln Val Asp Glu Phe Thr Cys Glu Ala Cys Pro Gly Tyr Met Arg Pro
        50                      55                      60

Xaa Pro Asn His Ile Xaa Leu Xaa Pro Thr Pro Val Val Arg Leu Ser
65                      70                      75                      80

Trp Ser Ser Pro Trp Ala Ala Pro Pro Leu Leu Leu Ala Val Leu Gly
                85                      90                      95
```

```
Ile Val Ala Thr Thr Thr Val Val Ala Thr Phe Val Arg Tyr Asn Asn
            100                 105                 110

Thr Pro Ile Val Arg Ala Ser Gly Arg Glu Leu Ser Tyr Val Leu Leu
        115                 120                 125

Thr Gly Ile Phe Leu Ile Tyr Ala Ile Thr Phe Leu Met Val Ala Glu
    130                 135                 140

Pro Gly Ala Ala Val Cys Ala Ala Arg Arg Leu Phe Leu Gly Leu Gly
145                 150                 155                 160

Thr Thr Leu Ser Tyr Ser Ala Leu Leu Thr Lys Thr Asn Arg Ile Tyr
                165                 170                 175

Arg Ile Phe Glu Gln Gly Lys Arg Ser Val Thr Pro Pro Phe Ile
            180                 185                 190

Ser Pro Thr Ser Gln Leu Val Ile Thr Phe Ser Leu Thr Ser Leu Gln
        195                 200                 205

Val Gly
    210

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17
gtcaaggcct cgggccggga                                                    20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
ctagatggca tggttggtgt a                                                  21

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 19
gcgctgcagg cggccgcagg gcctgctagg gctaggagcg gggc                         44

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
gcggaattcc ctccgtgccg tccttctcg                                          29

<210> SEQ ID NO 21
```

```
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21
tatcttgagt ggagtgacat ag                                            22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 22
actgcggacg ttcctctcag g                                             21

<210> SEQ ID NO 23
<211> LENGTH: 22
<212> TYPE: DNA
<213> ORGANISM: Homo sapiens
<220> FEATURE:
<223> OTHER INFORMATION: Description of Artificial Sequence:
      Oligonucleotide primer

<400> SEQUENCE: 23
aacctgagag gaacgtccgc ag                                            22

<210> SEQ ID NO 24
<211> LENGTH: 24
<212> TYPE: DNA
<213> ORGANISM: Homo sapiens
<220> FEATURE:
<223> OTHER INFORMATION: Description of Artificial Sequence:
      Oligonucleotide primer

<400> SEQUENCE: 24
ctacagggtg gaagagcttt gctt                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 25
tcaaagctgc gcatgtgccg acgg                                          24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 26
tcaatagaca gtgttttggc ggtc                                          24
```